(12) United States Patent
Cheng

(10) Patent No.: US 8,278,056 B2
(45) Date of Patent: *Oct. 2, 2012

(54) DETECTION OF EARLY STAGES AND LATE STAGES HPV INFECTION

(75) Inventor: Shuling Cheng, Fremont, CA (US)

(73) Assignee: OncoHealth Corp., San Jose, CA (US)

( * ) Notice: Subject to any disclaimer, the term of this patent is extended or adjusted under 35 U.S.C. 154(b) by 430 days.

This patent is subject to a terminal disclaimer.

(21) Appl. No.: 12/456,076

(22) Filed: Jun. 10, 2009

(65) Prior Publication Data

US 2010/0009387 A1    Jan. 14, 2010

Related U.S. Application Data

(60) Provisional application No. 61/131,991, filed on Jun. 13, 2008, provisional application No. 61/192,912, filed on Sep. 22, 2008.

(51) Int. Cl.
| | |
|---|---|
| *C12Q 1/00* | (2006.01) |
| *C12Q 1/70* | (2006.01) |
| *G01N 33/53* | (2006.01) |
| *G01N 33/542* | (2006.01) |
| *G01N 33/00* | (2006.01) |
| *A61K 39/395* | (2006.01) |
| *A61K 39/42* | (2006.01) |

(52) U.S. Cl. .................. 435/7.1; 435/4; 435/5; 435/7.9; 435/7.92; 424/130.1; 424/147.1

(58) Field of Classification Search .................. None
See application file for complete search history.

(56) References Cited

U.S. PATENT DOCUMENTS

| | | |
|---|---|---|
| 3,633,999 A | 1/1972 | Buckles |
| 4,511,220 A | 4/1985 | Scully |
| 4,619,508 A | 10/1986 | Shibuya et al. |
| 4,744,615 A | 5/1988 | Fan et al. |
| 4,851,978 A | 7/1989 | Ichihara |
| 5,045,447 A | 9/1991 | Minson |
| 5,057,411 A | 10/1991 | Lancaster et al. |
| 5,061,025 A | 10/1991 | Debesis |
| 5,109,465 A | 4/1992 | Klopotek |
| 5,183,755 A | 2/1993 | Ohmoto et al. |
| 5,224,200 A | 6/1993 | Rasmussen et al. |
| 5,233,460 A | 8/1993 | Partlo et al. |
| 5,307,207 A | 4/1994 | Ichihara |
| 5,315,427 A | 5/1994 | Rauch et al. |
| 5,328,785 A | 7/1994 | Smith et al. |
| 5,357,365 A | 10/1994 | Ipposhi et al. |
| 5,401,627 A | 3/1995 | Dillner et al. |
| 5,415,995 A | 5/1995 | Schoolnik et al. |
| 5,453,814 A | 9/1995 | Aiyer |
| 5,561,081 A | 10/1996 | Takenouchi et al. |
| 5,591,574 A | 1/1997 | Orth et al. |
| 5,610,733 A | 3/1997 | Feldman et al. |
| 5,621,529 A | 4/1997 | Gordon et al. |
| 5,629,161 A | 5/1997 | Muller et al. |
| 5,662,410 A | 9/1997 | Suganuma |
| 5,665,535 A | 9/1997 | Orth et al. |
| 5,679,509 A | 10/1997 | Wheeler et al. |
| 5,695,770 A | 12/1997 | Raychaudhuri et al. |
| 5,699,191 A | 12/1997 | Fork |
| 5,754,278 A | 5/1998 | Kurtz |
| 5,876,723 A | 3/1999 | Cole et al. |
| 5,888,888 A | 3/1999 | Talwar et al. |
| 5,914,389 A | 6/1999 | Huibregtse et al. |
| 6,013,262 A | 1/2000 | Frazer et al. |
| 6,228,578 B1 | 5/2001 | Impraim et al. |
| 6,329,167 B1 | 12/2001 | Patterson et al. |
| 6,355,424 B1 | 3/2002 | Lorinez et al. |
| 6,420,106 B1 | 7/2002 | Gyllensten et al. |
| 6,489,105 B1 | 12/2002 | Matlashewski et al. |
| 6,524,825 B1 | 2/2003 | Mizzen et al. |
| 6,528,278 B2 | 3/2003 | Patterson et al. |
| 6,709,832 B1 | 3/2004 | Doeberitz et al. |
| 6,743,593 B2 | 6/2004 | Hu |
| 6,827,933 B2 | 12/2004 | Orth et al. |
| 6,884,786 B1 | 4/2005 | Kieny et al. |
| 6,890,514 B2 | 5/2005 | Mathur et al. |

(Continued)

FOREIGN PATENT DOCUMENTS

CN    03825051.9    11/2005

(Continued)

OTHER PUBLICATIONS

Selvey et al. An ELISA capture assay for the E7 transforming proteins of HPV16 and HPV18. Journal of Virological Methods 1992, vol. 37, pp. 119-128.*

Griesser et al. Correlation of Immunochemical Detection of HPV L1 Capsid Protein in Pap Smears with Regression of High-Risk HPV Positive Mild-Moderate Dysplasia. Analytical Quantitation and Cytological Histology 2004, vol. 26, pp. 241-245.*

Jeon et al. Immunocytochemical detection of HPV16 E7 in cervical smear. Experimental and Molecular Medicine, Oct. 2007, vol. 39, No. 5, p. 621-628.*

Non-final Office action for U.S. Appl. No. 12/456,053 dated Apr. 6, 2012.

Final Office action for U.S. Appl. No. 12/456,054 dated Apr. 16, 2012.

Non-final Office action for U.S. Appl. No. 11/559,366 dated Dec. 5, 2008.

(Continued)

*Primary Examiner* — Louise Humphrey

(74) *Attorney, Agent, or Firm* — Yi-Shan Yang; Fenwick & West LLP

(57) ABSTRACT

Embodiments of the invention provide methods, monoclonal antibodies, polyclonal antibodies, assays, and kits for detecting HPV infection and HPV related cancer diagnosis, including infection by various HPV genotypes, early and/or late stage HPV-associated or HPV-specific cancers. Various specific or pan monoclonal antibodies recognizing specific epitope for specific HPV protein or HPV type, or common epitope for various HPV proteins or HPV types are obtained. The invention also provides one or more solid surface to coat the testing cell lysate. Also, the anti-HPV antibody can be coated on the solid surface of the invention to capture HPV proteins and detect HPV infection.

19 Claims, 21 Drawing Sheets

U.S. PATENT DOCUMENTS

| | | | |
|---|---|---|---|
| 6,900,035 | B2 | 5/2005 | Mizzen et al. |
| 6,933,123 | B2 | 8/2005 | Hu et al. |
| 6,939,687 | B2 | 9/2005 | Patterson et al. |
| 7,001,995 | B1 | 2/2006 | Neeper et al. |
| 7,078,061 | B2 | 7/2006 | Debad et al. |
| 7,157,233 | B2 | 1/2007 | Fischer et al. |
| 7,361,460 | B2 | 4/2008 | Williams et al. |
| 7,399,467 | B2 | 7/2008 | Lu et al. |
| 7,455,973 | B2 | 11/2008 | Fischer et al. |
| 7,501,261 | B2 | 3/2009 | Meijer et al. |
| 7,510,838 | B2 | 3/2009 | Fischer et al. |
| 7,838,215 | B2 | 11/2010 | Gombrich et al. |
| 7,888,032 | B2 | 2/2011 | Patterson et al. |
| 2001/0034021 | A1 | 10/2001 | Muller et al. |
| 2003/0190602 | A1* | 10/2003 | Pressman et al. .......... 435/5 |
| 2004/0170644 | A1 | 9/2004 | Mailere et al. |
| 2004/0175695 | A1 | 9/2004 | Debad et al. |
| 2004/0260157 | A1 | 12/2004 | Montes et al. |
| 2005/0037017 | A1 | 2/2005 | Mizzen et al. |
| 2005/0037342 | A1 | 2/2005 | Mathur et al. |
| 2005/0042600 | A1 | 2/2005 | Hu et al. |
| 2005/0142541 | A1 | 6/2005 | Lu et al. |
| 2005/0147621 | A1 | 7/2005 | Higgins et al. |
| 2005/0159386 | A1 | 7/2005 | Kieny et al. |
| 2005/0255460 | A1 | 11/2005 | Lu et al. |
| 2005/0255468 | A1 | 11/2005 | Ridder et al. |
| 2005/0260566 | A1 | 11/2005 | Fischer et al. |
| 2006/0029943 | A1 | 2/2006 | Hermonat et al. |
| 2006/0039919 | A1 | 2/2006 | Chang et al. |
| 2006/0121516 | A1 | 6/2006 | Norman et al. |
| 2006/0147906 | A1 | 7/2006 | Zwerschke et al. |
| 2006/0153864 | A1 | 7/2006 | Gissmann et al. |
| 2006/0172285 | A1 | 8/2006 | Patterson |
| 2006/0257849 | A1 | 11/2006 | Zauderer et al. |
| 2006/0269967 | A1 | 11/2006 | Chen et al. |
| 2006/0286595 | A1 | 12/2006 | Fischer et al. |
| 2007/0048833 | A1 | 3/2007 | Sprencher et al. |
| 2007/0059319 | A1 | 3/2007 | Carlson et al. |
| 2007/0065810 | A1 | 3/2007 | Schlegel et al. |
| 2007/0099199 | A1 | 5/2007 | Lu et al. |
| 2007/0111266 | A1 | 5/2007 | Sprencher et al. |
| 2007/0117167 | A1 | 5/2007 | Malinowski et al. |
| 2007/0166699 | A1 | 7/2007 | Zwerschke et al. |
| 2007/0190062 | A1 | 8/2007 | Malinowski et al. |
| 2007/0190529 | A1 | 8/2007 | Ridder et al. |
| 2008/0038738 | A1 | 2/2008 | Weigum et al. |
| 2008/0267982 | A1 | 10/2008 | Kiselev |
| 2009/0047660 | A1 | 2/2009 | Lu et al. |
| 2009/0075377 | A1 | 3/2009 | Lu et al. |
| 2009/0104597 | A1 | 4/2009 | Gombrich et al. |
| 2009/0148864 | A1 | 6/2009 | Fischer et al. |

FOREIGN PATENT DOCUMENTS

| | | |
|---|---|---|
| EP | 0256321 | 2/1988 |
| GB | 2379220 | 5/2003 |
| TW | 95142312 | 11/2006 |
| TW | 100100781 | 1/2010 |
| TW | 201012932 | 4/2010 |
| TW | 201043958 | 12/2010 |
| WO | WO2004085683 | 10/2004 |
| WO | WO2006083984 | 8/2006 |
| WO | WO2007059492 | 5/2007 |
| WO | WO2007095320 | 8/2007 |
| WO | WO2009042488 | 4/2009 |
| WO | WO2009151632 | 12/2009 |
| WO | WO2009151633 | 12/2009 |
| WO | WO2010129821 | 11/2010 |
| WO | WO2011084598 | 7/2011 |

OTHER PUBLICATIONS

Final Office action for U.S. Appl. No. 11/559,366 dated May 5, 2009.
Notice of Allowance for U.S. Appl. No. 11/559,366 dated Jan. 4, 2010.
Non-final Office action for U.S. Appl. No. 12/082,740 dated Jun. 12, 2009.
Final Office action for U.S. Appl. No. 12/082,740 dated Aug. 20, 2010.
Notice of Allowance for U.S. Appl. No. 12/082,740 dated Mar. 8, 2011.
Non-final Office action for U.S. Appl. No. 12/456,053 dated May 31, 2011.
Non-final Office action for U.S. Appl. No. 12/456,054 dated Aug. 17, 2011.
Non-final Office action for U.S. Appl. No. 12/456,055 dated Jul. 22, 2011.
EPO Communication for App. No. 09762928.1-1223/2300824, dated Aug. 15, 2011.
Extended European Search Report for App. No. 09762928.1-1223/2300824, dated Jul. 22, 2011.
EPO Communication for App. No. 06846299.3-2402/1951915, dated Apr. 7, 2010.
Extended European Search Report for App. No. 06846299.3-2402/1951915, dated Jan. 8, 2010.
International Search Report for Int'l App. No. PCT/US2009/003537, dated Oct. 8, 2009.
International Search Report for Int'l App. No. PCT/US2009/003538, dated Oct. 15, 2009.
International Search Report for Int'l App. No. PCT/US2010/033944, dated Jul. 2, 2010.
International Preliminary Report on Patentability for Int'l App. No. PCT/US2009/003538, dated Dec. 14, 2010.
International Preliminary Report on Patentability for Int'l App. No. PCT/US2009/003537, dated Dec. 14, 2010.
Written Opinion of the International Searching Authorigy for Int'l App. No. PCT/US2009/003538, dated Oct. 15, 2009.
Written Opinion of the International Searching Authorigy for Int'l App. No. PCT/US2009/003537, dated Oct. 8, 2009.
Written Opinion of the International Searching Authorigy for Int'l App. No. PCT/US2010/033944, dated Jul. 2, 2010.
International Search Report for Int'l App. No. PCT/US2010/060765, dated Mar. 25, 2011.
Written Opinion of the International Searching Authorigy for Int'l App. No. PCT/US2010/0060765, dated Mar. 25, 2011.
International Search Report for Int'l App. No. PCT/US2006/60883, dated Jul. 18, 2007.
International Preliminary Report on Patentability for Int'l App. No. PCT/US2006/60883, dated Jul. 18, 2007.
Written Opinion of the International Searching Authority for Int'l App. No. PCT/US2006/60883, dated Jul. 18, 2007.
EPO Communication for App. No. 06846299.3-2401, dated Oct. 21, 2011.
Final Office action for U.S. Appl. No. 12/456,055 dated Jan. 6, 2012.
Final Office action for U.S. Appl. No. 12/456,053 dated Nov. 17, 2011.
Non-final Office action for U.S. Appl. No. 12/589,692 dated Feb. 7, 2012.
Non-final Office action for U.S. Appl. No. 12/589,641 dated Feb. 6, 2012.
Non-final Office action for U.S. Appl. No. 12/456,076 dated Feb. 9, 2012.
Advisory action for U.S. Appl. No. 12/456,053 dated Jan. 26, 2012.
Advisory action for U.S. Appl. No. 12/082,740 dated Nov. 3, 2010.
Berumen et al., 2001 Asian-American Variants of Human Papillomavirus 16 and Risk for Cervical Cancer: a Case Control Study. Journal of the National Cancer Institute, vol. 93, No. 17.
Bleul et al., 1991 Human Papillomavirus Type 18 E6 and E7 Antibodies in Human Sera: Increased Anti-E7 Prevalence in Cervical Cancer Patients. Journal of Clinical Microbiology, Aug. 1991, pp. 1579-1588.
Bosch et al, 2002 Te Causal Relation between Human Papillomavirus and Cervical Cancer. J. Clinical Pathology, vol. 55, pp. 244-265.
de Villiers 1997. Papillomavirus and HPV typing. Clin. Dermatol 15:199-206.
Zur Hausen 2002. Papillomavirus and cancer: from basic studies to clinical pplication. Nat. rev. Cancer 2: 342-350.
Kreimer, et al. 2005. HPV 16 semiquantitative viral load and serological biomarkers in oral and oropharyngeal squamous cell carcinomas. Int J Cancer 115: 329-32.

Nindl, et al. 1994. Antibodies against linear and conformational epitopes of the human papillomavirus (HPV) type 16 E6 and E7 oncoproteins in sera of cervical cancer patients. Arch. Virol. 137:341-353.

Sasagawa, et al. 2003. Mucosal immunoglobulin-A and -G responses to oncogenic human papilloma virus capsids. Int J Cancer. Apr. 10, 2003; 104(3): 328-35.

Snijders, et al. 2006 HPV-mediated cervical carcinogenesis: concepts and clinical implications J Pathol 2006; 208: 152-164.

Stacey, et al. "Expression of human papillomavirus type 16 E6 protein by recombinant baculovirus and use for detection of anti-E6 antibodies in human sera", Journal of General Virology vol. 73, pp. 2337-2345.

Stoppler, et al. 1996 Natural Variants of the Human Papillomavirus Type 16 E6 Protein Differ in Their Abilities to Alter Keratinocyte Differentiation and to Induce p53 Degradation. Journal of Virology, p. 6987-6993 vol. 70, No. 10.

Tornesello, et al. 2004 Analysis of human papillomavirus type-16 variants in Italian women with cervical intraepithelial neoplasia and cervical cancer J Med Virol.; 74(1): 117-26.

Viscidi, et al. 1993. Serologic response in human papillomavirus-associated invasive cervical cancer. Int. J. Cancer 55:780-784.

Lehtinen, et al.2001. Human papillomavirus infection, risk for subsequent development of cervical neoplasia and associated population attributable fraction. J Clin Virolo 22:117-124.

Mougin, et al. 2001. Epidemiology of cervical papillomavirus infections. Recent knowledge. Press Med 30: 1017-23.

Arbyn et al., 2009. J Cell Mol Med. vol. 13 No. 4 648-659. "Triage of women with equivocal or low-grade cervical cytology results: a meta-analysis of the HPV test positivity rate".

Andersson et al., 2006. International Journal of Oncology 29: 705-711. "Expression of E6/E7 mRNA from 'high risk' human papillomavirus in relation to CIN grade, viral load and p16INK4a".

Balasubramanian et al., Cancer Epidemiol Biomarkers Prev 2009;18:3008-3017. "Evaluation of an ELISA for p16INK4a as a Screening Test for Cervical Cancer".

Cardenas-Turanzas et al., Gyn Oncology 107 (2007) S138-S146. "The clinical effectiveness of optical spectroscopy for the in vivo diagnosis of cervical intraepithelial neoplasia: Where are we?".

Castle et al., 2010. AACCP. Benefits and risks of HPV testing in cervical cancer screening See Online/Articles DOI:10.1016/S1470-2045(09)70360-2.

Castle et al., American Journal of Obstetrics & Gynecology Oct. 2007 "Risk assessment to guide the prevention of cervical cancer".

Choi et al., Biosensors and Bioelectronics 20 (2005) 2236-2243. "Adenoviral p53 effects and cell-specific E7 protein-protein interactions of human cervical cancer cells".

Cole et al., Journal of Virology, Jun. 1986, vol. 58. No. 3. p. 991-995. "Genome Organization and Nucleotide Sequence of Human Papillomavirus Type 33, Which Is Associated with Cervical Cancer".

Cole et al., J. Mol. Biol. (1987) 193, 599-608. "Nucleotide Sequence and Comparative Analysis of the Human Papillomavirus Type 18 Genome Phylogeny of Papillomaviruses and Repeated Structure of the E6 and E7 Gene Products".

Sawaya 2008 Annals of Internal Medicine vol. 148 • No. 7 p. 557 "Adding Human Papillomavirus Testing to Cytology for Primary Cervical Cancer Screening: Shooting First and Asking Questions Later".

Fuchs et al., Journal of Virology, May 1986, p. 626-634. vol. 58, No. 2 "Epidermodysplasia Verruciformis-Associated Human Papillomavirus 8: Genomic Sequence and Comparative Analysis".

Garcia-Alai et al., Biochemistry 2007, 46, "High-Risk HPV E6 Oncoproteins Assemble into Large Oligomers that Allow Localization of Endogenous Species in Prototypic HPV-Transformed Cell Lines".

Gravitt et al., Vaccine 265 (1008) K42-K52. "New Technologies in Cervical Cancer Screening".

Kulasingam et al., Obstetrics & Gynecology vol. 107, No. 2, Part 1, Feb. 2006 Cost-effectiveness of Extending Cervical Cancer Screening Intervals Among Women With Prior Normal Pap Tests:.

Mao et al., Int. J. Cancer: 120, 2435-2438 (2007) "Evaluation of a new p16INK4a ELISA test and a high-risk HPV DNA test for cervical cancer screening: Results from proof-of-concept study".

Molden et al., Int. J. Cancer: 114, 973-976 (2005) "Predicting CIN2 when detecting HPV mRNA and DNA by PreTect HPV-Proofer and consensus PCR: a 2-year follow-up of women with ASCUS or LSIL Pap smear".

Marimatsu et al., Am J Clin Pathol 2005;123:716-723 "High-Throughput Cervical Cancer Screening Using Intracellular Human Papillomavirus E6 and E7 mRNA Quantification by Flow Cytometry".

NCCN Clinical Practice Guidelines in Oncology™ v.2. 2007 Cervical Cancer Screening.

Negri et al., Am J Surg Pathol 2008;32:1715-1720 "p16ink4a and HPV L1 Immunohistochemistry is Helpful for Estimating the Behavior of Low-grade Dysplastic Lesions of the Cervix Uteri".

Norchip et a;., 22nd. International Papillomavirus Conference, Vancouver, BC, Canada, Apr. 30-May 6, 2005 "Persistent transforming HPV infection may correlate with persistent histologically defined CIN II+ Summary of studies by Frank Karlsen and Hanne Skomedal".

Trope et al., Journal of Clinical Microbiology, Aug. 2009, p. 2458-2464. "Pe rformance of Human Papillomavirus DNA and mRNA Testing Strategies for Women with and without Cervical Neoplasia".

Schiffman et al., Arch Pathol Lab Med—vol. 127, Aug. 2003. "Findings to Date From the ASCUS-LSIL Triage Study (ALTS)." pp. 946-949.

Woodman et al., "The natural history of cervical HPV infection: unresolved issues." Nature Review Cancer, vol. 7 | Jan. 2007 | 11.

Ronco et al., BMC Women's Health 2008, 8:23. "New paradigms in cervical cancer prevention: opportunities and risks">.

Talora et al., Genes Dev. 2002 16: 2252-2263. Specific down-modulation of Notch1 signaling in cervical cancer cells is required for sustained HPV-E6/E7 expression and late steps of malignant transformation.

Tungteakkhun wr al., Arch Virol (2008) 153:397-408. "Cellular binding partners of the human papillomavirus E6 protein".

Sellor et al., Journal of Lower Genital Tract Disease, vol. 15, No. 2, 2011, 169-176. Association of Elevated E6 Oncoprotein With Grade of Cervical Neoplasia Using PDZ InteractionYMediated Precipitation of E6.

Ronco et al., "Effi cacy of human papillomavirus testing for the detection of invasive cervical cancers and cervical intraepithelial neoplasia: a randomised controlled trial:." Published Online Jan. 19, 2010.

Schneider-Gadicke et al., The EMBO Journal vol. 5 No. 9 pp. 2285-2292, 1986. "Different human cervical carcinoma cell lines show similar transcription patterns of human papillomavirus type 18 early genes."

Wentzensen et al., Disease Markers 23 (2007) 315-330. "Biomarkers in cervical cancer screening."

Molder et a;., Cancer Epidemiology Biomarkers and Prevention. 2005, 14, p. 367. Comparison of Human Papillomavirus Messeger DNA and DNA detection: A crodd sectional study of 4136 wk e > 30 years of age with a 2, year fikkiw-up of high=grade squamous intraepitehlial Lesion.

Sawaya et al., 2005. www.nejm.org May 10, 2007. "HPV Vaccination—More Answers, More Questions."

Perez et al., 2009. 25th International Papillomavirus Conference, Sweden. "Detection of HPV E6/E7 Oncoporteins in Cervical Cancer."

Parkin et al., Int. J. Cancer: 80, 827-841 (1999). "Estimates of the Worldwide Incidence of 25 Major Cancers in 1990."

Schneider et al., 1991 Int. j. Gynecol Pathol. 10:1-14 "Prevalence of Human Papillomavirus Genomes in Tissue from the Lower Genital Tract as Detected by Molecular in situ hybridization."

Segnan et al., 1994 European Journal of Cancer vol. 30, 873-875. "Cervical cancer screening. Human benefits and human costs in the evaluation of screening programmes."

Partridge et al., 2008 J. National Compr. Cancer Network 6: 58-82. Abstract only.

Heck et al., 1992 Proc. Natl. Acad. Sci. USA vol. 89, pp. 4442-4446, May 1992. "Efficiency of binding the retinoblastoma protein correlates with the transforming capacity of the E7 oncoproteins of the human papillomaviruses."

Chellappan et al., 1992 Proc. Natl. Acad. Sci. USA vol. 89, pp. 4549-4553, May 1992. "Adenovirus EIA, simian virus 40 tumor antigen, and human papillomavirus E7 protein share the capacity to disrupt the interaction between transcription factor E2F and the retinoblastoma gene product."

Dyson et al., Science 1989. 243: 934-937. "The Human Papilloma Virus-16 E7 Oncoprotein is Able to Bind to the Retinoblastoma Gene Product."

Zerfass et al., J. Virol. 1995, 69(10):6389. "Sequential activation of cyclin E and cyclin A gene expression by human papillomavirus type 16 E7 through sequences necessary for transformation."

Zerfass-Thome et al., 1996 Oncogene 13:2323-2330. "Inactivation of the cdk inhibitor p27KIP1 by the human papillomavirus type 16 E7 oncoprotein."

Saint, M., G. Gildengorin, and G. F. Sawaya. 2005. Current Cervical Neoplasia Screening Practices of Obstetriciaqn/Gynecologists in the US. Am. J. Obstet. Gynecol. 192:414-421.

TIPO Search Report and Communication for Taiwan Invention Patent Application No. 095142312, Mar. 24, 2012. English search report on p. 1.

TIPO Search Report and Communication for Taiwan Invention Patent Application No. 098119611, Mar. 22, 2012. English search report on p. 1.

TIPO Search Report and Communication for Taiwan Invention Patent Application No. 098119612, Mar. 13, 2012. English search report on p. 1.

Volgareva et al., Protein p16 as a marker of dysplastic and neoplastic alterations in cervical epithelial cells. BMC Cancer 2004, 4:58. pp.

Liu et al., Preparation of monoclonal antibodies against human papillomavirus 16 E6 protein. Journal of Monoclonal Antibody, vol. 11 No. 3-4, Dec. 1995. English abstract on p. 3.

Su et al., Expression of human papillomavirus type 16 E6 oncogene production of monoclonal antibodies against HPV 16 E6 protein. Journal of Chinese Microbiology and Immunology, vol. 13 No. 3, 1993. English abstract on p. 4.

Wang et al., Expression of human papillomavirus type 16 L1 and construction of hybridoma cell strain of human papillomavirus type 16 L1 monoclonal antibody. Chin J. Endemiol, Jan. 20, 2007, vol. 26, No. 1. English abstract on p. 1.

La Selvey et al., 1992 Journal of Virological Methods, 37, 119-128. An ELiSA capture assay for the E7 transforming proteins of HPV16 and HPV18.

H Griesser et al., 2004 Analyt Quant Cytol Histol 26, 241-245. "Correlation of Immunochemical Detection of HPV L1 capsid protein in Pap Smears with Regression of High-Rist HPV Positive Milk/Moderate Dysplasia."

SJ Lee et al., J Immunol (2001); 167; 497-504. "Both E6 and E7 Oncoproteins of Human Papillomavirus 16 Inhibit IL-IS-Induced IFN-'Y Production in Human Peripheral Blood Mononuclear and NK Cells."

S Vazquez-Vega et al., BMC Cancer (2007). 7(Suppl 1), A21. "Expression of viral and cellular cycle proteins and proteinases in cervical carcinoma cell lines as possible immunocytochemical markers of malignant phenotype."

J Doorbar, (2006) Clinical Science 1, 10, 525-541. "Molecular biology of human papillomavirus infection and cervical cancer."

M Fiedler et al., (2004) The FASEB Journal vol. 18 pp. 1120-1122. "High level HPV-16 E7 oncoprotein expression correlates with reduced pRb-levels in cervical biopsies."

KH Kim et al., (1994) Yonsei Medical Journal vol. 35, No. 1, pp. 1-9. "Expression and Localization of Human Papillomavirus Type 16 E6 and E7 Open Reading Frame Proteins in Human Epidermal Keratinocyte."

M Fiedler et al., (2005) Journal of General Virology, 86, 3235-3241. "Expression of the high-risk human papillomavirus type 18 and 45 E7 oncoproteins in cervical carcinoma biopsies."

E Guccione et al., (2002) Virology 283, 20-25. "Comparative Analysis of the Intracellular Location of the High- and Low-Risk Human Papillomavirus Oncoproteins."

H Valdovinos-Torres et al., (2008) The Open Virology Journal vol. 2. 15-23. "Different Isoforms of HPV-16 E7 Protein are Present in Cytoplasm and Nucleus."

T Li et al., (2001) Carcinogenesis vol. 22. No. 6 pp. 929-934. "Human papillomavirus type 16 is an important infections factor in the high incidence of esophageal cancer in Anyang area of China."

Blevins et al., Applied and Environmental Microbiology 2007, pp. 1501-1513. "Adaptation of a Luciferase Gene Reporter Aand Iac ExpressionSystem to *Borrelia burgdorferi*."

EA Mirecka et al., (2006) Protein Expression and Purification 48, 281-291. "Expression and purification of His-tagged HPV16 E7 protein active in pRb binding/"

MS Lechner et al., (1994) Journal of Virology, Jul. 1994, p. 4262-4273. "Inhibition of p53 DNA Binding by Human Papillomavirus E6 Proteins."

B Bjorndal et al., (2003) Protein Expression and Purification 31 (2003) 47-55. "Expression and purification of receptor for activated C-kinase 1 (RACKI)."

ND Christensen et al., (1996) Virology 223, 174-184. "Surface Conformational and Linear Epitopes on HPV-16 and HPV×18 L1 Virus-like Particles as Defined by Monoclonal Antibodies".

Y Nomine et al., (2001) Protein Engineering vol.I4 No. 4 pp. 297-305, "A strategy for optimizing the monodispersity of fusion proteins: application to purification of recombinant HPV E6 oncoprotein."

ND Christensen et al., (1994) Journal o/General Virology (1994), 75, 2271-2276. "Assembled baculovirus-expressed human papillomavirus type 11 LI capsid protein virus-like particles are recognized by neutralizing monoclonal antibodies and induce high titres of neutralizing antibodies."

T Oltersdorf et al., (1987) J. gen. Viral. (1987), 68, 2933-2938. "Identification of Human Papillomavirus Type 16 E7 Protein by Monoclonal Antibodies."

P Di Bonito et al., (2006) Infectious Agents and Cancer 2006, 1:6. "Serum antibody response to Human papillomavirus (HPV) infections detected by a novel ELISA technique based on denatured recombinant HPVI6 LI, L2, E4, E6 and E7 proteins."

JF Kearney et al., (1979) The Journal of Immunology, V 123 No. 4 p. 1548-1550. "A New Mouse Myeloma Cell Line That Has Lost Immunoglobulin Expression But Permits the Construction of Antibody-Secreting Hybrid Cell Lines."

K Seedorf et al., The EMBO Journal 1987, vol. 6, pp. 139-144. Identification of Early Proteins of the Human Papilloma Viruses Type 16 (HPV 16) and Type 18 (HPV 18) in Cervical Carcinoma Cells.

D Patel et al., (1989) J. gen. Virol. (1989),70,69-77. "Reactivities of Polyclonal and Monoclonal Antibodies Raised to the Major Capsid Protein of Human Papillomavirus Type 16."

S-H Kee et al., (1997) J. Korean Soc. Microbiol., vol. 32, No. 3, "Generation of Monoclonal Antibodies Against Human Papillomavirus Type16 E7 Protein: Usefulness for Various E7 Detection Systems."

AK Graham et al., (1991) Clin Pathol 1991;44:96-101. "Simultaneous in situ genotyping and phenotyping of human papillomavirus cervical lesions: Comparative sensitivity and specificity."

HG Kochel et al., (1991) Inl. J. Cancer: 48, 682-688. "Occurrence of Antibodies to Lt, L2, E4 and E7 Gene Products of Human Papillomavirus Types 6b, 16 and 18 Among Cervical Cancer Patients and Controls."

AK Ghosh et al., (1993) Int. J. Cancer: 53. 591-596. "Serological Responses to HPV 16 in Cervical Dysplasia and Neoplasia: Correlation of Antibodies to E6 With Cervical Cancer."

SA Jenison et al., (1990) The Journal of Infectious Disease162:60-69. "Evidence of Prevalent Genital-Type Human Papillomavirus Infections in Adults and Children."

T Fule et al., (2006) Virology 348, 289-396. "The presence of human papillomavirus 16 in neural structures and vascular endothelial cells."

Tommasino et al., Oncogene 1993, vol. 8, pp. 195-202. HPV16 E7 Protein Associates with the Protein Kinase p22 CDK2 and Cyclin A.

de Villiers et at., Virology 2004, vol. 324, pp. 17-27. "Classification of Papillomaviruses".

Banks et al., J. gen. Virol. 1987, vol. 68, pp. 1351-1359, "Identification of human papillomavirus type 18 E6 polypeptide in cells derived from human cervical carcinomas".

Thermo Scientific, Product Data Sheet for Human Papilloma Virus type 16-E7 (HPV 16-e7) Ab-1 (TVG701Y) Mouse Monoclonal Antibody. Dec. 8, 2011.

BioDesign Internation, Product Data Sheet for MAb to HPV16 E7 protein 716-218. Feb. 1, 2006.
BioDesign Internation, Product Data Sheet for MAb to HPV16 E7 protein 716-325. Aug. 3, 2005.
Chemicon International, Product Data Sheet for Mouse anti-human Papilloma Virus 16,18 E6 (C1P5) Monoclonal Antibody. Nov. 10, 2000.
Dako, Product Data Sheet for Monoclonal Mouse anti-Human Papillomavirus Clone K1H8. 2010.
G Volgareva et al., BMC Cancer 2004, 4:58. "Protein p16 as a marker of dysplastic and neoplastic alterations in cervical epithelial cells."
Digene Corporation, "hc2 HPV DNA Test," Ref. 5198-1220, 2007, 56 pages.
Andersson et al 2006 Expression of E6/E7 mRNA from high rish human papillomavirus in relation to CIN grade, viral load and p161NK4a Int J oncology 29:70-711.
Keegan et al 2009 Comparison of HPV detection technologies: Hybrid capture 2, preTect HPV prooer and analysis of HPV DNA viral load in HPV 16, HPV 18 and HPV 33 E6/E7 mRNA.
EPO Communication for App. No. 06846299.3, dated May 9, 2012.
Rocha-Zavaleta et al., 1997. British Journal of Cancer 75(8), 1144-1150. Differences in serological IgA responses to recombinant baculovirus-derived human papillomavirus E2 protein in the natural history of cervical neoplasia.
Bosch, et al 1995. Prevalence of human papillomavirus in cervical cancer: a worldwide perspective. J Natl Cancer Inst 87:796-802.
Fisher, et al. "The Association of Human Papillomavirus Type 16 E6 and E7 Antibodies with stage of Cervical Cancer", Gynecologic Oncology 61,73-78 (1996) Article No. 0099.
Guimaraes, et al. 2005. "Immunohistochemical expression of p161NK4a and bcl-2 according to HPV type and to the progression of cervical squamous intraepitheliallesions". J Histochem Cytochem. 53: 509-16).
Hagensee, et al. "Detection of Cervical Antibodies to Human Papillomavirus Type 16 (HPV-16) Capsid Antigens in Relation to Detection of HPV-16 DNA and Cervcal Lesions", The Jourrnal of Infectious Diseases 2000; 181: 1234-9.
Kiviat, et al. 1993. Specific human papillomavirus types as the causal agents of most cervical intraepithelial neoplasia: implications for current views and treatment. J Natl Cancer Inst 85: 934-35.
Koutsky, et al. 1992. A cohort study of the risk of cervical intraepithelial neoplasia grade 2 or 3 in relation to papillomavirus infection. N Engl J med 327:1272-1278. Abstract Only.
Kuroda, et al. 2005. The human papillomavirus E6 and E7 inducible oncogene, hWAPL, exhibits potential as a therapeutic target. Br J Cancer 92:290-3.
Li, et al. 2005. Regulation of apoptosis by papillomavirus E6 oncogene. World J Gastroenterol 11:931-37.
Longworth, et al., 2004. Pathogenesis of human papillomavirus in differentiating epithelia. Microbiol Mol Biol Rev 68: 362-72.
Madrigal, et al. 1997. In vitro antigene therapy targeting HPV-16 E6 and E7 in cervical carcinoma. Gynecol Oncol 64: 18-25.
Meschede, et al. "Antibodies agains Early Proteins of Human Papillomaviruses as Diagnostic Markers for Invasive Cervical Cancer" Journal of Clinical Microbiology Feb. 1998, pp. 475-480.
Munoz, et al. 2003. Epidemiologic classification of human papillomavirus types associated with cervical cancer. N Engl J Med 348:518-27.
Park, et al. 1995. Molecular biology of cervical cancer and its precursors. Cancer 76: 1902-13.
Park, et al. "HPV-16-Related Proteins as the Serolgic Markers in Cervical Neoplasia", Gynecologic Oncology 69,47-55 (1998).
Parkin, et al. 1993. Estimates of the worldwide incidence of eighteen major cancers in 1985. Int J Cancer 54:594-606.
Sehr, et al. "A generic capture ELISA for recombinant proteins fused to glutathione S-transferase: validation for HPV serology" Journal of ImmunoloQical Methods 253 (2001) 153-162.
Solomon, et al. 2002. The 2001 Bethesda Systems. Terminology for reportinQ results of cervical cytoloQY. JAMA 287:2114-19.
Studentsov, et al. "Polymer-Based Enzyme-Linked Immunosorbent Assay Using Human Papillomavirus Type 16 (HPV16) Virus-Like Particles Detects HPV16 Clade-Specific Serologic Responses", Journal of Clinical Microbiology Jul. 2003 pp. 2827-2834.
Sun, et al., "Comparison of Peptide Enzyme-Linked Immunosorbent Assay and Radioimmunoprecipitation Assay with In Vitro-Translated Proteins for Detection of Serum Antibodies to Human Papillomavirus Type 16 E6 and #7 Proteins" Journal of Clinical MicrobioloQY Sep. 1994 pp. 2216-2230.
Tjiong, et al. "Antibodies agains Human Papillomavirus Type 16 and 18 E6 and E7 Proteins in Cervicovaginal Washings and Serum of Patients with Cervical Neoplasia" Virallmjmunolgy vol. 14, No. 4, 2001 pp. 415-424.
Veress, et al. "Human Papillomavirus DNA and Anti-HPV Secretory IgA Antibodies in Cytologically Normal Cervical Specimens" Journal of Medical Virology 43:201-207-(1994).
Walboomers, et al. "Human Papillomavirus is a Necessary Cause of Invasive Cervical Cancer Worldwide", Jouranl of PatholoQv 189: 12-19 (1999).
Wang, et al. "Cervical Mucus Antibodies against Human Papillomavirus Type 16, 18, and 33 Capsids in Relation to Presence of Viral DNA" Journal of Clinical Microbiology Dec. 1996 pp. 3056-3062.
Zumbach, et al "Antibodies Against Oncoproteins E6 and E7 of Human Papillomavirus Types 16 and 18 in Cervical-Carcinoma Patents from Russia", Int. J. Cancer 85, 313-318 (2000) [Publication of the International Union Against Cancer].
Fitzgerald Industries International Inc., Product Data Sheet for Monoclonal Antibody to human Papillomavirus (Early Protein), Human, Clone BF7. 2006.
Wang et al., Am J. Surg Patholo. 2004, vol. 28. No. 7, pp. 901-908 Detection of Human Papillomavirus DNA and Expression of p16, Rb, p53 proteins in small cell carcinomas of the uterine cervix.
Gabriella et al., BMC Cancer. 2007, vol. 7, pp. 25. Characterization of antibodies in single-chain format against the E7 oncoprotein of the human papillomavirus type 16 and their improvement by mutagenesis.
Arbyn, M., P. Sasieni, C. J. L. M. Meijer, C. Clavel, G. Koliopoulos, and J. Dillner. 2006. Chapter 9: Clinical applications of HPV testing: A summary of meta-analyses. Vaccine 24:78-89.
Castle, P. E., J. Dockter, C. Giachetti, F. A. Garcia, M. K. McCormick, A. L. Mitchell, E. B. Holladay, and D. P. Kolk. 2007. A cross-sectional study of a prototype carcinogenic human papillomavirus E6/E7 messenger RNA assay for detection of cervical precancer and cancer. Clinical cancer research : an official journal of the American Association for Cancer Research 13:2599-2605.
Cuschieri, K., and N. Wentzensen. 2008. Human Papillomavirus mRNA and p16 Detection as Biomarkers for the Improved Diagnosis of Cervical Neoplasia. Cancer Edidemiol. Biomarkers Prey. 17:2536-2545.
Dehn, D., K. C. Torkko, and K. R. Shroyer. 2007. Human Papillomavirus Testing and Molecular Markers of Cervical Dysplasia and Carcinoma. Cancer Cytopathology 111:1-14.
O'Sullivan, J. P., R. P. A'Hern, P. A. Chapman, L. Jenkins, R. Smith, and A. a. Nafussi. 1998. A case-control study of truepositive versus false-negative cervical smears in women with cervical intraepithelial neoplasia (CIN) III. Cytopathology 9:155-161.
Yim, E.-K., and J.-S. Park. 2006. Biomarkers in Cervical Cancer. Biomarker Insights 1:215-225.
Schiffman, M., A. G. Glass, N. Wentzensen, B. B. Rush, P. E. Castle, D. R. Scott, J. Buckland, M. E. Sherman, G. Rydzak, P. Kirk, A. T. Lorincz, S. Wacholder, and R. D. Burk. 2011. A long-term prospective study of type-specific human papillomavirus infection and risk of cervical neoplasia among 20,000 women in the Portland Kaiser Cohort Study. Cancer epidemiology, biomarkers & prevention : a publication of the American Association for Cancer Research, cosponsored by the American Society of Preventive Oncology 20:1398-1409.
Schweizer, J., P. S. Lu, C. W. Mahoney, M. Berard-Bergery, M. Ho, V. Ramasamy, J. E. Silver, A. Bisht, Y. Labiad, R. B. Peck, J. Lim, J. Jeronimo, R. Howard, P. E. Gravitt, and P. E. Castle. 2010. Feasibility study of a human papillomavirus E6 oncoprotein test for diagnosis of cervical precancer and cancer. Journal of clinical microbiology 48:4646-4648.
Stoler, M. H., P. E. Castle, D. Solomon, and M. Schiffman. 2007. The Expanded Use of HPV Testing in Gynecologic Practice per ASCCP=Guided Manmagement Requires the Use of Well-Validated Assays. American Journal of Clinical Pathology 127:335-337.

Woodman, C. B. J., S. I. Collins, and L. S. Young. 2007. The natural history of cervical HPV infection: unresolved issues. Nature Reviews Cancer 7:11-22.

Bosch F X, Manos M M, Munoz N, et al 1995. Prevalence of human papillomavirus in cervical cancer: a worldwide perspective. J Natl Cancer Inst 87:796-802.

Kiviat N. B, and Koutsky L A. 1993. Specific human papillomavirus types as the causal agents of most cervical intraepithelial neoplasia: implications for current views and tr.

Koutsky L A, Holmes K K, Critchlow C W, et al. 1992. A cohort study of the risk of cervical intraepithelial neoplasia grade 2 or 3 in relation to papillomavirus infection.

Kuroda M, Kiyono T, Oikawa K, Yoshida K, Mukai K. 2005. The human papillomavirus E6 and E7 inducible oncogene, hWAPL, exhibits potential as a therapeutic target. Br J Cance.

Lehtinen M, Luukkaala T Wallin K L, et al. 2001. Human papillomavirus infection, risk for subsequent development of cervical neoplasia and associated population attributable.

Li T, Zhao L, Liu Z, Han Y, and Fan D. 2005. Regulation of apoptosis by papillomavirus E6 oncogene. World J Gastroenterol 11:931-37.

Longworth M S, Laimins L A, 2004. Pathogenesis of human papillomavirus in differentiating epithelia. Microbiol Mol Biol Rev 68: 362-72.

Madrigal M, Janicek M F, Sevin B U, et al. 1997. In vitro antigene therapy targeting HPV-16 E6 and E7 in cervical carcinoma. Gynecol Oncol 64: 18-25.

Mougin C, Dalstein V, Pretet J L, et al. 2001. Epidemiology of cervical papillomavirus infections. Recent knowledge. Press Med 30: 1017-23.

Munoz N, Bosch X, Sanjose S, Herrero R, et al. 2003. Epidemiologic classification of human papillomavirus types associated with cervical cancer. N Engl J Med 348:518-27.

Park T W, fujiwara H, Wright T C. 1995. Molecular biology of cervical cancer and its precursors. Cancer 76: 1902-13.

Wang H L, Lu D W. 2004. Detection of human papillomavirus DNA and expression of p16, Rb, p53 proteins in small cell carcinomas of the uterine cervix. Am J Surg Pathol. 28: 901-908.

Walboomers J M, Meichers W J, Manos M M, et al. 1999. Human papilomavirus is a necessary cause of invasive cervical cancer worldwide. J Pathol. 189:12-19.

de Villiers E. M. 1997. Papillomavirus and HPV typing. Clin. Dermatol 15:199-206.

Zur Hausen, H. 2002. Papillomavirus and cancer: from basic studies to clinical application. Nat. rev. Cancer 2: 342-350.

Parkin D M, Pisant P and ferlay J. 1993. Estimates of the worldwide incidence of eighteen major cancers in 1985. Int J Cancer 54:594-606.

Solomon D, Davey R, Kurman R A, et al. 2002. The 2001 Bethesda Systems. Terminology for reporting results of cervical cytology. JAMA 287:2114-19.

Guimaraes M C, Goncalves M A, Soares C P, et al. 2005. Immunohistochemical expression of p16INK4a and bcl-2 according to HPV type and to the progression of cervical squamous.

Sasagawa T, Rose RC, Azar KK, Sakai A, Inoue M. 2003. Mucosal immunoglobulin-A and -G responses to oncogenic human papilloma virus capsids.Int J Cancer. Apr. 10, 2003;104(3):32.

Fisher, et al. "The Association of Human Papillomavirus Type 16 E6 and E7 Antibodies with stage of Cervical Cancer", Gynecologic Oncology 61, 73-78 (1996) Article No. 0099.

Veress, et al. "Human Papillomavirus DNA and Anti-HPV Secretory IgA Antibodies in Cytologically Normal Cervical Specimens" Journal of Medical Virology 43:201-207 (1994).

Meschede, et al. "Antibodies agains Early Proteins of Human Papillomaviruses as Diagnostic Markers for Invasive Cervical Cancer" Journal of Clinical Microbiology Feb. 1998, pp.

Park, et al. "HPV-16-Related Proteins as the Serolgic Markers in Cervical Neoplasia", Gynecologic Oncology 69, 47-55 (1998).

Viscidi, R. P., S. Yeping, B. Tsuzaki, F. X. Bosch, N. Munoz, and K. Shah. 1993. Serologic response in human papillomavirus-associated invasive cervical cancer. Int. J. Cancer.

Walboomers, et al. "Human Papillomavirus is a Necessary Cause of Invasive Cervical Cancer Worldwide", Jouranl of Pathology 189: 12-19 (1999).

Zumbach, et al "Antibodies Against Oncoproteins E6 and E7 of Human Papillomavirus Types 16 and 18 in Cervical-Carcinoma Patents from Russia", Int. J. Cancer 85, 313-318 (2000).

Sehr, et al. "A generic capture ELISA for recombinant proteins fused to glutathione S-transferase: validation for HPV serology" Journal of Immunological Methods 253 (2001) 153.

Doeberitz, Magnus Von Knebel "New Molecular tools for efficient screening of cervical cancer", Disease Markers 17 (2001) 123-128.

Berumen et al. 2001 Asian-American Variants of Human Papillomavirus 16 and Risk for Cervical Cancer: a Case-Control Study Journal of the National Cancer Institute, vol. 93, No.

Bosch et al. 2002 The causal relation between human papillomavirus and cervical cancer. J. Clin. Pathol.;55;244-265.

Kreimer A R, Clifford G M, Snijders P J, et al. 2005. HPV 16 semiquantitative viral load and serological biomarkers in oral and oropharyngeal squamous cell carcinomas. Int.

Matlashewski G., et al. The expression of human papillomavirus type 18E6 proteins in bacteria and the production of anti-E6 antibodies J Gen Virol (1986) 67: 1909-1916.

Nair, Pillai 2005 Human papillomavirus and disease mechanisms: relevance to oral and cervical cancers Oral Diseases 11, 350-359.

Snijders et al. 2006 HPV-mediated cervical carcinogenesis: concepts and clinical implications J Pathol 2006; 208: 152-164.

Stoppler, et al. 1996 Natural Variants of the Human Papillomavirus Type 16 E6 Protein Differ in Their Abilities to Alter Keratinocyte Differentiation and to Induce p53 Degra.

Tornesello et al. 2004 Analysis of human papillomavirus type-16 variants in Italian women with cervical intraepithelial neoplasia and cervical cancer. J Med Virol. ;74(1):117-.

Banks et al. 1987 Identification of human papillomavirus type 18 E6 polypeptide in cells derived from human cervical carcinomas J gen Virol (1987) 68:1351-1359.

Oltersdorf et al 1987 Identification of human papillomavirus type 16 E7 protein by monoclonal antibodies J Gen Virol (1987) 68:2933-2938.

Patel et al 1989 Reactivities of polyclonal and monoclonal antibodies raised to the major capsid protein of human papillomavirus type 16 J Gen Vriol 70: 69-77.

Radhakrishna pillai et al 1998 High-risk human papillomavirus infection and E6 protein expression in lesions of the uterine cervix Pathobiology 66(5) 240-246.

Ressler et al 2007 High-risk human popillomavirus E7 oncoprotein detection in cervical squamous cell carcinoma Clin Cancer Res 13(23) 7067-7072.

Seedorf et al 1987 identification of early proteins of the human papillomavirus type 16 (HPV 16) and type (HPV 18) in cervical carcinoma cells EMBO 6(1)139-144.

Fiedler et al 2005 Expression of the high-risk human papillomavirus type 18 and 45 E7 oncoproteins in cervical carcinoma biopsies J Gen Birol 86:3235-3241.

Androphy et al 1987 Identification of the HPV-16 E6 protein from transformed mouse cells and human cervical carcinoma cell lines EMBO 6(4) 989-992.

Andersson et al 2006 Expression of E6/E7 mRNA from high rish human papillomavirus in relation to CIN grade, viral load and p16INK4a Int J oncology 29:70-711.

Keegan et al 2009 Comparison of HPV detection technologies: Hybrid capture 2, preTect HPV proofer and analysis of HPV DNA viral load in HPV 16, HPV 18 and HPV 33 E6/E7 mRNA p.

Inoue et al 1990 a novel monoclonal antibody against squamous cell carcinoma Jpn J Cancer res 81:176-182.

Dorland's Pocket Medical Dictionary, p. 420, 25th Edition, 1995, W,B, Saunders Company. Philadelphia, Pennsylvania, 19106.

Tindle RW et al., 1990 Journal of General Virology. 71, 1347-1354. "Identification of B epitopes in human papillomavirus type 16 E7 open reading frame protein."

Santa Cruz Biotechnology, Inc. Product Data Sheet for sc-18114 E6-AP (C-19). 2006.

Advisory Action for U.S. Appl. No. 12/456,054 dated Jun. 13, 2012.
Advisory action for U.S. Appl. No. 12/456,055 dated Mar. 12, 2012.

* cited by examiner

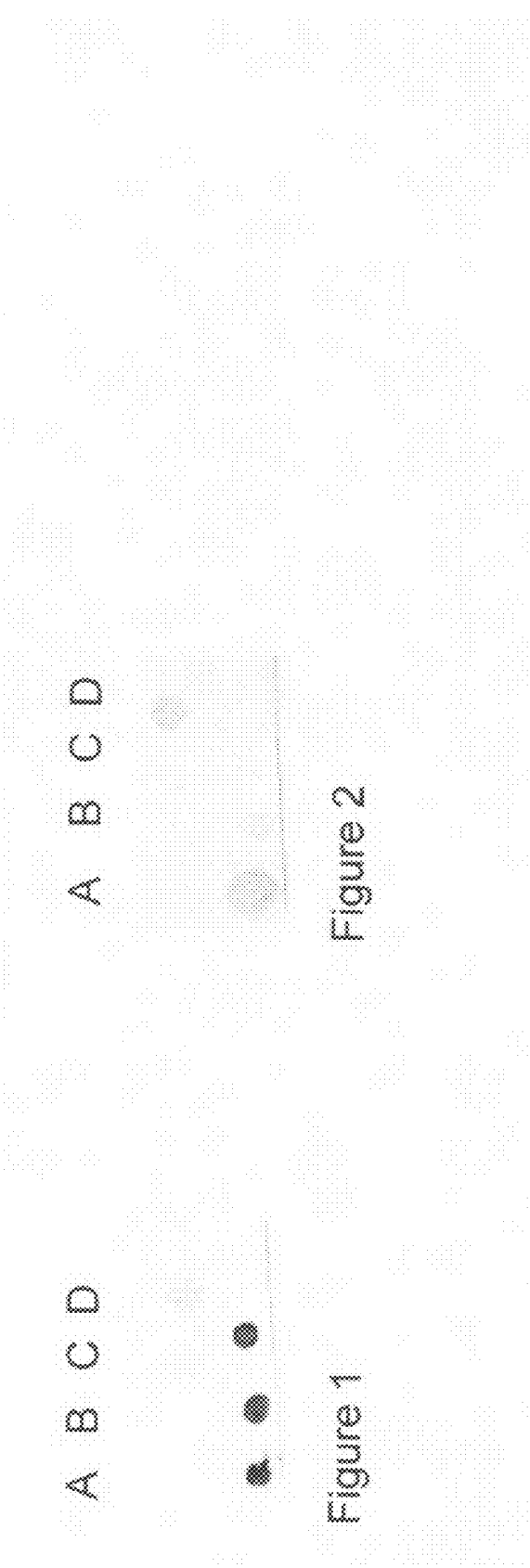
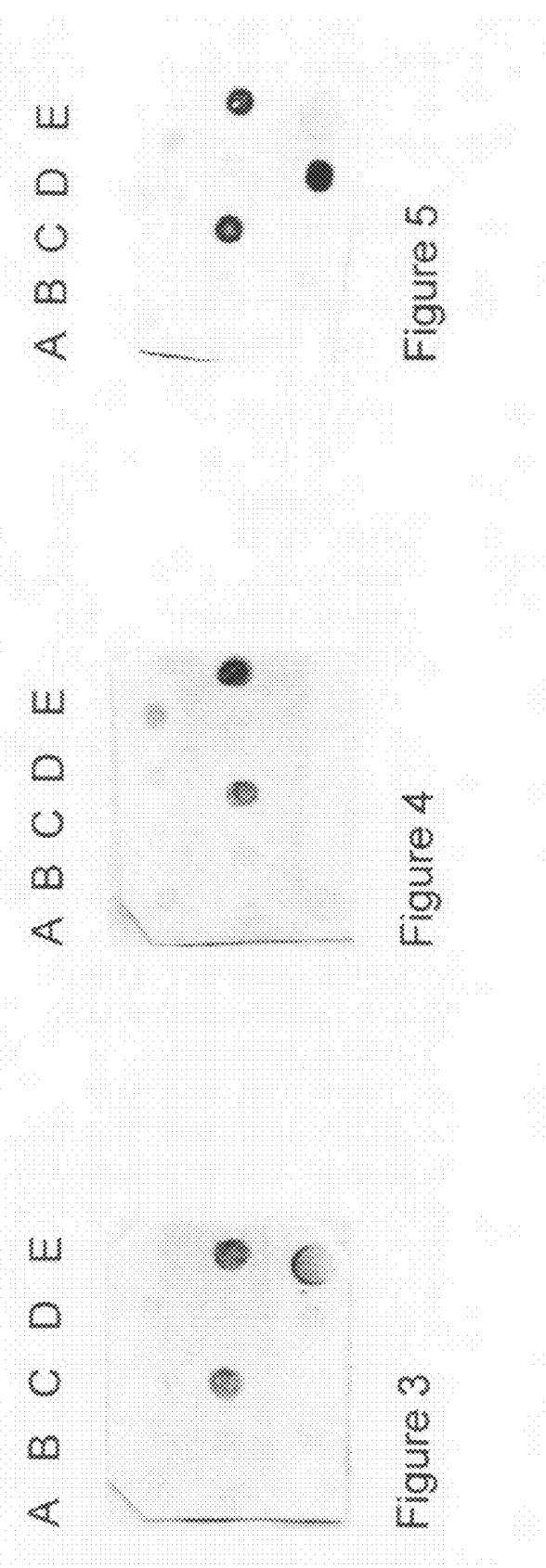
Figure 1
Figure 2
Figure 3
Figure 4
Figure 5

DETECTION OF EARLY STAGES AND LATE STAGES HPV INFECTION

CROSS-REFERENCE TO RELATED APPLICATIONS

This application claims benefit of U.S. provisional patent application Ser. No. 61/131,991, filed Jun. 13, 2008, and U.S. provisional patent application Ser. No. 61/192,912, filed Sep. 22, 2008. Each of the aforementioned related patent applications is herein incorporated by reference.

BACKGROUND OF THE INVENTION

Infection by human papillomaviruses (HPV) at specific epithelium cells to induce epithelial proliferations plays an important role for cervical carcinogenesis. About 99 percent of confirmed cervical cancer cases are found to be associated with HPV infection with biopsy-confirmed squamous intraepithelial lesions (SIL) or cervical intraepithelial neoplasia (CIN). The incidence of HPV infection, primarily transmitted through sexual contact, is highest among young women and about 20 million sexually active men and women worldwide are currently infected. Approximately 1% of the population has genital warts and 4% of women have cervical precancerous lesions, such as low grade of squamous intraepithelial lesion (LSIL), high grade of squamous intraepithelial lesion (HSIL) or atypical squamous cells of undetermined significance (ASCUS).

These lesions, preferentially observed in women aged 35-40 yrs, have a high risk of progression toward invasive cervical cancer. It is generally thought that persistent infection of human papillomavirus (HPV) is essential for developing precancerous epitheliual lesions. Infection of high-risk types of HPV in women with LSIL may or may not progress to HSIL. In fact, remission occurs in the majority of LSIL human subjects while some progress to HSIL. Although 99.7% of cervical cancers are HPV positive, integration of viral genome into the host genome is required to facilitate the necessary genetic expression for developing into HSIL or cancer. In fact, only one in every 10 women with persistent HPV infection may develop higher grades of CIN lesions, such as cervical intraepithelial neoplasia (CIN) grade 2 and grade 3 (CIN2, and CIN3, respectively), and a portion of these epitheliual lesion cases may ultimately progress into cervical cancer.

In the past, screening for cervical cancer has been based on conventional cytology screening tests, e.g., obtaining papanicolaou (Pap) smears for cytological staining tests, and suspicious smears are followed up with colposcopy, and/or histological biopsy. The use of these cytological screening tests contributes to a reduction in the mortality of cervical cancer. However, due to subjective test criteria, there are various drawbacks for pap smear tests: difficulty in obtaining samples, poor inter- and intra-observer agreement, high rates of false negatives and false positives, the requirement of specialized labs staffed with highly trained personnel, and inability to identify the majority of HPV-infected human subjects. More reproducible assays are needed to improve the current screening tests to avoid unnecessary medical intervention and psychological distress for the affected women. The current conventional cervical cytology screening tests have sensitivity varied from about 30% to about 87%.

Nucleic acid tests, such as "DNA Hybrid Capture", have been developed with high assay sensitivity, but these tests are still not ideal, due to not only their high cost, assay operation procedures, the requirements for facility, equipment, and highly trained personnel, but also their very low positive predictive value (PPV) in cervical intraepithelial neoplasia (CIN) testing samples. Assays like PreTect HPV-Proofer® provide the detection of E6/E7 mRNA with sensitivity equivalent to HPV Hybrid Capture tests with higher positive predictive value; but cannot directly detect E6/E7 oncoproteins in situ. In addition, DNA testing can not differentiate disease stages after HPV infection nor can it diagnose different cell lesions (e.g., cannot diffrentiate LSIL from HSIL, nor CIN lesions from non-transforming latent or remissive viral infection). What is needed is a low cost, simple, sensitive and specific assay that can be routinely performed on in a clinical lab or doctor office and is capable of detecting early stages of epithelial lesions, distinguishing LSIL from HSIL, or predicting the risk of progression into cervical cancer.

Known protocols for producing monoclonal antibodies are generally unsuitable for the production of anti-HPV monoclonal antibodies and cannot be used in immunocytochemical diagnostic tests performed on human subjects of the general population. This is because antibodies produced by these protocols will not necessarily react with the naturally occurring HPV viral proteins in infected human cells. It is thought that the epitopes recognized by antibodies if generated by conventional protocols will not necessarily be those epitopes which are resistant to the harsh procedures involved in standard sampling, fixing and storing of clinical specimens. In addition, three problems exist in clinical HPV detection. One is that HPV proteins in clinical samples are present in very small quantities. Secondly, there are too many HPV types and most HPV types present in clinical samples are not known or systemically identified due to the lack of available antibodies. Third, HPV virus can not be cultured in labs by standard tissue culture techniques. Thus, there are no available HPV proteins purified to large quantities as immunogens for generating anti-HPV antibodies, and there are no available HPV proteins or purified anti-HPV antibodies to recognize antiviral antibodies or viral proteins present in clinical samples for clinical HPV detection.

Only 15 out of more than 100 available types of HPV infection are at high risk of developing into cervical intraepithelial neoplasia (CIN) or cervical cancer. Among them, around 70% of reported cervical cancer cases and 50% of reported CIN 2 and CIN 3 cases are caused by two high risk HPV types, HPV type-16 and HPV type-18. However, some progressive cervical cancer cases are reported to be infected by low risk HPV types, while infection of some high risk HPV types will never progress into cervical cancer. Infections by these two prevailing high risk HPV types do not correlate with tumor development or cancer progression. It seems important to identify those HPV-infected human subjects that express particular oncogenic proteins rather than just identify HPV infection by high risk types.

Thus, there is a need to detect the expression of HPV-related oncoproteins in clinical samples as these oncoproteins may serve as cervical cancer biomarkers to better predict the risk of developing into high grade cell lesions or cervical cancer-related diseases. There is also a need to develop anti-HPV antibodies and appropriate HPV immunoassays to detect the presence of invasive cervical cancer and/or HPV-related oncoproteins as cervical cancer biomarkers and predict the risk for malignant transformation of epithelial lesions into cervical cancer.

SUMMARY OF THE INVENTION

Embodiments of the invention provide various solid surface immunoassays for the detection of HPV proteins using various anti-HPV antibodies against recombinant HPV proteins such that infection by high risk and/or low risk HPV types can be detected by a single specific monoclonal antibody and/or a general pan antibody. The invention also provides HPV blot membrane assays, protein chip microarray assays, HPV beads assays, HPV lateral flow rapid tests, HPV vertical flow-through rapid tests, HPV microfluidic rapid tests, direct enzyme immunoassays (EIA), and enzyme linked immunoabsorbant assays (ELISA) to detect the presence of HPV proteins in a biological sample, such as cervical cells or cervical tissues. In addition, kits and devices for performing these assays are also provided.

In one embodiment, a method is provided to detect one or more papillomavirus proteins and includes providing one anti-HPV antibody capable of binding to the one or more papillomavirus proteins from one or more papillomavirus types and present in a clinical sample, providing a solid surface having coated thereon the anti-HPV antibody or the various proteins present in the cell lysate solution, and processing the clinical sample into a cell lysate solution containing various proteins including the one or more papillomavirus proteins. The method further includes reacting the anti-HPV antibody with the cell lysate solution to form a complex of the one or more papillomavirus proteins with the anti-HPV antibody on the solid surface and detecting the complex on the solid surface to confirm the presence of the one or more papillomavirus proteins present in the clinical sample.

In another embodiment, a method is provided for detecting the presence of one or more papillomavirus proteins from one or more papillomavirus types in a biological sample and includes providing a biological sample processed into a cell lysate solution, providing a first anti-HPV antibody immobilized on a solid surface to react with the cell lysate solution, and reacting the cell lysate solution with a second anti-HPV antibody. Both antibodies are capable of binding to one or more papillomavirus proteins from one or more papillomavirus types. The method further includes forming a complex of the one or more papillomavirus proteins with the first and the second anti-HPV antibody on the solid surface, and detecting the formation of the complex on the solid surface for the presence of the one or more papillomavirus proteins in the biological sample.

In addition, a lateral flow through device for detecting the presence of one or more papillomavirus proteins from one or more papillomavirus types in a biological sample is provided according to one embodiment of the invention. The lateral flow through device includes a first solid surface of a strip having a first anti-HPV antibody immobilized on one end of the strip and a second solid surface of a strip having a second anti-HPV antibody on the other end of the strip able to react with a cell lysate solution processed from the biological sample for flowing laterally on the solid surface of the strip to form into a complex with the first anti-HPV antibody. In another embodiment, a vertical flow-through rapid test device is provided for detecting the presence of one or more papillomavirus proteins from one or more papillomavirus types in a biological sample and includes a solid surface of a membrane having a first anti-HPV antibody immobilized thereon to react with a cell lysate solution processed from the biological sample, and a second anti-HPV antibody to be added with the cell lysate solution onto the solid surface of the membrane for flowing vertically through the solid surface and forming into a complex with the first anti-HPV antibody on the solid surface of the membrane.

In one aspect, the first anti-HPV antibody is generated against one or more first recombinant proteins encoded by one or more first papillomavirus genes such that the first anti-HPV antibody is able to capture the one or more papillomavirus proteins in the cell lysate solution onto the solid surface. In another aspect, the second anti-HPV antibody is generated against the same first recombinant proteins encoded by the same papillomavirus genes such that the second anti-HPV antibody is able to bind and detect the one or more papillomavirus proteins in the cell lysate solution.

SUMMARY OF DRAWING

FIG. 1 shows the results of a dot blot assay to detect HPV L1 proteins using an anti-HPV L1 mouse monoclonal antibody according to one embodiment of the invention.

FIG. 2 show the results of another dot blot to detect HPV L1 proteins using the same mouse monoclonal anti-HPV L1 antibody as used in FIG. 1.

FIG. 3 shows the results of using the same blot as shown in FIG. 1 to detect HPV E6 proteins using an anti-HPV E6 mouse monoclonal antibody according to another embodiment of the invention.

FIG. 4 shows the results of using the same dot blot shown in FIG. 2 to detect HPV E6 proteins using the same anti-HPV E6 mouse monoclonal antibody as the one used in FIG. 3 according to another embodiment of the invention.

FIG. 5 shows the results of the same dot blot shown in FIG. 1 and FIG. 3 blotting with an anti-HPV E7 mouse monoclonal antibody to detect HPV E7 proteins according to another embodiment of the invention.

DETAILED DESCRIPTION

Figure 6:
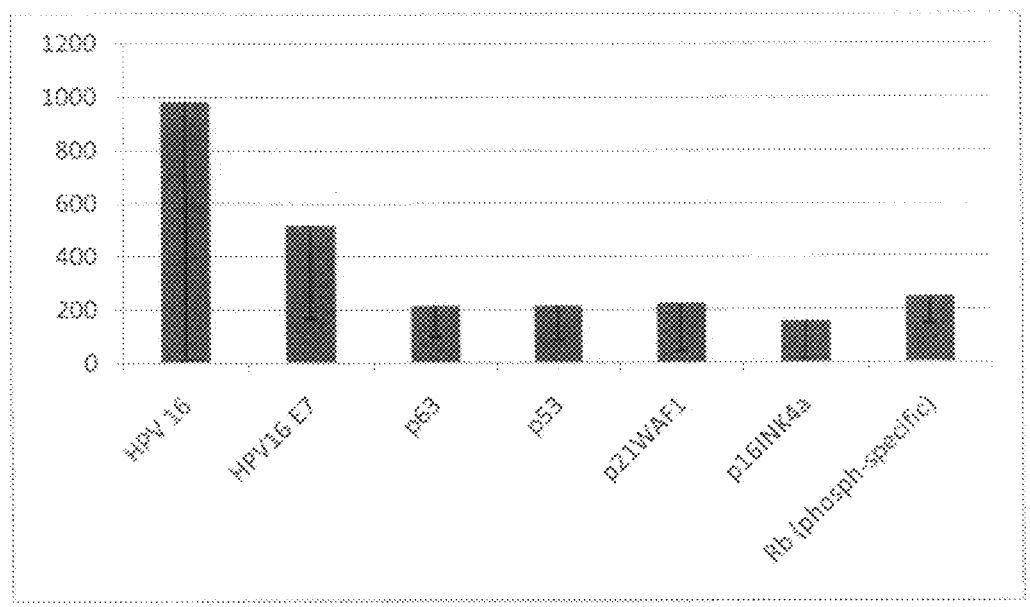
FIG. 6 is a graph showing the average fluorescent intensity results of an antibody microarray assay performed on cell lysate from 10 cervical scrape samples to detect various HPV proteins and various cellular endogenous proteins according to another embodiment of the invention.

Embodiments of the invention provide various immunological assays, methods, detection devices, kits, polypeptides, recombinant proteins, nucleic acids, and monoclonal antibodies against HPV viral proteins useful for detecting HPV infection, including general HPV infection as well as infection by various HPV genotypes, high risk HPVs and low risk HPVs.

In one embodiment, a method is provided for detecting the presence of one or more papillomavirus proteins from one or more papillomavirus types in a biological sample processed into a cell lysate solution to react with an anti-HPV antibody. The anti-HPV antibody is generated against one or more recombinant proteins encoded by one or more papillomavirus genes such that the anti-HPV antibody is able to bind and detect the one or more papillomavirus proteins in the cell lysate solution. As an example, the one or more papillomavirus proteins detected by the methods of the invention may include papillomavirus E6 proteins, papillomavirus E7 proteins, and papillomavirus L1 proteins.

The method further includes providing a solid surface and at least one protein coated on the solid surface. Suitable proteins that can be coated on the solid surface of the invention include, but are not limited to, one or more anti-HPV antibodies, one or more HPV proteins, and various proteins present in a clinical sample. In addition, the anti-HPV antibody is reacted with the cell lysate solution to form a complex of the one or more papillomavirus proteins with the anti-HPV antibody on the solid surface. For example, various proteins present in the clinical sample, including the one or more papillomavirus proteins present in the cell lysate solution, are coated on the solid surface. As another example, the anti-HPV antibody is coated on the solid surface.

The solid surface may include, but is not limited to, a surface of a bead, a surface of a strip, a surface of a rapid test strip, a surface of a membrane, a membrane surface of a vertical flow through device, a surface of a microfluidic device, a surface of a blot membrane, a surface of a protein chip, a glass surface, and a bottom surface of a microtiterplate, among others. For example, the solid surface can be the surfaces of one or more beads and the anti-HPV antibody can be coated thereon to capture one or more papillomavirus proteins on the surfaces of one or more beads and the anti-HPV antibody-papillomavirus protein complexes formed on the surfaces of the beads can be detected by a FACS (Fluorescence-activated cell sorting) detection instrument.

As another example, the solid surface can be a strip of a rapid test device and the one or more papillomavirus proteins bound by the anti-HPV antibody can be detected on the strip of the rapid test device. The anti-HPV antibody can be a first anti-HPV antibody immobilized on one end of the strip, and a second anti-HPV antibody is provided to be added to the other end of the strip. The cell lysate solution for testing the presence of the one or more papillomavirus proteins is also added to the other end of the strip to be recognized by the second anti-HPV antibody. Thus, the one or more papillomavirus proteins present in the cell lysate solution recognized and bound by the second anti-HPV antibody flow laterally on the solid surface of the strip of the rapid test device in order to form into a complex with the first anti-HPV antibody.

As still another example, the solid surface can be a surface of a rapid test strip, such as a membrane surface of a vertical flow through device. One or more anti-HPV antibodies can be coated/immobilized on the solid surface of the membrane of a vertical flow-through rapid test device to detect the complex of the anti-HPV antibodies with the one or more papillomavirus proteins present in the cell lysate solution. Alternatively, two anti-HPV antibodies can be used with a first anti-HPV antibody coated on the solid surface of the membrane before adding the cell lysate solution and a second anti-HPV antibody onto the membrane of the vertical flow rapid test device to form a complex with the first anti-HPV antibody.

As still another example, the solid surface can be inside a surface of a microfluidic device. Various testing samples in fluidic cell lysate solutions are designed to flow inside one or more channels of the microfluidic device. One or more anti-HPV antibodies can be coated/immobilized on the solid surface inside the channels of the microfluidic device to bind to the one or more papillomavirus proteins present in the fluidic cell lysate testing solution and form a complex. Also, two anti-HPV antibodies can be used in a microfluidic device to bind to the one or more papillomavirus proteins present in the cell lysate solution of a testing sample and be circulated inside the channels of the microfluidic device.

In one aspect, one or more papillomavirus proteins present in the cell lysate solution are coated on the solid surface before reacting with the anti-HPV antibody. For example, direct detection of the papillomavirus proteins can be obtained by adding a pre-labeled anti-HPV antibody capable of binding to the one or more papillomavirus proteins to detect the formation of the anti-HPV antibody-papillomavirus protein complex. The pre-labeled anti-HPV antibody can be labeled with a detection agent, including but not limited to, horse radish peroxidase conjugate, biotin, gold particle, fluorescent, and combinations thereof. Alternatively, the anti-HPV antibody-papillomavirus protein complex can be recognized by adding a pre-labeled secondary antibody capable of binding to the anti-HPV antibody. The secondary antibody can be labeled with a detection agent to detect the formation of the anti-HPV antibody-papillomavirus protein complex by binding to the anti-HPV antibody. In one example, proteins from cell lysate solution are coated on the solid surface of a membrane blot or a microtiter plate device before reacting with the anti-HPV antibody.

In another aspect, the anti-HPV antibody is coated on the solid surface before reacting with the one or more papillomavirus proteins present in the cell lysate solution to detect papillomavirus infection of the human subject. For example, direct detection of the papillomavirus proteins can be obtained by adding an anti-HPV antibody pre-coated on the solid surface and pre-labeled with a detection agent to detect the formation of the anti-HPV antibody-papillomavirus protein complex. Alternatively, the anti-HPV antibody can be pre-coated on the solid surface without pre-labeling and a secondary antibody capable of binding to the anti-HPV antibody can be added later to detect the formation of the anti-HPV antibody-papillomavirus protein complex.

In another aspect, the anti-cellular protein antibody is coated on the solid surface before reacting with one or more cellular proteins present in the cell lysate solution of the clinical sample to detect the presence of the cellular protein. These cellular proteins may include any of the HPV related cellular proteins that are affected inside a human subject after HPV infection, such as p16INK4a, p53, p63, Rb, pRb, p21WAF1, ki67 (MIB-1), MYC cellular oncogene, cyclin proteins (e.g., cyclin A, cyclin B, cyclin E), CDKN2A/p16INK4a, telomerase (e.g., TERC), replication complex proteins, MCM5, CDC6, topoisomerase II alpha (TOP2A), MCM2, survivine, minichromosome maintenance proteins (e.g., minichromosome maintenance protein 2, minichromosome maintenance protein 4, and minichromosome maintenance protein 5), and combinations thereof.

The expression levels of the cellular proteins and the expression level of the papillomavirus viral proteins in the clinical sample of the human subject are compared to detect the presence of the HPV infection and/or a disease stage of HPV infection (early infection, late infection, etc.). For example, in high grade CIN lesions, E6 and E7 are strongly expressed in host basal epithelial cells and interfere substantially with the cell cycle of its host cells. Expression of HPV oncoproteins interferes with G1-S-Phase regulation in host cells. The HPV E6 and E7 proteins target a plethora of cellular interactions, such as the inactivation of pRB by E7 and the degradation of p53 by E6. High levels of HPV E7 proteins inactivate pRB and lead to disruption of E2F-Rb binding. Usually, binding of pRB to E2F blocks E2F driven cell cycle activation. In replicating cells, E2F is regulated by phosphorylation of RB. Rb phosphorylation is normally mediated by cyclin dependent kinases (CDK4, CDK6) that are controlled by several kinase inhibitors (INKS).

As a result of the loss of Rb/E2F repression and the strong activation by free E2F, the expression of a host cell protein, p16INK4a, is strongly overexpressed. In addition, S-phase genes are continuously activated since the p16INK4a mediated repression of Cdk4/6 has no downstream effect on pRb host cell protein. Since E7-dependent E2F release is not mediated by phosphorylation of pRb, the counter-regulatory p16INK4a expression has no effect on the activated cell cycle. Under physiological conditions p16INK4a is expressed when cells undergo a genomic stress situation such as substantial shortening of telomeres in ageing tissues. Also, apoptosis is abrogated by HPV E6 mediated degradation of p53. The overexpression of the cyclin dependent kinase (CDK) inhibitor, p16INK4a, is a direct consequence of deregulated HPV oncogene expression.

In addition, host cell proteins important for proliferation and host cell genome replication may be overexpressed as a result of HPV infection. These host cell proteins include, ki67 (MIB-1), MYC cellular oncogene, Cyclin proteins (e.g., cyclin A, B, E, etc.), CDKN2A/p16INK4a, telomerase (e.g., TERC), replication complex proteins (e.g., MCM5, CDC6, topoisomerase II alpha (TOP2A), MCM2, minichromosome maintenance proteins 2, 4, and 5, etc.).

Other host cell proteins affected by HPV infection may include host cellular stress and invasion proteins, such as heat shock protein (e.g., $HSP_{40}$, $HSP_{60}$, $HSP_{70}$), carbonic anhydrase (e.g, CA9/MN antigen). Also, host cell proteins that enhance viral oncogene activity can be affected by HPV infection and these proteins include TSLC1, DAPK1, RARB, TWIST1, brn-3s transcription factor, among others. In addition, survivin protein which is involved in cell cycle and apoptosis regulation can be affected by HPV infection. The expression of VEGF can be upregulated by HPV E6 protein, which is independent from E6 mediated p53 degradation.

Accordingly, examples of host cell proteins whose expression levels may be altered by HPV infection include, but are not limited to, p16INK4a, cyclin dependent kinase inhibitors, pRB, p53, E2F, E2F activated cell cycle proteins, cyclin dependent kinases, CDK4, CDK6, S-phase genes, Ki-67 (MIB-1), MYC protein, cyclin-A, cyclin-B, cyclin-E, telomerase-TERC, MCM2 protein, TOP2A protein, heat shock protein 40 ($HSP_{40}$), heat shock protein 60 ($HSP_{60}$), heat shock protein 70 ($HSP_{70}$), CA9/MN protein, laminin 5, laminin proteins, brn-3a, CDK N2 protein, topoisomerase 2A, microsome maintenance proteins-2, microsome maintenance proteins-4, microsome maintenance proteins-5, survivin protein, VEGF protein, p27 (kip1) protein, p21 (waf) protein, and combinations thereof.

Changes in the expression levels of among these proteins affected by HPV infection (e.g., E6, E7, p53, Rb, p16INK4a, among others) serve as a signature for high risk of contracting cervical cancer. Elevated levels of HPV-associated viral proteins, viral antigens, and host cells proteins (e.g., E6 proteins, E7 proteins, p16INK4a, E2F, Ki-67 (MIB-1), MYC protein, CDK4, cyclin-A, cyclin-B, cyclin-E, telomerase-TERC, MCM2 protein, TOP2A protein, heat shock protein 40 ($HSP_{40}$), heat shock protein 60 ($HSP_{60}$), heat shock protein 70 ($HSP_{70}$), CA9/MN protein, laminin 5, laminin proteins, brn-3a, CDK N2 protein, topoisomerase 2A, microsome maintenance proteins-2, microsome maintenance proteins-4, microsome maintenance proteins-5, survivin protein, VEGF protein), and reduced levels of host cell proteins (e.g., p53, RB, p27(kip1), and p21 (waf), etc.) confirm not just HPV infection but also that the subjects are at high risk of contracting cervical cancer. On the contrary, unchanged levels of p53 and RB in the human subjects with elevated levels of HPV-associated viral proteins or antigens may indicate a general HPV infection and cervical cancer not yet progressed.

As an example, the immunological assays for detection of HPV protein, such as E6, E7, L1, etc., or immune response thereof due to HPV infection can be performed in high throughput ELISA screening assays, rapid immunological screening assays, and additional multiplexed protein chip assays, etc., and combinations thereof to assay the expression levels of the HPV viral proteins and/or many of the HPV interfering cellular proteins.

The anti-HPV antibody or the anti-cellular protein antibody can be coated on any of the solid surface of any immunological detecting devices/kits as described herein to be used in an immunological assay for detecting the presence of the HPV viral proteins or the cellular proteins in a testing sample. For example, the anti-HPV antibody can be coated on the surface of a bead, the surface of a strip, the surface of a rapid test strip, the surface of a membrane, the membrane surface of a vertical flow through device, the surface of a microfluidic device, the surface of a blot membrane, the surface of a protein chip, a glass surface, and the bottom surface of a microtiterplate. For example, the anti-HPV antibody can be coated on the solid surface of a protein chip device before reacting with the cell lysate solution. The anti-HPV antibody or a secondary antibody capable of binding to the anti-HPV antibody is pre-labeled with a detection agent in order to detect the complex of the anti-HPV antibody and the papillomavirus proteins present in the cell lysate solution on the solid surface of a protein chip device. As another example, the anti-HPV antibody can be coated on the solid surface of a microtiter plate or a rapid test device before reacting with the cell lysate solution. The rapid test device may be a lateral flow rapid test device, a vertical flow-through rapid test device, a microfluidic rapid test device, or any other rapid test devices.

In another embodiment, more than one anti-HPV antibodies can be used in a sandwiched format to detect the presence of one or more papillomavirus proteins from one or more papillomavirus types present in a biological sample that has been processed into a cell lysate solution. The detection of the one or more papillomavirus proteins is obtained by forming a complex of a sandwich of two or more anti-HPV antibodies with the testing papillomavirus proteins. A first anti-HPV antibody and a second anti-HPV antibody are used, both are generated against recombinant HPV proteins, and used to react with the cell lysate solution such that the second anti-HPV antibody is able to bind and detect one or more papillomavirus proteins in the cell lysate solution captured by the first anti-HPV antibody. In one aspect, the cell lysate solution is added to react with the first anti-HPV antibody before reacting with the second anti-HPV antibody. In another aspect, the cell lysate solution is pre-mixed with the second anti-HPV antibody before reacting with the first anti-HPV antibody.

In one aspect, the second anti-HPV antibody is pre-labeled with a detection agent, which may be, for example, a horse radish peroxidase conjugant, biotin, gold particle, and fluorescent agents. In another aspect, the cell lysate solution is pre-mixed with the second anti-HPV antibody and the second anti-HPV antibody is pre-labeled with a detection agent. In another aspect, a secondary antibody capable of binding to the first or the second anti-HPV antibody is pre-labeled with a detection agent.

Accordingly, a complex of one or more papillomavirus proteins with the first and the second anti-HPV antibody formed on the solid surface can be detected for the presence of the one or more papillomavirus proteins in the biological sample. As an example, the complex of anti-HPV antibodies-papillomavirus proteins is detected on the solid surface of one or more beads and the complex is detected by FACS (Fluorescence-activated cell sorting). As another example, the complex is detected on the solid surface of a strip of a rapid test device with the first anti-HPV antibody immobilized on one end of the strip, where the second anti-HPV antibody and the cell lysate solution are added onto the other end of the strip before flowing laterally across the solid surface of the strip of the rapid test device to form a complex with first anti-HPV antibody. As yet another example, the complex is detected on the solid surface of a membrane of a vertical flow-through rapid test device with the first anti-HPV antibody immobilized thereon, and wherein the cell lysate solution and the second anti-HPV antibody are added sequentially onto the solid surface of the membrane of the vertical flow rapid test device to form a complex with first anti-HPV antibody. As another example, the complex can be detected on the solid surface of a microfluidic device, and the complex is flowing through the microfluidic device. As another example, the complex is detected on the solid surface of the bottom of a microtiter plate.

Various formats can be used to detect the anti-HPV antibody-papillomavirus proteins complex by using a pre-labeled detection agent. For example, a detection agent, such as a horse radish peroxidase conjugant, biotin, gold particle, and fluorescent agents, can be pre-labeled on various agents, proteins and antibodies. For example, the detection agent can be pre-labeled on the anti-HPV antibody, the various proteins present in the cell lysate solution, a secondary antibody that binds to the anti-HPV antibody, or a second anti-HPV antibody different from the anti-HPV antibody to be detected. The secondary antibody can be an anti-mouse antibody if the primary anti-HPV antibody is a mouse antibody. The secondary antibody may also be an anti-rabbit antibody if the primary anti-HPV antibody is a rabbit antibody. The secondary antibody can be an anti-goat antibody if the primary anti-HPV antibody is a goat antibody.

The presence or levels of the detection agent prelabeled on proteins or antibodies as described herein can be qualitatively or quantitatively measured. For example, a direct qualitative visualization of the color change of a detection agent prelabeled on a anti-HPV antibody or proteins present in cell lysate solution can be performed in a lateral or vertical rapid test assays. A pre-labeled detection agent can also be used to react with its suitable substrate reagents such that positive reaction between the detecting agent and its substrates can be detected through readout by an ELISA reader. Another example of a detection agent suitable for pre-labeling is a detection agent capable of being detected by a microarray scanner after a positive binding reaction when the solid surface is the glass or membrane of a protein chip device.

Both polyclonal and monoclonal anti-HPV antibodies can be used in the immunological assays having a solid surface for coating an anti-HPV antibody or various testing samples. Useful monoclonal antibodies obtained include specific monoclonal antibodies with binding reactivity for a single HPV protein, and general pan antibodies with binding reactivity for more than one HPV proteins or more than one HPV type (high risk and/or low risk).

The antibodies as developed herein lend themselves to the high quality and properly purified recombinant proteins encoded by HPV early and late genes. They are useful in immunological assays to generate very high sensitivity and specificity for screening HPV infection and cervical cancer detection. The purified recombinant papillomavirus proteins may include, but are not limited to, papillomavirus E6 protein, papillomavirus E7 protein, papillomavirus L1 protein, and combinations thereof. The recombinant papillomavirus proteins include, but are not limited to, recombinant HPV-16 E6 proteins, recombinant HPV-16 E7 proteins, recombinant HPV-18 E6 proteins, recombinant HPV-18 E7 proteins, recombinant HPV-16 L1 proteins, and recombinant HPV-18 L1 proteins.

Various monoclonal antibodies against HPV viral proteins are provided such that infection by high risk and low risk HPV types can be detected by a single monoclonal antibody. The invention also provides HPV type specific monoclonal antibodies for detecting only the high risk HPV types. The one or more papillomavirus types include high risk HPV types, low risk HPV types, HPV-16, HPV-18, HPV-31, HPV-33, HPV-35, HPV-39, HPV-45, HPV-51, HPV-52, HPV-56, HPV-58, HPV-59, and HPV-68, HPV-6, HPV-11, HPV-42, HPV-43, HPV-44, HPV-53, HPV-54, HPV-55, and HPV-56, and combinations thereof.

One embodiment of the invention provides one or more anti-HPV antibodies capable of binding to two or more HPV viral proteins from the same HPV type. Another embodiment, of the invention provides one or more anti-HPV antibody is antibodies capable of binding to two or more HPV viral proteins from different HPV types. For example, the invention provides a monoclonal antibody capable of recognizing a common epitope on E6 protein from two different HPV types, both HPV16 and HPV18 by screening antibody-producing hybridoma cells with a purified HPV16 E6 recombinant protein and a purified HPV18 E6 recombinant protein. Another example provides a monoclonal antibody that recognizes a common epitope on HPV16 E7 and HPV18 E7 proteins. Still another embodiment of the invention provides a monoclonal antibody that recognizes a common epitope on HPV16 E6, HPV16 E7, HPV16 L1, HPV18 E6, and HPV18 E7 proteins.

As another example, a monoclonal antibody capable of recognizing a specific epitope on only one HPV viral protein, but not another HPV viral protein, is obtained by screening antibody-producing hybridoma cells with a first purified recombinant papillomavirus protein from a first HPV type and a second purified recombinant papillomavirus protein from a second HPV type, wherein the first and second viral proteins correspond to the first and the second purified recombinant papillomavirus proteins of the first and second HPV types.

In one embodiment, a method of detecting papillomavirus infection in a human subject includes obtaining a clinical or biological sample from the human subject, and conducting one or more immunological assays on the clinical sample from the human subject using various HPV recombinant proteins and lab-generated antibodies specific for HPV oncoproteins in order to detect and screen for the presence of HPV infection from the presence of HPV proteins and HPV antibodies in the human subject. The biological sample includes, but is not limited to, cervical cells, cervical tissues, cervical swabs, body fluids, serum, blood, tumors, cell cultures, biopsies, and combination thereof, wherein the biological sample is obtained from the general population for routine screening of cervical cancer.

In another embodiment, the HPV proteins in the human subject are detected using one or more antibodies raised against HPV recombinant proteins, including, but not limited to, various polyclonal and monoclonal antibodies against various HPV early and late proteins. One antibody among the one or more antibodies is capable of recognizing a common epitope present on two or more papillomavirus proteins. The two or more papillomavirus proteins may include a papillomavirus early protein and a late papillomavirus protein and the antibody is capable of recognizing both the papillomavirus early protein and the late papillomavirus protein. The antibodies obtained include antibodies recognizing HPV E6 proteins, antibodies recognizing HPV E7 proteins, antibodies recognizing HPV E6 and E7 proteins, antibodies recognizing HPV L1 proteins, antibodies recognizing HPV E6 proteins from different HPV types, antibodies recognizing HPV E7 proteins from different HPV types, antibodies recognizing HPV L1 proteins from different HPV types, antibodies recognizing HPV E6 and E7 proteins of the same HPV types, antibodies recognizing HPV E6 and E7 proteins of different HPV types, and antibodies recognizing HPV E6, E7, and L1 proteins.

The antibodies can be used for one or more immunological assays, including, but not limited to, ELISA (enzyme linked immunoabsorbant assays), antigen assays for papillomavirus proteins, antibody assays for antibodies against papillomavirus proteins, assays for papillomavirus immunocomplexes, protein chip assays, radioimmunoprecipitation assays, rapid membrane immunochromatographic assays, rapid stick immunochromatographic assays, immunohistochemistry for tissues and/or cervical cells, and immunocytological assays followed by flow cytolmetry, among others. In one embodiment, the one or more immunological assays may be non-invasive with minimal or no additional instrument required.

A cytological papanicolaou smear (Pap smear) assay may also be performed on a clinical sample to compare the results of the cytological papanicolaou smear assay with the results of the immunocytological assays. In addition, nucleic acid hybridization assays can also be performed on the clinical sample to detect the presence of a papillomavirus genome in the clinical sample from the human subject. The nucleic acid hybridization assays may include, but are not limited to polymerase chain reactions, nucleic acid hybridization assays, DNA chip assays, radioactive nucleic acid hybridization and detection assays, and non-radioactive nucleic acid hybridization and detection assays.

In another embodiment, the immunological assay is used to detect a disease stage caused by HPV infection. The disease stage may be, for example, an early stage HPV infection, a late stage HPV infection, an early stage cervical cell lesion, a late stage cervical cell lesion, low grade of squamous intraepithelial lesion (LSIL), high grade of squamous intraepithelial lesion (HSIL), atypical squamous cells of undetermined significance (ASCUS), cervical intraneoplasm stage 1, 2, 3 (CIN1, CIN2, CIN3, respectively), developed cervical cancer, adenocarcinoma, or squamous cell carcinoma (SCC).

The basic techniques for conducting the immunological assays can be found in "Antibodies: A Laboratory Manual", Harlow and Lane, Cold Spring Harbor Laboratory, Cold Spring Harbor, N.Y. 1989; "Molecular Cloning", A Laboratory Manual, eds. Sambrook, Fritsch and Maniatis, Cold Spring Harbor Laboratory Press, 1989, and others books and manuals known in the art. The related immunological assays, immunohistochemistry for tissues and/or cervical cells, and/or immunocytological assays followed by flow cytometry can also be found in co-pending U.S. patent applications: Ser. No. 11/559,366, filed on Nov. 13, 2006, titled "Detection method for human papillomavirus (HPV) and its application in cervical cancer"; Ser. No. 12/082,740, filed Apr. 14, 2008, titled "Protein chips for HPV detection"; Ser. No. 61/131,991, filed Jun. 13, 2008 titled "Antibodies and assays for HPV detection"; Ser. No. 61/192,912 Filed on Sep. 22, 2008, titled "Novel monoclonal antibodies against HPV proteins useful for early stage and late stage detection, screening, and diagnosis of HPV related cervical cancer"; Ser. No. 12/456,053 (NEOD/0004), filed concurrently as this application, titled "Novel monoclonal antibodies against HPV proteins"; serial number 12,456/054 (NEOD/0005.01), filed concurrently as this application, titled "in situ detection of early stages and late stages HPV infection"; Ser. No. 12/456,055 (NEOD/0005.02), filed concurrently as this application, titled "in situ detection of early stages and late stages HPV infection". All of the above referenced applications are herein incorporated by reference.

The invention also provides various methods, detection assays, and kits, polyclonal and monoclonal antibodies, polypeptides, recombinant proteins, and nucleic acids useful for detecting general HPV infection as well as infection by various HPV genotypes, high risk HPVs and low risk HPVs. In addition, the assays or sample formats in detecting the presence of HPV proteins are not limited and can be used for cervical tissues, cervical cells, cervical scrapes, serum, body fluids, etc. The useful screening or diagnosing assay can be IHC, ICC, flow cytometry, antibodies coupled to beads, rapid tests, protein chips, dot blots, slots, as well a conventional ELISA assay. HPV proteins can be detected by the antibodies of the invention to be present in epithelium tissue as evidenced by IHC staining after scoring by a pathologist.

For example, a lateral flow through rapid test device having a solid surface of a strip membrane is provided. The solid surface may include a first anti-HPV antibody immobilized on one end of the strip and a second anti-HPV antibody parked on the other end of the strip able to react with a cell lysate solution processed from a biological sample. The device may be conveniently performed in one step for detecting the presence of one or more papillomavirus proteins from one or more papillomavirus types in the biological sample. The second anti-HPV antibody parked on the other end of the strip will form into a complex with HPV proteins present in the cell lysate and then flow across the surface of the strip on the rapid test device. As the complex containing the HPV proteins flow across toward the other end of the strip, it can then be captured by the first anti-HPV antibody on the surface of the strip.

In operation, as an example, clinical samples collected from liquid based solution were processed, washed, centrifuged, and lysed with lysis buffer to obtain cell lysate containing the one or more papillomavirus proteins. The cell lysate was added onto the top of the strip device from one end containing an anti-HPV detecting antibody, conjugated with gold particles to react with the one or more papillomavirus, and flowed through to the other end of the strip device, wherein an anti-HPV pre-coated on the surface captured the immunocomplex of the flow through containing the one or more papillomavirus proteins bound to the anti-HPV detecting antibody, and an agent showed a pink band when the complex was captured and retained on the surface, demonstrating a positive reaction of the one-step lateral flow through assay for detection of HPV proteins. A test control was also included in the device. The test control includes coating one protein on the surface of one end, which is for example, 0.5 cm away from the surface where the anti-HPV antibody is coated, to capture its binding protein which is pre-labeled with agent and flows through with the testing sample. For the test control protein selected, there is no cross binding activity or interference with the testing protein for binding to anti-HPV antibody. Therefore, there are two lines showing pink bands to demonstrate positive results, and there is only one line showing a pink band on the test control position to demonstrate negative results of the assay.

As another example, a vertical flow-through rapid test device for detecting the presence of one or more papillomavirus proteins from one or more papillomavirus types in a biological sample is also provided. The vertical flow-through rapid test device may include a solid surface of a membrane, a first anti-HPV antibody, and a second anti-HPV antibody. The first anti-HPV antibody is immobilized on the solid surface to react with a cell lysate solution processed from the biological sample. The second anti-HPV antibody and the cell lysate solution are added onto the surface of the membrane, flow vertically through the solid surface, and form a complex with first anti-HPV antibody on the solid surface of the membrane. The first and the second anti-HPV antibodies are generated against recombinant proteins encoded by one or more papillomavirus genes such that the anti-HPV antibodies are able to bind and detect the one or more papillomavirus proteins in the cell lysate solution.

The surface of the flow through device can be coated with one or more strips or spots of one, two, or more anti-HPV antibodies to detect one, two, or more HPV proteins present in the biological samples on the same device. This flow through assay may take multiple steps including the adding of testing protein, adding of detecting antibody and substrate, and washing between each step, or it may take two steps by premixing the testing protein with the detecting antibody which is prelabeled with agent, followed by reacting with colometric substrate to show results. It may take only one step as in a lateral flow through assay format but in a device for vertical flowthrough. The dot blot assay described in this invention may be formatted to fit into the vertical flow through device. The assay gives results within about 10 min, about 30 min, or less than an hour, and thus is suitable for use of point of care in a doctor's office. The second anti-HPV antibody may be pre-labeled with gold particles such that the complex captured on the surface of the device can be detected by its color. High intensity of color indicates the presence of the one or more papillomavirus proteins in the biological samples and can be read out by naked eye or by an instrument.

As still another example, a microfluidic rapid test device for detecting the presence of one or more papillomavirus proteins from one or more papillomavirus types in a biological sample is also provided. The microfluidic rapid test device may include a solid surface bound with a first anti-HPV antibody and a second anti-HPV antibody. A microfluidic device has one or more channels with at least one dimension less than 1 mm. Common fluids used in microfluidic devices include whole blood samples, bacterial cell suspensions, protein or antibody solutions and various buffers. The use of microfluidic devices to conduct biomedical research and create clinically useful technologies has a number of significant advantages. First, because the volume of fluids within these channels is very small, usually several nanoliters, the amount of reagents and analytes used is quite small. This is especially significant for expensive reagents. The fabrication techniques used to construct microfluidic devices are relatively inexpensive and are very amenable both to highly elaborate, multiplexed devices and also to mass production. In a manner similar to that for microelectronics, microfluidic technologies enable the fabrication of highly integrated devices for performing several different functions on the same substrate chip. Ultimately, the microfluidics device is to create integrated, portable clinical diagnostic devices for home and bedside use, thereby eliminating time consuming laboratory analysis procedures.

Another example is a device for performing a beads immunological assay. The device may include beads coated with antibody that bind and capture the protein of interest followed by a detecting antibody with a labeled agent able to be detected by FACS. It may also include a lysis buffer to lyse the cells to obtain protein to bind on the beads and react with the detecting antibody.

Still another example is a device for performing a dot blot immunological assay. The device may include a membrane with an absorbing pad underneath, similar to vertical flow through device, where the cell lysate containing testing protein can be spotted directly onto a very small area of the surface to allow highly concentrated protein to be retained on the surface, followed by binding detecting antibody to HPV protein on the surface of the membrane. A colormetric substrate reacts with the detecting antibody and shows a color spot demonstrating a positive reaction of the assay.

Yet another example is a device for performing a protein chip assay. The device may include a slide with a glass or membrane surface pre-spotted with various antibodies specific to various proteins of interest including HPV proteins and host cellular proteins. It may also include lysis buffer to lyse the cells to obtain the proteins of interest. It may also include labeling reagent to directly label the cell lysate, or label a second antibody detecting the proteins of interest.

In operation for a protein chip assay, the surface on which proteins are coated/bound may be, for example, a surface-chemistry treated glass or membrane, which can covalently or non-covalently bind with capture agents or proteins thereto. A spotting machine with fine pins dipped with capture agents, such as the recombinant proteins, antigens, antibodies, or other proteins in suitable buffers is generally used to facilitate binding of such proteins or antibodies to the treated surface. Like other surfaces described in the microtiter plate format, the spotted and thus captured proteins or antibodies bind strongly to the surface-chemistry treated surface of a protein chip and remain on the treated surface to allow the interaction and specific binding of the captured proteins with target proteins, antibodies, or antigens, even after several washings of removing non-specific binding, to be detected with a detection system conjugated with Cy3 or Cy5. The detection of specific interactions is obtained and measured by the fluorescent intensities of the spotted/dipped images via a microarray scanner.

As an example, antibody microarray can be used as the protein chips assay format for detection of HPV protein and other cellular proteins. First, cells, samples or cultured cells to be tested were collected, centrifuged, washed, and lysed to generate cell lysate as analyte. The protein in the cell lysate was quantitated and labeled with biotin or Cy3, Cy5 or any other chromagen for subsequent detection of the binding of the labeled protein on the surface of prespotted antibody. The surface of the protein chips for the protein chip assays can be a membrane or glass for different analysis and quantification techniques.

Various novel monoclonal antibodies against HPV proteins, identified as useful biomarkers and useful tools for detecting HPV viral proteins, HPV oncoproteins, early screening of cervical cancer, and diagnosing CIN and/or invasive cervical and other cancers, are provided. The tools of the inventions can also be used in early clinical screening for HPV infection and general diagnosis for cervical cancer and other cancers, specific detection of invasive cervical cancer, detection of other HPV related cancers, early stage precancerous lesions as well as late stage cancer progression.

The antibodies described in this invention provide a tool to detect HPV proteins present in various sources of biological samples. The biological samples includes, but are not limited to, cervical cells, cervical tissues, cervical swabs, body fluids, serum, blood, tumors, cell cultures, biopsies, and combinations thereof, wherein the biological sample is obtained from a group of people from the general population for routine screening of cervical cancer.

As an example, the antibodies described herein can be used as a capture antibody to coat on microtiterplate and/or used as a detection antibody in a sandwich format of ELISA (Enzyme Linked Immuno Sandwich Assay). Antibodies can be selected based on the specificity described herein of a monoclonal antibody to particular HPV proteins or HPV types, or in combinations thereof. The detection antibody with selected specificity to the monoclonal antibodies described herein can be directly conjugated with a label like biotin, alkaline phosphatase, HRP, fluorescent, etc., followed by colormetric, chemiluminescent or fluorescent substrate for readout. The detection antibody can also be a polyclonal antibody described herein and be followed by a secondary antibody conjugated with a label like biotin, alkaline phosphatase, HRP, fluorescent, etc. A combination of using polyclonal and monoclonal antibodies for the sandwich ELISA as capture and detection antibodies or vice versa, increases assay sensitivity by incorporating secondary antibody to amplify the signal for detection. For direct EIA (Enzyme Immuno Assay), cells, samples or cultured cells to be tested were collected and lysed to generate cell lysate as analyte. The protein in the cell lysate was quantitated and coated to a microtiterplate using the same amount of protein in each well followed by the detection antibody with specificity described in this invention.

Detection of HPV DNAs, genomes, early viral proteins, late viral proteins, oncoproteins, and/or capsid proteins from various HPV genotypes can be performed by various in vitro and in vivo methods and detection assays according to "Antibodies: A Laboratory Manual", Harlow and Lane, Cold Spring Harbor Laboratory, Cold Spring Harbor, N.Y. 1989; "Molecular Cloning", A Laboratory Manual, eds. Sambrook, Fritsch and Maniatis, Cold Spring Harbor Laboratory Press, 1989, and others books and manuals and can be very useful in general clinical screening for HPV infection.

Detection of HPV antibodies and/or oncoproteins by immunological assays can be used in early clinical screening for HPV infection and general diagnosis for cervical cancer and can be performed in a single rapid test or in a multiplexed test. Comparative detection of altered levels of HPV proteins and host proteins can be performed in the same or different assays. It can also be used in diagnosing HPV-associated carcinomas of the uterine cervix, as well as those cases associated with epithelial cell abnormalities induced by HPV infection, pre-malignant and malignant HPV-associated epithelial cell lesions, and those at risk of developing HPV-associated cervical carcinoma and adenocarcinoma. The methods as described herein can be used independently or as an adjunct screening tool to convention cytological papanicolaou smear tests or histological tests and the results thereof can be compared for follow-up patient management.

EXAMPLES

A. Detecting HPV Proteins from Biological Samples Using One Anti-HPV Antibody
1. Direct EIA: One or More HPV Proteins Coated on Microtiterplate to be Detected by One or More Anti-HPV Antibodies Clinical samples from cervical scrapes were obtained for detection of HPV E6, E7 or L1 proteins on direct EIA. Cervical cells from various sample sources included cervical scrape cells in liquid based cytology solution, cervical scrape cells in transport medium (used for HPV DNA test sample), or cervical scrape cells in lysis buffer. To perform the direct EIA described herein, specimens were processed, centrifuged, washed, and lysed to generate cell lysate as analyte. The proteins in the cell lysate were quantitated and coated to a microtiterplate with the same amount of protein in each well. The plate was blocked, and detected by each HPV monoclonal antibody followed by HRP-conjugated secondary antibody (anti-mouse IgG or anti-rabbit IgG for example). TMB substrate was added followed by a stopping solution. OD at 450 nm was taken by an ELISA plate reader.

As an example, cervical cells from various stages of cervical neoplasm collected in liquid based solution were processed to obtain the cell lysate for detection of HPV DNA and HPV proteins. For HPV DNA detection, touchdown PCR protocol was used. For HPV protein detection by direct EIA, cell lysate was coated directly on the microtiterplate, blocked, then specific HPV antibodies were used followed by a secondary antibody conjugated with HRP. OD450 was taken from a microtiter plate coated with cell lysate with or without adding the primary HPV antibody followed by the secondary antibody. Since various proteins from the cell lysate were coated on the microplate, OD from each sample with no primary HPV antibody was considered to be the non-specific binding of the cell lysate with the secondary antibody. To obtain OD for specific binding of HPV protein with anti-HPV antibody, net OD for each sample obtained by subtraction of the OD from its non-specific binding of the secondary antibody was considered to be the specific binding of HPV protein with the primary anti-HPV antibody. Net OD from each PCR negative sample was obtained. Mean OD from PCR negative samples was used as the baseline of the assay. Samples with net OD over two folds of average OD from PCR negative samples were considered positive, otherwise they were negative for the EIA test described herein.

TABLE 1

Detection of HPV DNA and HPV protein from liquid based cervical scrapes

| Liquid based cervical scrapes | | | |
|---|---|---|---|
| Sample No. | Dx or pap smear results | HPV DNA by PCR | Direct EIA by poly anti-E7 |
| 1 | ASCUS | pos | pos |
| 2 | ASC-H | pos | pos |
| 3 | ASCUS | pos | pos |
| 4 | ASCUS | neg | pos |
| 5 | ASCUS | neg | neg |
| 6 | CIN1 | pos | pos |
| 7 | CIN1 | pos | pos |
| 8 | CIN1 | pos | pos |
| 9 | CIN1 | pos | neg |
| 10 | CIN1/ASCUS | neg | pos |
| 11 | CIN1 | neg | neg |
| 12 | CIN2 | pos | neg |
| 13 | CIN2 | pos | neg |
| 14 | CIN2 | neg | neg |
| 15 | CIN2 | neg | neg |
| 16 | CIN3 | pos | pos |
| 17 | CIN3 | pos | pos |
| 18 | CIN3 | pos | pos |
| 19 | CIN3 | neg | neg |
| 20 | CIN3 | neg | neg |
| 21 | CIN3 | neg | neg |
| 22 | SCC | pos | pos |
| 23 | SCC | pos | pos |
| 24 | AD | neg | neg |

As an example, clinical samples diagnosed by histology or pap smear staining including abnormal cells, ASCUS, CIN1, CIN2, CIN3, SCC and Adenocarcinoma are obtained and processed into cell lysate for direct coating on a microtiterplate. Detection of HPV DNA by PCR and detection of HPV proteins by EIA are shown as Table 1 and compared with the clinical diagnosis and pap smear results. Data show 79% (19 out of 24) correlation of HPV DNA with HPV proteins detected by polyclonal anti-E7 antibody. For those HPV DNA and HPV proteins not in correlation (21%; 5 out of 24), 3 are PCR pos, EIA negative (case No. 9/CIN1, No. 12/CIN2, and No. 13/CIN2) indicating HPV infection with no expression or non-detectable E7 oncoproteins. For those that are PCR negative, EIA positive like case No. 4 (ASCUS), and No. 10 (CIN1/ASCUS), it could be false negative of PCR, or E7 oncoproteins could be expressed with loss of HPV DNA.

For those HPV DNA positive but HPV EIA negative samples, the HPV DNA assay may be false positive, or there may be positive HPV DNA detection with no expression of HPV oncogenic proteins. These data indicate that HPV EIA described herein has relevance for the screening of cervical cancer. It's important to detect the HPV oncoproteins to follow up if progression of dysplasia HSIL occurs. These data indicate that the HPV oncoproteins are good biomarkers for screening and early detection of cervical cancers, and other HPV associated cancers. For cases that are both PCR and EIA negative but diagnosed ASCUS, or CIN, the loss of HPV DNA and HPV oncoprotein detection is possibly due to the sampling of cervical scrape cells or treatment of the patients, or false positive of the pap smear results. However, more samples should be tested.

2. Dot Blot Assay: Spotting Cell Lysate on Membrane to Detect HPV Proteins from Biological Samples Using One or More Anti-HPV Antibodies To develop a rapid test showing results with no instrument required for the read out, a dot blot assay demonstrates the feasibility of detecting HPV proteins from cell lysate on a membrane with visual results followed by colormetric substrate. As an example, cervical cells from various stage of cervical neoplasm collected in liquid based solution are processed to obtain the cell lysate to be spotted on a membrane. The membrane was air dried prior to blocking the blot with blocking solution. An anti-HPV antibody was added to react with the blot followed by a secondary antibody capable of binding to the anti-HPV antibody. The blot was washed between each step to avoid non-specific binding of the antibody onto the membrane. In the final step, TMB substrate was added to the blot and the appearance of a blue dot indicated a positive reaction of the cell lysate binding with the anti-HPV antibody used in this dot blot assay. Recombinant HPV proteins were also spotted on the membrane to be used as positive or negative control.

FIG. 1 shows the results of a dot blot detecting HPV L1 proteins using a mouse monoclonal anti-HPV L1 antibody. As indicated, dots from the first row are cell lysate from various SCC cervical scrapes in liquid based solution and dots from the second row are recombinant HPV1 6 L1 protein at concentrations of 20, 2, 0.2 and 0 µg/ml from left to the right as indicated A, B, C, D respectively. As the results indicated in the second row of the blot, recombinant HPV L1 proteins reacts highly positive to 0.2 µg/ml or lower of purified recombinant proteins with the mouse monoclonal anti-HPV L1 antibody used in FIG. 1. These data demonstrate that HPV L1 proteins from both recombinant HPV 16 L1 and cell lysate can be detected by dot blot assay using a mouse monoclonal anti-HPV L1 antibody as shown in FIG. 1.

FIG. 2 show results of another dot blot detecting HPV L1 proteins using the same mouse monoclonal anti-HPV L1 antibody shown in FIG. 1. As indicated, dots from the first and second row are cell lysate from various SCC cervical scrapes in liquid based solution. In the third row of the blot, recombinant HPV16 E6, HPV18 E6, HPV16 E7, HPV18 E7, HPV16 L1 proteins are spotted from left to right as indicated A, B, C, D, and E, respectively. As the results in the third row of the blot indicate, recombinant HPV L1 protein, spotted on 3E, reacts positively with the mouse monoclonal anti-HPV L1 antibody used in the assay, compared to HPV16 E7 and HPV16 E6 with no detectable spot or HPV18 E7 and HPV18 E6 with very weak spot shown on the third row of the blot. The weak spots were likely due to the non-specific binding of the assay. Thus when considering them as the background of the assay, clinical samples 2C and 2E have equally strong spot signal compared to that from HPV16 L1 recombinant protein. These data indicate that HPV L1 proteins from both recombinant HPV 16 L1 and cell lysate can be detected by dot blot assay using a mouse monoclonal anti-HPV L1 antibody demonstrated in FIG. 1.

To detect HPV E6 protein on dot blot assay, FIG. 3 shows results of a dot blot with a mouse monoclonal anti-HPV E6 antibody. As indicated, dots from the first row are cell lysate from various SCC cervical scrapes (same as the first row of FIG. 1) in liquid based solution and dots from the second row are recombinant HPV16 E6 protein at concentrations of 20, 2, 0.2 and 0 µg/ml from left to the right as indicated A, B, C, D respectively. As the results in the second row of the blot indicate, recombinant HPV E6 proteins react positively to 20, and 2 µg/ml, and weakly to 0.2 µg/ml or lower of purified recombinant proteins with the mouse monoclonal anti-HPV E6 antibody used in FIG. 3. These data indicate that HPV E6 proteins from both recombinant HPV 16 E6 and cell lysate can be detected by dot blot assay using a mouse monoclonal anti-HPV E6 antibody demonstrated in FIG. 3.

The same spotting blot shown in FIG. 2 was also used to demonstrate detection of HPV E6 protein on dot blot assay. FIG. 4 shows results of a dot blot detecting HPV E6 proteins using the same mouse monoclonal anti-HPV E6 antibody shown in FIG. 3. As the results in the third row of the blot indicate, recombinant HPV16 E6 proteins on spot 3A react positively with the mouse monoclonal anti-HPV16 E6 antibody used in the assay, compared to HPV 18 E6 with very weak spot and other recombinant proteins with no detectable spots shown on the third row of FIG. 2. These results demonstrate the specificity of HPV E6 proteins with the mouse monoclonal anti-HPV E6 antibody, with no cross reacting with HPV L1 or HPV E7 proteins. Using the weak spot corresponding to background or cross-reactive binding of HPV 18 E6 in the assay, samples 2C and 2E show very strong spots compared to others with moderate spots and 2D with no detectable spot. These data indicate 70% (7 out of 10) clinical samples containing HPV E6 proteins can be detected by dot blot assay using a mouse monoclonal anti-HPV16 E6 antibody demonstrated in FIG. 4.

To demonstrate detection of HPV E7 proteins on dot blot assay, the same spotting blot shown in FIG. 2 and FIG. 4 was also used to blot with a mouse monoclonal anti-HPV E7 antibody detecting HPV E7 proteins as shown in FIG. 5. As the results in the third row of the blot in FIG. 5 indicate, recombinant HPV18 E7 proteins, spotted on 3D, react positively with the mouse monoclonal anti-HPV18 E7 antibody used in the assay, compared to other HPV recombinant proteins with no detectable spots, or a very weak spot with HPV16 L1 on spot 3E shown on the third row of FIG. 2. These results demonstrate specificity of HPV E7 proteins with the mouse monoclonal anti-HPV E7 antibody and has no cross reaction with HPV L1, or HPV E6 proteins. Using the weak spot corresponding to background or cross-reactive binding of HPV 18 E7 in the assay, samples 2C and 2E show very strong spots compared to others with no detectable spots. These data indicate samples 2C and 2E containing HPV18 E7 proteins can be detected by dot blot assay using a mouse monoclonal anti-HPV18 E7 antibody as demonstrated in FIG. 5.

3. Antibody Microarray: Spotting Antibodies on a Protein Chip to Detect HPV Proteins and Cellular Endogenous Proteins in a Labeled Cell Lysate from Biological Sample For example, in a protein chip assay, the surface for proteins to be coated/bound to may be, for example, a glass or membrane surface that is chemistry treated, which can covalently or non-covalently bind or coat with capture agents or proteins thereto. A spotting machine with fine pins dipped with capture agents, such as the recombinant proteins, antigens, antibodies, or other proteins in suitable buffers is generally used to facilitate the binding of such proteins or antibodies to the treated surface. Like other surfaces described in the microtiter plate format, the spotted and thus captured proteins or antibodies bind strongly to the chemistry treated surface of a protein chip and remain on the treated surface to allow the interaction and specific binding of the captured proteins with target proteins, antibodies, or antigens, even after several washings of removing non-specific binding, to be detected with a detection system conjugated with Cy3 or Cy5. The detection of specific interactions is obtained and measured by the fluorescent intensities of the spotted/dipped images via a microarray scanner.

As an example, an antibody microarray can be used in the protein chips assay format for detection of HPV protein and other cellular proteins. First, cells, samples or cultured cells to be tested were collected, centrifuged, washed, and lysed to generate cell lysate as analyte. The protein in the cell lysate was quantitated and labeled with biotin or Cy3, Cy5 or any other chromagen for subsequent binding and detection of the labeled protein on the surface of prespotted antibody. The surface of the protein chips for the protein chip assays can be a membrane or glass for different analysis and quantification techniques.

Figure 8:
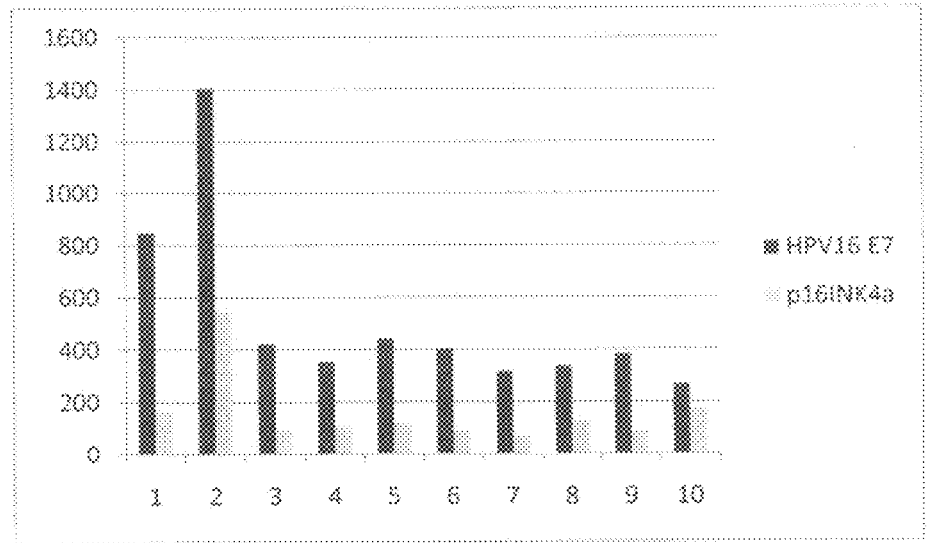
FIG. 8 is another graph showing the fluorescent intensity results of the antibody microarray assay for each of the 10 cell lysate samples as shown in FIG. 6 to detect HPV E7 proteins and cellular p16 INK4a proteins according to another embodiment of the invention.

Table 2 shows the results of protein chip assays for detecting the presence of various HPV proteins and various host cellular proteins. An antibody array pre-spotted with antibodies against HPV and various cellular proteins was used to detect the presence of these HPV proteins and host cellular proteins in a human cervical scrape clinical sample. A total of 10 samples of cervical scrapes (labeled as S1-S10 shown on Table 2) diagnosed as keratinizing squamous cell carcinoma (grade 2 or grade 3) in liquid based solution was processed and lysed to generate protein lysate with proper labeling (such as biotin label) for subsequent detection (followed by strepavidin-Cy3, for example). The fluorescent intensity indicating binding of the proteins from the human sample with prespotted antibody against proteins including, but not limited to, HPV-16 E7, HPV-16 L1, p63, p53, p21WAF1, p16INK4a, phosphorylated Rb, and unphosphorylated Rb, was obtained and is shown in Table 2. Fluorescent intensity for the binding of the specific protein with the specific antibody prespotted on the microarray indicated changes in the expression levels of these proteins affected by HPV infection and is shown in FIG. 6 to FIG. 12.

as p53, or Rb which directly interact with HPV oncoproteins or cellular proteins such as p16, p21, etc., affected by HPV infection. P16INK4a has been commonly used as a surrogate for detection of cervical cancer. To demonstrate HPV viral proteins, such as E6 or E7 oncoprotein, can serve as a better biomarker for detecting cervical cancer, the antibody microarray (protein chip assay) described herein demonstrates detection of multiple proteins including various HPV proteins and various cellular proteins simultaneously. FIG. 8 shows detection and comparison of HPV E7 and p16 protein expression in the 10 SCC samples. Fluorescent intensity from each individual sample (1 through 10) demonstrates binding of HPV16E7 antibody and p16INK4a antibody with proteins expressed in cell lysate from cervical cancer patients on antibody microarray. For the 10 samples tested, each sample shows higher fluorescent intensity with HPV E7 antibody than p16 antibody, indicating more HPVE7 protein expressed compared to p16. These data suggest HPVE7 serves as a better marker for detecting cervical cancer.

Figure 9:
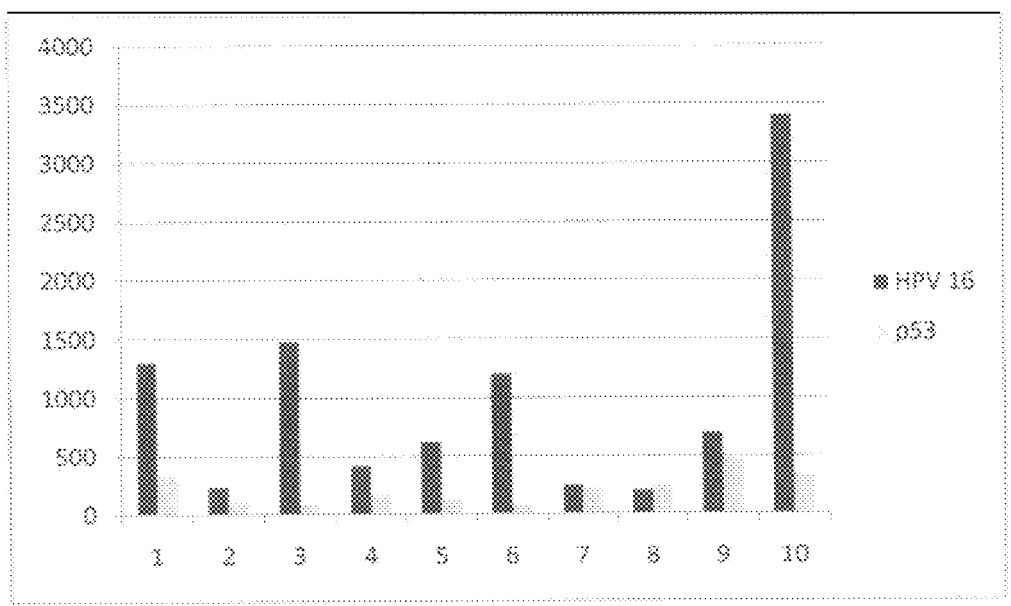
FIG. 9 is another graph showing the fluorescent intensity results of the antibody microarray assay for each of the 10 cell lysate samples as shown in FIG. 6 to detect HPV L1 proteins and cellular p53 proteins according to another embodiment of the invention.

To demonstrate p53 affected by HPV in cervical cancer, FIG. 9 shows fluorescent intensity for both HPV16 and p53 antibody, indicating overexpression of HPV16 with p53 suppression in clinical samples with HPV infection. Comparing expression of HPV16 and p53, the results indicate p53 is

TABLE 2

Flourescent intensity (after background subtraction) of individual spot shows binding of specific antibody with proteins expressed in cell lysate from cervical cancer patients on antibody microarray

| Ab spotted | S1 | S2 | S3 | S4 | S5 | S6 | S7 | S8 | S9 | S10 |
|---|---|---|---|---|---|---|---|---|---|---|
| HPV16 E7 | 849 | 1407 | 422 | 355 | 443 | 403 | 316 | 337 | 383 | 267 |
| HPV 16 | 1309 | 236 | 1477 | 418 | 620 | 1206 | 251 | 205 | 700 | 3407 |
| p63 | 398 | 128 | 205 | 51 | 167 | 146 | 215 | 230 | 427 | 174 |
| p53 | 325 | 102 | 86 | 161 | 119 | 83 | 226 | 242 | 465 | 335 |
| P21WAF1 | 594 | 100 | 130 | 92 | 167 | 54 | 177 | 178 | 493 | 250 |
| p16INK4a | 164 | 549 | 97 | 107 | 116 | 87 | 72 | 128 | 87 | 174 |
| Retinoblastoma | 753 | 170 | 140 | 185 | 109 | 70 | 219 | 247 | 448 | 317 |
| Rb (phosph) | 491 | 236 | 269 | 143 | 238 | 245 | 156 | 224 | 310 | 171 |

To compare the expression of each protein from the 10 SCC samples tested, the average of the fluorescent intensity for a specific protein from each sample was obtained to demonstrate the protein expression level with standard deviation bar for the graphs in FIG. 6. The results indicate various HPV proteins and various cellular endogenous proteins from the cell lysates of the 10 cervical scrape samples can be detected on the antibody microarray assay described herein. As indicated in FIG. 6, HPV 16 and HPV16E7 are over expressed compared to other cellular proteins.

Figure 7:
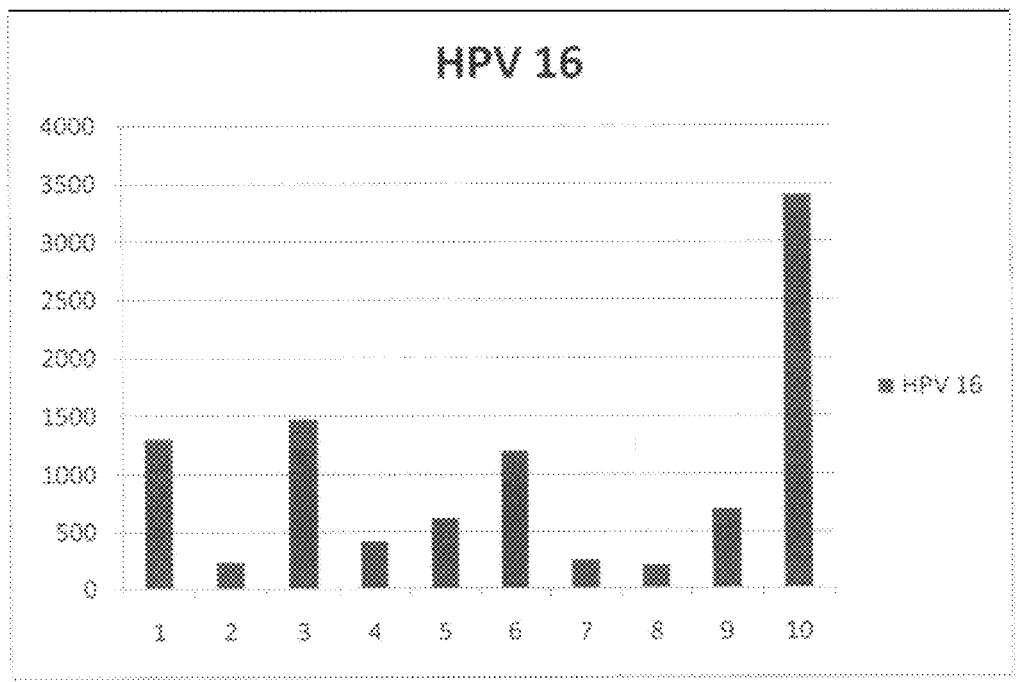
FIG. 7 is another graph showing the fluorescent intensity results of the antibody microarray assay for each of the 10 cell lysate samples as shown in FIG. 6 to detect HPV L1 proteins according to another embodiment of the invention.

To demonstrate variation of HPV16 in different samples, FIG. 7 shows the fluorescent intensity of each sample for detecting HPV L1 proteins in cell lysate from the cervical scrape cells shown in FIG. 6. The results demonstrate binding of HPV16 antibody (anti-HPV L1 antibody) with HPV proteins, particularly the L1 viral protein expressed in cell lysate from cervical cancer patients, on antibody microarray. HPV16 L1 proteins are expressed predominantly in sample S1, S3, S6, and S10, medium for sample S4, S5, and S9 while expression is low in sample S2, S7, and S8 which might be due to a different type of HPV not recognized by the HPV16 antibody used in this assay.

HPV E6 and E7 proteins play critical roles in the oncogenesis of HPV in cervical cancer. To study the interaction of the HPV E6 E7 oncoproteins with cellular proteins, the antibody microarray assay described herein provides tools for simultaneous detection of HPV proteins and cellular proteins such expressed at much lower level with high level of HPV16 expression in most clinical samples except clinical samples S7 and S8, which might be a different type of HPV other than HPV 16 infection. However, low p53 expression in all clinical samples indicates most p53 proteins are degraded by HPV E6 oncoproteins during cervical cancer development.

Figure 10:
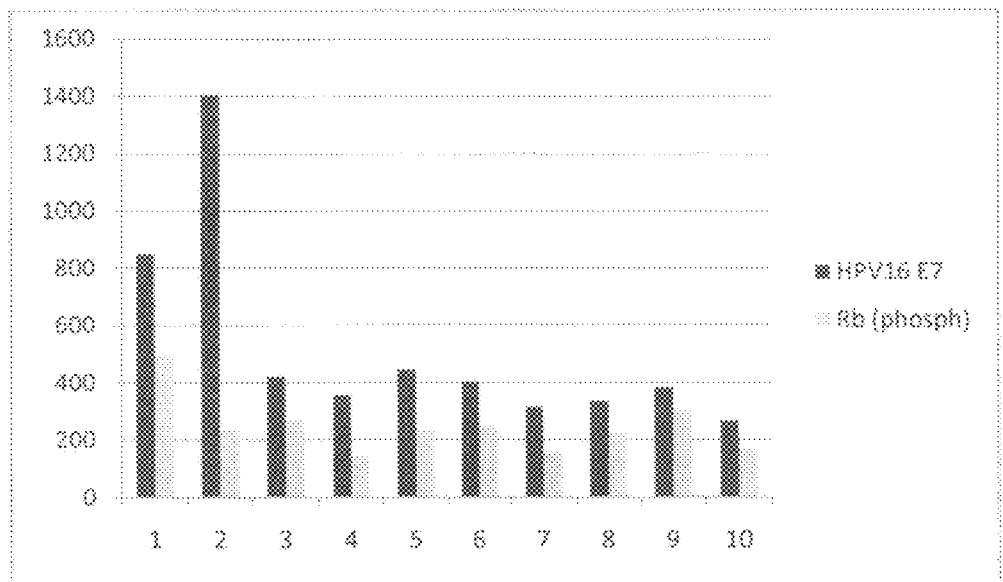
FIG. 10 is another graph showing the fluorescent intensity results of the antibody microarray assay for each of the 10 cell lysate samples as shown in FIG. 6 to detect HPV E7 proteins and cellular phosphate form of Rb proteins according to another embodiment of the invention.

To demonstrate interaction of E7 and retinoblastoma (Rb) protein and phosphorylated Rb affected by HPV in cervical cancer, FIG. 10 shows fluorescent intensity for HPV16E7 and pRb antibody, indicating HPV16 E7 expression at higher level while Rb is inactivated, which is recognized by anti-Rb-phosphate specific antibody at lower level. In sample S2, there is overexpression of HPV16 E7 and suppression of phosphorylated Rb. Data indicate inactivation of Rb (low in reacting with Rb-phosphate antibody) by E7 pathway causes malignant transformation developing cervical cancer.

Figure 11:
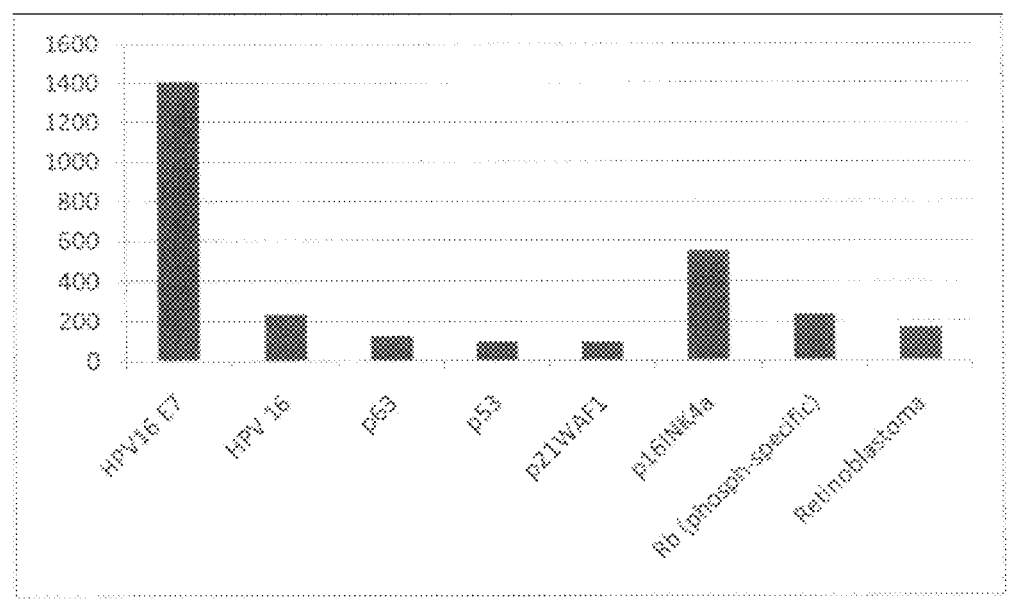
FIG. 11 is another graph showing the fluorescent intensity results of the antibody microarray assay for sample S2.

To demonstrate expression profiling of protein chip assay for cervical cancer as an example, FIG. 11 shows expression profiling of the selected HPV proteins and cellular proteins for sample S2. Results indicate HPV E7 and p16 were overexpressed, while other cellular proteins were suppressed. All together with results from FIG. 8, FIG. 10, and FIG. 11 suggest overexpression of HPV E7 protein in sample #2 inactivates Rb and induces p16INK4a expression, resulting in malignant transformation and the development of cervical cancer. Sample S1 with high HPV-E7 expression level may undergo pathway independent from Rb, thus didn't express a high level of p16INK4a.

Figure 12:
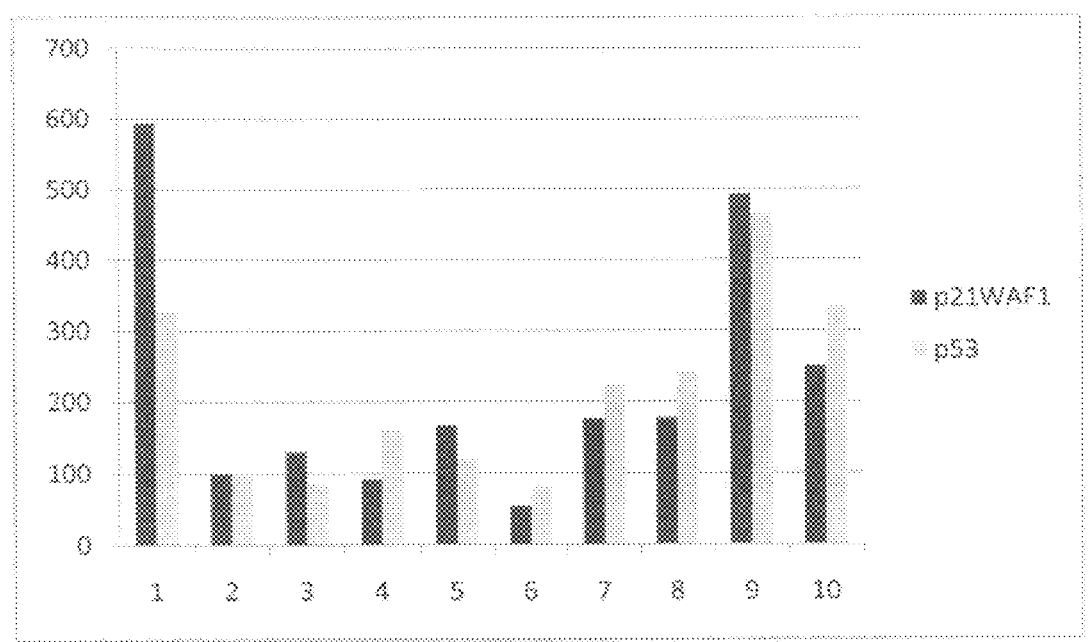
FIG. 12 is another graph showing the fluorescent intensity results of the antibody microarray assay for each of the 10 cell lysate samples as shown in FIG. 6 to detect cellular p21 WAF1 and p53 proteins according to another embodiment of the invention.

To demonstrate another cellular protein p21 WAF1 expression in cervical cancer and its correlation with p53, FIG. 12 shows fluorescent intensity of each sample for detecting cellular p21 WAF1 and p53 proteins using cell lysate from cervical scrape cells. As data in FIG. 12 shows, 9 out of 10 samples (except sample S1) p21WAF1 that is well correlated with expression of p53. These data demonstrate degradation of tumor suppressor p53 by HPV-E6 pathway through p21WAF1 inhibition causes malignant transformation for cervical cancer development.

Protein chip assays provide tools to detect HPV proteins as well as cellular protein induced and/or inhibited by HPV infection in malignant of cancer development. Study results using protein chip assay described in the invention indicate that patients with cervical cancer in this study adopt various pathways, thus progress differently. This technology applies to other HPV associated cancers to predict the pathways involved in malignance. An algorithm can be developed to predict the signature of all proteins involved in the pathways during cancer development. Thus, recommendation of specific treatment for personalized medicine can be provided.

B. Detection of HPV Proteins in Biological Samples Using a First Anti-HPV Antibody and a Second Anti-HPV Antibody as the Capture Antibody and the Detection Antibody in a Sandwich Assay As an example, an antigen sandwich assay involves coating a first antibody, such as a capture antibody or a spotting antibody, having an affinity for binding to an antigen of interest, on a surface, such as bottom surfaces of a protein chip, a membrane and/or a microtiter plate, etc. The antigen of interest may be, for example, a papillomavirus protein, an oncoprotein, a capsid protein, which may be encoded by a HPV viral gene, e.g., an early gene or a late gene, etc. After blocking unbound portions on the surface, the clinical sample to be analyzed can be applied to bind with the capture antibody to form an immunocomplex, which can be detected by a second antibody or a detection antibody by binding to the antigen of interest. Hence, the first and the second antibodies or the pair of the capture antibody and the detection antibody interact with the antigen of interest, much like a sandwich. The capture or spotting antibody can be the same or different antibody as the detection antibody, as long as the two antibodies can specifically bind to the antigen of interest, e.g., a HPV viral protein, a HPV oncoprotein, a capsid protein, among others.

Next, the sandwiched bound antibody-antigen complex can be detected by a secondary antibody, which has an affinity for the detection antibody and facilitates measurement by a standard immunological complex detection system using colormetric, chemiluminescent, fluorescent and many different kinds of substrates. The final readouts or visualizations can be performed by an instrument with appropriate light absorbance readers or directly visualized by eye and compared to a control sample. Positive results indicate binding of the antigen of interest to the primary antibodies, the capture antibody, and the detection antibody, and thus the presence of the antigen of interest in the clinical sample. On the contrary, negative results indicate no binding of the antigen of interest to the primary antibodies and thus the absence of the antigen of interest in the clinical sample.

1. ELISA: Coating First Anti-HPV Antibody on Microtiterplate to Detect HPV Proteins by a Second Anti-HPV Antibody To demonstrate a sandwich ELISA on microtiter plate, serum diagnosed with SCC or HPV PCR pos or HPV PCR neg was diluted and used as the analyte for the detection of HPV E6, E7, or L1 protein present in the serum sample. The assay format is demonstrated herein as the ELISA sandwich assay using rabbit polyclonal antibody for E6, E7, or L1 protein as the coating antibody or the first anti-HPV antibody followed by analyte (serum) and its corresponding second anti-HPV antibody detected by another antibody conjugated with HRP. After incubation with substrate and stopper, OD 450 was taken by a microtiter plate reader. As an example shown in FIG. 13, the results demonstrate an ELISA detecting HPV E6, E7 and L1 protein in human serum sample diagnosed with SCC (squamous cell carcinoma) or HPV positive (by PCR) compared to a HPV negative serum (by PCR) using rabbit polyclonal anti-HPV antibody for coating and detection.

Figure 13:
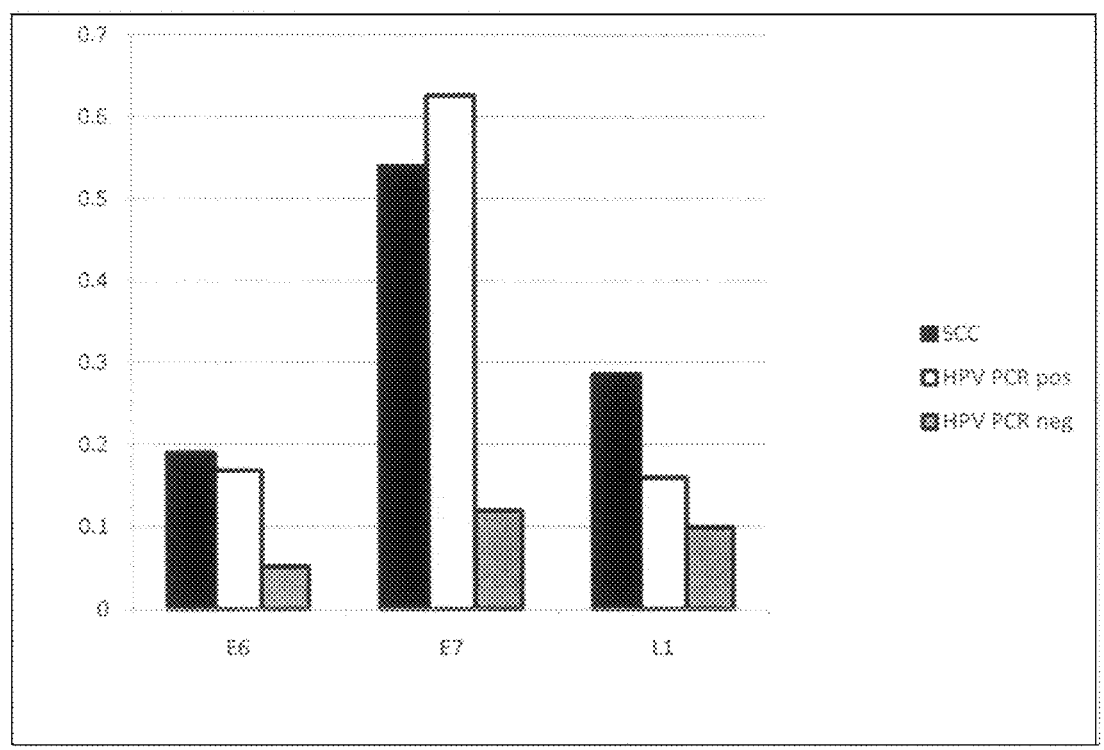
FIG. 13 shows the results of an ELISA assay to detect HPV E6, E7 and L1 proteins in human serum samples diagnosed as SCC (squamous cell carcinoma) or HPV positive (by PCR) as compared to a HPV negative serum sample (by PCR) using anti-HPV rabbit polyclonal antibody for coating and detection according to another embodiment of the invention.

FIG. 13 demonstrates the presence of the E6, E7 oncoproteins, and L1 viral proteins can be detected in serum from patients diagnosed with SCC or HPV PCR positive samples using serum from HPV PCR negative samples as a control. The data indicate that E7 is the predominant protein detected from serum compared to E6, or L1. Both SCC and HPV PCR pos samples have predominant E6 and E7 protein expression compared to the serum from PCR neg sample. It's noted that SCC has predominant L1 detection compared to HPV PCR neg serum, while HPV PCR pos sample did not have predominant L1 expression compared to HPV PCR neg sample. However, expression of L1 protein is not as predominant as E6, or E7 in either case. These data indicate expression of L1 may be present or absent in the serum depending on the stage and/or cycles of viral infection. However, detection of oncoproteins E6, or E7 in serum from both SCC and HPV PCR pos sample suggests that E6 or E7 represents a better marker for HPV detection in serum. This is the first report for detection of E6, E7 oncoproteins from serum. More serum samples needed to be analyzed.

2. Flow Beads Assay: Coating First Anti-HPV Antibody on Beads to Detect HPV Proteins by a Second Anti-HPV Antibody As an example, a first anti-HPV antibody coated on the surface of the beads reacts with HPV proteins in cell lysate of biological sample, forming a complex on the surface of the beads to capture a second anti-HPV antibody. The complex can be detected directly when the second anti-HPV antibody is pre-labeled, or can be detected by adding a pre-labeled antibody capable of binding to the second anti-HPV antibody. The pre-labeled antibody can be labeled with a detection agent including, but not limited to, horse radish peroxidase conjugate, biotin, gold particle, fluorescent, and combinations thereof. As an example, the complex present on the solid surface of beads can be detected by FACS (Fluorescence-activated cell sorting) using anti-mouse or anti-rabbit PE as the secondary antibody. When multiple HPV proteins are captured on the beads, multiple second anti-HPV antibodies labeled by different fluorescent dye can be detected simultaneously by the FACS. Thus, the beads assay by FACS provides powerful multiplex assay for detection of one or more HPV proteins from biological samples.

Figure 14:
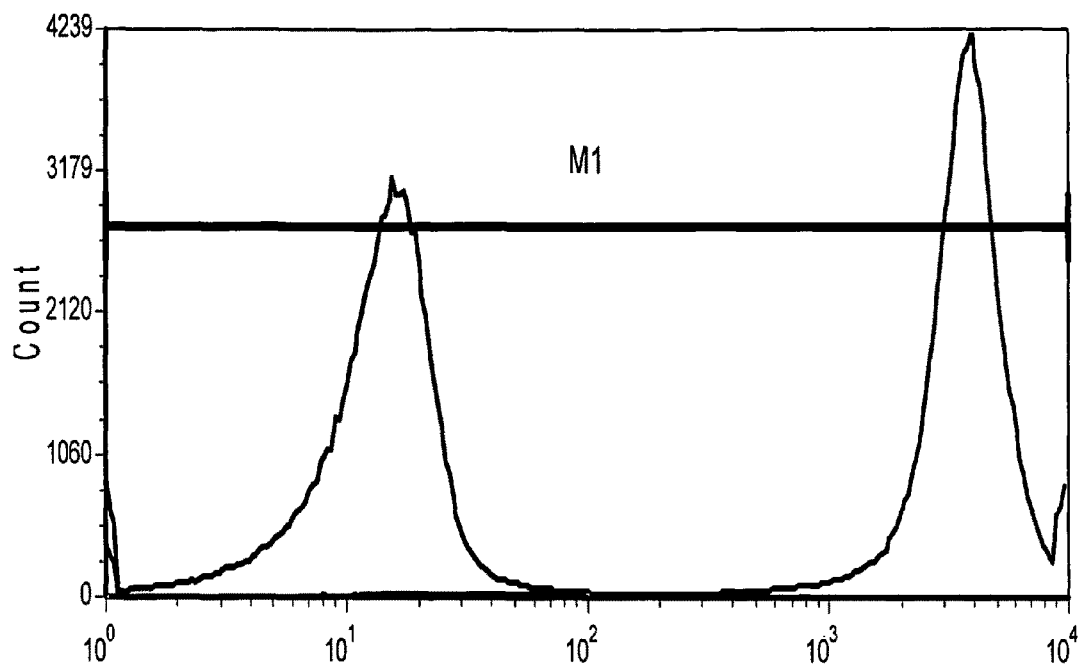
FIG. 14 shows the results of a sandwich beads assay by FACS to detect recombinant HPV16 L1 protein using an anti-HPV16 L1 mouse monoclonal antibody as coating antibody and an anti-HPV16 L1 rabbit polyclonal antibody as detecting antibody.

To demonstrate the beads assay described herein can be used for detection of various HPV proteins, various antibodies against HPV E6, HPV E7 and HPV L1 were used as the coating and detecting antibody to detect HPV E6, HPV E7, and HPV L1 proteins. FIG. 14-FIG. 17 show results of beads assay detecting HPV 16 L1, HPV 16E6, HPV 18 E6, and HPV 16E7 protein, respectively, by FACS. As an example, FIG. 14 shows results of a sandwich beads assay by FACS to detect recombinant HPV16L1 protein using a rabbit polyclonal anti-HPV16 L1 antibody as coating antibody and a mouse monoclonal anti-HPV16 L1 antibody as detecting antibody followed by a secondary antibody, anti-mouse conjugated with PE agent. As data indicated, sample containing purified recombinant HPV 16 L1 protein, which is captured on the surface of the beads to be detected by FACS, shows a discrete peak with higher fluorescent PE (the peak on the right in FIG. 14) than sample containing buffer as a negative control of the assay (the peak on the left in FIG. 14). Results indicate about 250 fold differences in fluorescence between the sample containing the specific detecting protein (geometric mean about 2958) and the control sample (geometric mean about 12) with no detecting protein present. These data suggest this beads format provides dynamic range of assays allowed to detect various amount of HPV L1 proteins present in the clinical samples.

Figure 15:
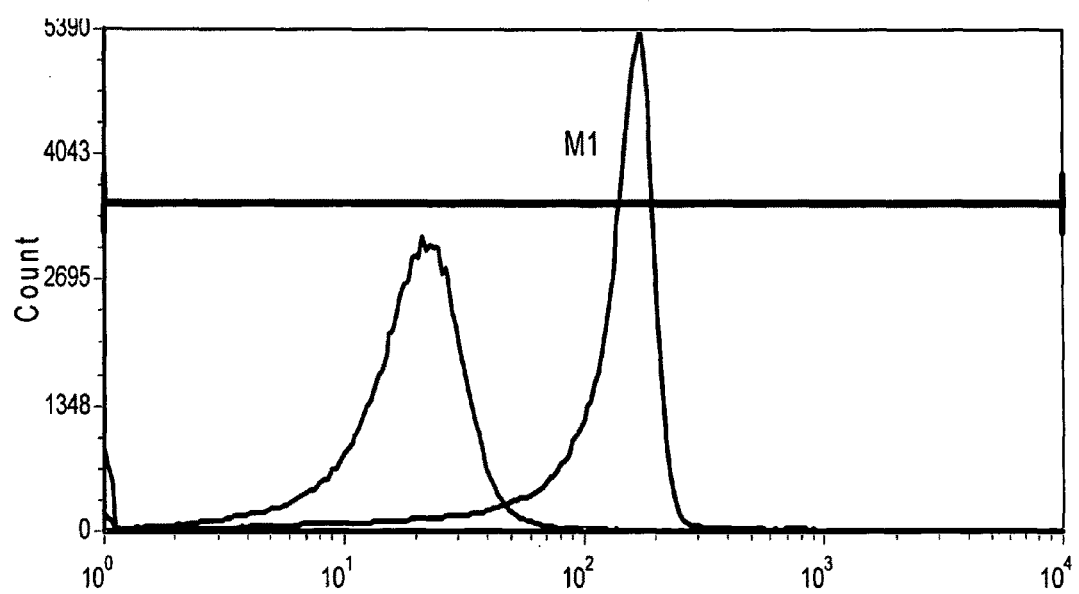
FIG. 15 shows the results of a sandwich beads assay by FACS to detect recombinant HPV16 E6 protein using an anti-HPV16 E6 mouse monoclonal antibody as coating antibody and an anti-HPV16 E6 rabbit polyclonal antibody as detecting antibody.

As an another example, FIG. 15 shows results of a sandwich beads assay by FACS to detect recombinant HPV16E6 protein using a rabbit polyclonal anti-HPV16 E6 antibody as coating antibody and a mouse monoclonal anti-HPV16 E6 antibody as detecting antibody followed by a secondary antibody, anti-mouse conjugated with PE agent. As data has indicated, sample containing purified recombinant HPV 16 E6 protein which is captured on the surface of the beads to be detected by FACS shows a discrete peak with higher fluorescent PE (the peak on the right in FIG. 15) than sample containing buffer as a negative control of the assay (the peak on the left in FIG. 15). Results indicate about a 7 fold difference in fluorescence between the sample containing the specific detecting protein (geometric mean about 114) and the control sample (geometric mean about 17) with no detecting protein present. These data suggest this beads format provides dynamic range of assays allowed to detect various amounts of HPV E6 proteins present in the clinical samples.

Figure 16:
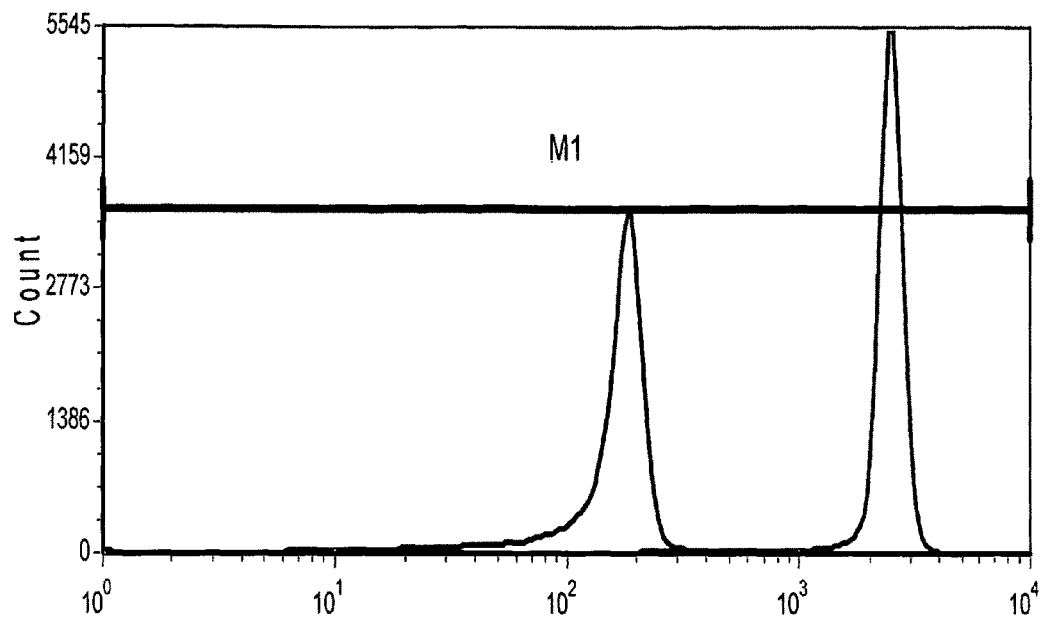
FIG. 16 shows the results of a sandwich beads assay by FACS to detect recombinant HPV18 E6 protein using an anti-HPV18 E6 mouse monoclonal antibody as coating antibody and an anti-HPV18 E6 rabbit polyclonal antibody as detecting antibody.

FIG. 16 shows results of a sandwich beads assay by FACS to detect recombinant HPV16L1 protein using a rabbit polyclonal anti-HPV18 E6 antibody as coating antibody and a mouse monoclonal anti-HPV18 E6 antibody as detecting antibody followed by a secondary antibody, anti-mouse conjugated with PE agent. As the data has indicated, sample containing purified recombinant HPV 18 E6 protein which is captured on the surface of the beads to be detected by FACS shows a discrete peak with higher fluorescent PE (the peak on the right in FIG. 16) than sample containing buffer as a negative control of the assay (the peak on the left in FIG. 16). Results indicate about a 15 fold difference in fluorescence between the sample containing the specific detecting protein (geometric mean about 2294) and the control sample (geometric mean about 148) with no detecting protein present. These data suggest this beads format provides dynamic range of assays allowed to detect various amounts of HPV 18E6 proteins present in the clinical samples.

Figure 17:
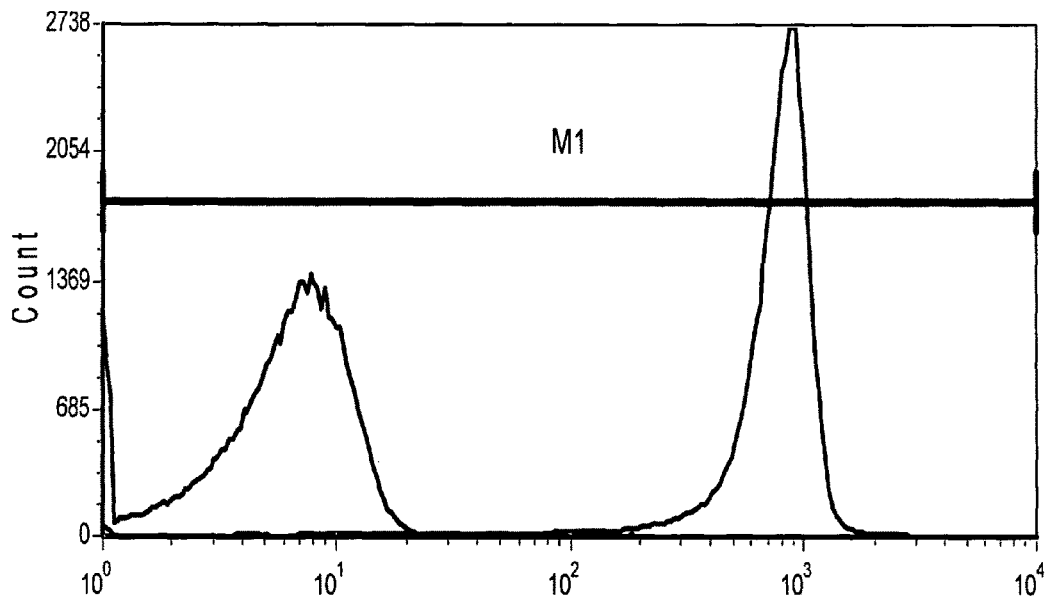
FIG. 17 shows the results of a sandwich beads assay by FACS to detect recombinant HPV16 E7 protein using an anti-HPV16 E7 mouse monoclonal antibody as coating antibody and an anti-HPV16 E7 rabbit polyclonal antibody as detecting antibody.

FIG. 17 shows results of a sandwich beads assay by FACS to detect recombinant HPV16 E7 protein using a rabbit polyclonal anti-HPV16 E7 antibody as coating antibody and a mouse monoclonal anti-HPV16 E7 antibody as detecting antibody followed by a secondary antibody, anti-mouse conjugated with PE agent. As the data has indicated, sample containing purified recombinant HPV 16 E7 protein which is captured on the surface of the beads to be detected by FACS shows a discrete peak with higher fluorescent PE (the peak on the right in FIG. 17) from sample containing buffer as a negative control of the assay (the peak on the left in FIG. 17). Results indicate about a 122 fold difference in fluorescence between the sample containing the specific detecting protein (geometric mean about 673) and the control sample (geometric mean about 5.5) with no detecting protein present. These data suggest this beads format provides dynamic range of assays allowed to detect various amounts of HPV16 E7 proteins present in the clinical samples.

Figure 18:
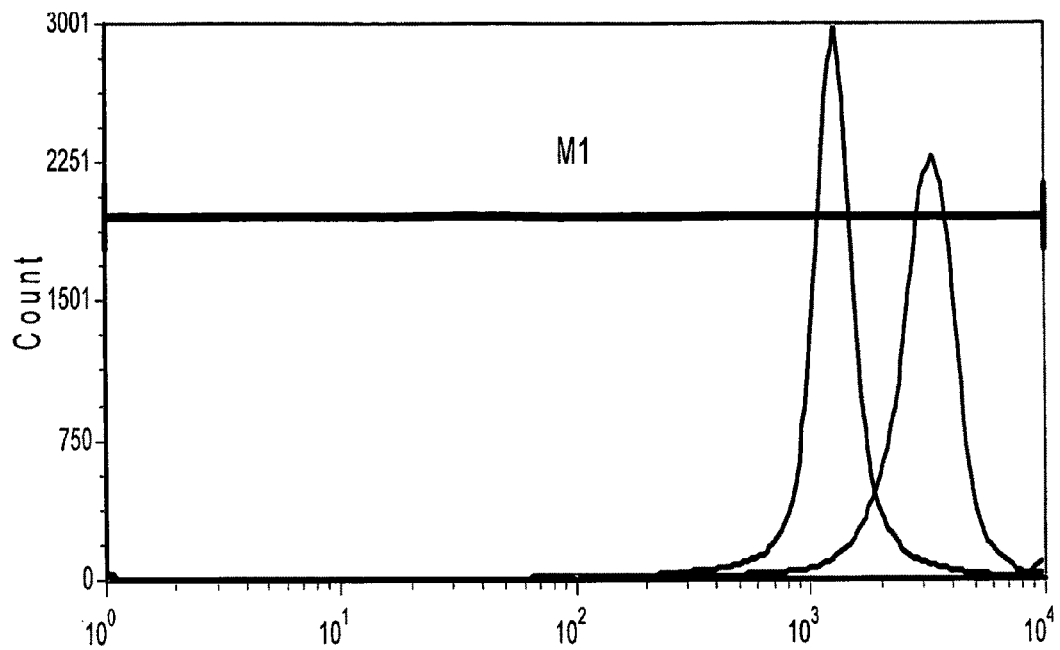
FIG. 18 shows the results of a sandwich beads assay by FACS to detect recombinant HPV16 E6 protein using an anti-HPV16 E6 mouse monoclonal antibody as detecting antibody and an anti-HPV16 E6 rabbit polyclonal antibody as coating antibody.
Figure 19:
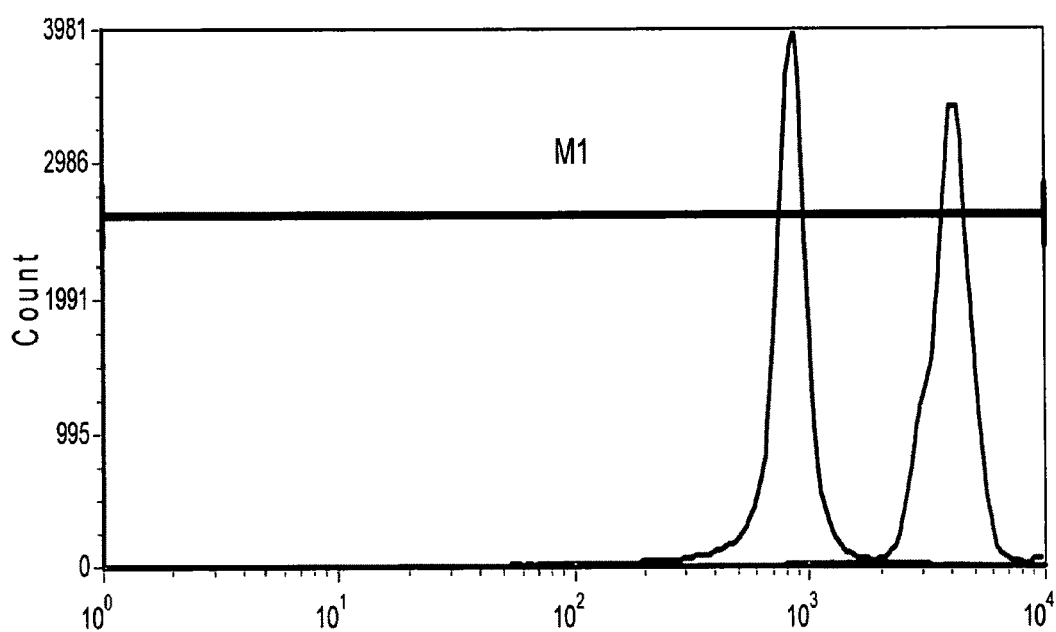
FIG. 19 shows the results of a sandwich beads assay by FACS to detect recombinant HPV18 E6 protein using an anti-HPV18 E6 mouse monoclonal antibody as detecting antibody and an anti-HPV18 E6 rabbit polyclonal antibody as coating antibody.

To demonstrate assay performance varies from different assay format by changing the antibody from coating to detecting antibody, FIG. 18-FIG. 19 show different assays for detecting of HPV 16 E6, and HPV 18 E6 compared to FIG. 15 and FIG. 16, respectively. As an example, FIG. 18 shows results of a sandwich beads assay by FACS to detect recombinant HPV16 E6 protein using a rabbit polyclonal anti-HPV16 E6 antibody as detecting antibody and a mouse monoclonal anti-HPV16 L1 antibody as coating antibody followed by a secondary antibody, anti-rabbit conjugated with PE agent. As the data has indicated, sample containing purified recombinant HPV 16 E6 protein which is captured on the surface of the beads to be detected by FACS shows a discrete peak with higher fluorescent PE (the peak on the right in FIG. 18) from sample containing buffer as a negative control of the assay (the peak on the left in FIG. 18). Results indicate only about a 2 fold difference in fluorescence between the sample containing the specific detecting protein (geometric mean about 2755) and the control sample (geometric mean about 1223) with no detecting protein present. Comparing FIG. 18 to FIG. 15 for detection of HPV 16 E6 protein on beads assay, data suggest that the beads format shown in FIG. 15 provides better dynamic range for assays to allow detecting various amounts of HPV E6 proteins present in the clinical samples.

As an another example, FIG. 19 shows results of a sandwich beads assay by FACS to detect recombinant HPV18E6 protein using a rabbit polyclonal anti-HPV18 E6 antibody as coating antibody and a mouse monoclonal anti-HPV 18E6 antibody as detecting antibody followed by a secondary antibody, anti-mouse conjugated with PE agent. As the data has indicated, sample containing purified recombinant HPV 18E6 protein which is captured on the surface of the beads to be detected by FACS shows a discrete peak with higher fluorescent PE (the peak on the right in FIG. 19) from sample containing buffer as a negative control of the assay (the peak on the left in FIG. 19). Results indicate about a 5 fold difference in fluorescence between the sample containing the specific detecting protein (geometric mean about 3803) and the control sample (geometric mean about 787) with no detecting protein present. Comparing FIG. 19 to FIG. 16 for detection of HPV 18 E6 protein on beads assay, data suggest the beads format shown in FIG. 16 provides better dynamic range for assays to allow detecting various amount of HPV E6 proteins present in the clinical samples.

3. Rapid flow through assay for detecting HPV infection: The rapid immunological assay can be performed vertically on a membrane or laterally in a strip. The lateral flow-through or diffusion one-step rapid immunological assays may also be referred to as immunochromatographic strip tests that would take about 5-15 minutes to obtain results and is easy to use, requiring limited training and no instrumentation. The basic principles of the assay include a solid phase nitrocellulose membrane or strip containing the capture agent to react with a swab sample from a Pap smear. If the patient sample contains the target agent, then the capture agent in the nitrocellulose membrane reacts with the target agent, and a complex is formed and migrates in the nitrocellulose membrane through diffusion or capillary action.

The membrane or stick can also be administered to the test human subject during sample collection and/or combined with the cotton swabs, independently or together, to allow the designed immunological reactions to start and thus obtain the test results instantly, for example, right after insertion of a speculum and the swab into the endocervix of the test human subject. Thus, the one-step rapid immunological assay can serve as a primary screening test. The one-step rapid immunological assay can be performed before additional HPV confirmatory tests, including pap smear cytological tests, the immunological assays and nucleic acid hybridization assays as described herein, or combinations thereof.

The vertical rapid immunological test is conducted in a device having a membrane as a capturing/binding surface for coating or spotting a capture agent thereon. The device further contains a pad underneath the membrane to allow the samples and assay reagent to flow through the membrane. Any target proteins, antibodies, or antigens that are contained in the samples and specifically interact and bind to the capture agent will not flow through and will be captured and be retained on the surface of the membrane, even after several washings to remove non-specific binding. A secondary antibody conjugated with HRP or others enzyme that can be applied on the surface for detecting any protein-antibody complexes retained on the surface and be visualized by colormetric substrates.

The one-step rapid immunological assay as provided herein is a non-invasive and easy to run assay, similar to the types of over-the-counter pregnancy tests without the need of any particular test instrument. The one-step rapid immunological assay can be an in vitro immunochromatographic assay for direct, qualitative detection of common HPV antigens, specific antigens for high risk HPV types, or HPV associated antibodies. The one-step rapid immunological assay can be used as an adjunct test to Pap smear examination, as point-of-care diagnosis, and/or small clinic laboratory testing. The one-step rapid immunological assay is suitable for testing at room temperature conditions by simply adding an obtained sample, with or without dilution, waiting for a reaction time period for the designed reactions to occur, and scoring the results, for example, visualization of the results.

The lateral rapid immunological test is a one-step test using a membrane strip with the capture proteins or antibodies already applied/coated to designated positions on the surface thereof. The only step the test requires is to combine obtained samples having the target proteins or antibodies with a detecting antibody conjugated with collateral gold particles and directly apply the combined mixtures to the membrane strip for the sample fluid to laterally flow through the membrane strip up to the designated positions of the surface of the membrane strip. The capture-target-detecting protein-antibody immuno-complexes can be formed and retained on the designated positions where the capture proteins or antibodies are coated. Positive results can be visualized at these designated positions and no washing or separation is required, thus this is called a one-step method. The whole procedure for the test takes only minutes, for example, less than 15 minutes, and thus the test is also referred to as a one-step rapid test.

The one-step rapid immunochromatographic assay is a simple, fast, and easy to operate assay, which can be conveniently developed for point-of-care use. In general, there is simply mixing of a sample to be tested with a detection antibody as developed herein. The mixture can be applied onto a surface (e.g., a membrane or a glass) that can have the capture antibody already fixed on the surface for a pre-determined reaction time (e.g., in minutes, etc.) at optimized incubation temperature, such as at room temperature. The reaction can be optimized to be short for convenience depending on the quality of the detection antibody used and the assay reaction conditions. Thus, a rapid immunological test with short waiting time period can be performed and the assay results are generally designed to be visually scored without the need of any detection instruments.

4. One-Step HPV Lateral Flow Through Assay: Coating First Anti-HPV Antibody on Membrane to Detect HPV Proteins by a Second Anti-HPV Antibody Conjugated with Collateral Gold Particles The one-step rapid immunological assay may be performed on a membrane or stick test coated with a capture agent, e.g., purified HPV antibodies, recombinant proteins, or HPV-associated antibodies and proteins, etc., as described herein to capture a target agent, e.g., HPV-associated antibodies and HPV-associated proteins, etc., in the clinical sample, followed by an immunoassay detection system.

Figure 20A:
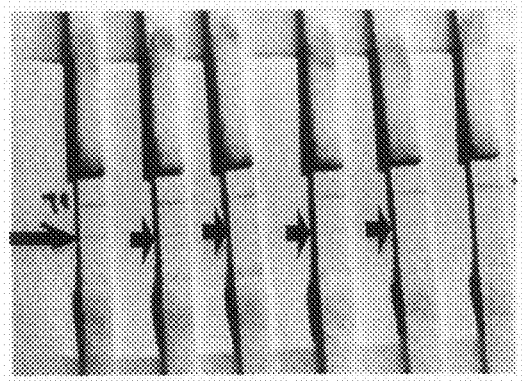
FIG. 20A shows the results of a one-step lateral flow through assay to detect a HPV L1 recombinant protein (from left to right: 875, 435, 0 ug/ml) using a rabbit anti-HPV L1 polyclonal antibody coated on membrane, and conjugated with gold particle (as the detection agent).

As an example, FIGS. 20A-20G show detection of HPV proteins using antibodies described in this invention on one-step lateral flow through. FIG. 20A shows the results of a one-step lateral flow through for detection of HPV L1 recombinant protein using a rabbit anti-L1 polyclonal antibody coated on membrane, and gold particle conjugated for detection. The Test Control (TC) is shown the top line. The second line from the top (arrowed) indicates positive detection of the assay on the left, while the arrow on the right with no visible band shows the negative control of the assay. The concentration of the L1 recombinant protein from left to right is 6, 3, 1.5, 0.75, 0.375, 0 ug/ml. These data demonstrate the one-step HPV lateral flow through assay can detect HPV L1 recombinant protein at concentration of 375 ng/ml or lower.

Figure 20B:
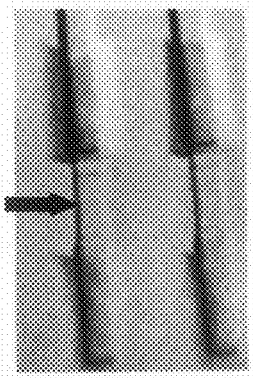
FIG. 20B shows the results of a one-step lateral flow through detecting HPV L1 protein in human serum sample from SCC (squamous cell carcinoma) patient (left) compared to a normal (known HPV negative) serum (right) using the same strips shown in FIG. 9A.

As an example to demonstrate the lateral flow through rapid test can detect HPV L1 protein in clinical samples, FIG. 20B show the results of a one-step lateral flow through for detection of HPV L1 protein in serum sample using the same rabbit anti-HPV L1 polyclonal antibody coated on membrane shown in FIG. 20A. The Test Control (TC) is shown on the top line. The second line from the top (arrowed) indicates positive detection of L1 protein from serum samples of SCC patient (on the left). Serum from a known HPV negative by PCR with no visible band is used as the negative control of the assay (on the right). These data demonstrate the one-step HPV lateral flow through assay can detect HPV L1 protein from a SCC serum sample compared to a HPV negative serum.

Figure 20C:
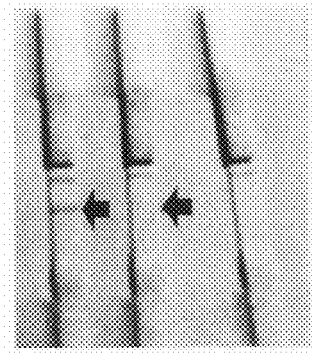
FIG. 20C shows the results of a one-step lateral flow through detecting HPV E6 recombinant protein (from left to right: 10, 2, 0 ug/ml) using a mouse anti-HPV E6 monoclonal antibody coated on membrane, and gold conjugate for detection.

To demonstrate detection of HPV E6 proteins using the one-step lateral flow through assay, FIG. 20C shows the results of a one-step lateral flow through assay for detection of HPV E6 recombinant protein using a mouse anti-HPV E6 monoclonal antibody coated on membrane, and gold conjugate for detection. The Test Control (TC) is shown on the top line. The second line from the top (arrowed) indicates positive detection of the assay on the left, while on the right it showed no visible band indicating the negative control of the assay. The concentration of the E6 recombinant protein from left to right is 10, 2, 0 μg/ml. These data demonstrate the one-step HPV lateral flow through assay can detect HPV E6 recombinant protein at concentration of 2 μg/ml or lower.

Figure 20D:
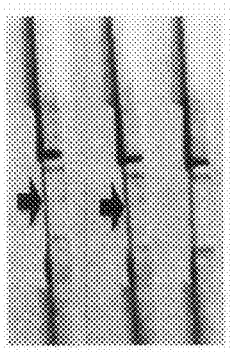
FIG. 20D shows the results of a one-step lateral flow through detecting HPV L1 protein in human serum sample from SCC (squamous cell carcinoma) patient ($1^{st}$ and $2^{nd}$ from the left) compared to a normal (known HPV negative) serum (right) using the same strips shown in FIG. 9C.

To further demonstrate the lateral flow through device can be used for detecting HPV E6 protein in clinical sample, FIG. 20D shows the results of a one-step lateral flow through assay for detection of HPV E6 protein in serum sample using the same mouse anti-E6 monoclonal antibody coated on membrane shown in FIG. 20C. The Test Control (TC) is shown on the top line. The second line from the top (arrowed) indicates positive detection of E6 protein from SCC serum samples ($1^{st}$ and $2^{nd}$ from the left). Serum from a known HPV negative by PCR with no visible band is used as the negative control of the assay (on the right). These data demonstrate the one-step HPV lateral flow through assay can detect HPV E6 protein from a SCC serum sample compared to a HPV negative serum.

Figure 20E:
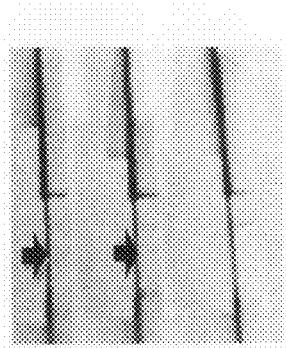
FIG. 20E shows the results of a one-step lateral flow through detecting HPV E6 recombinant protein (from left to right: 875, 435, 0 ug/ml) using another mouse anti-HPV E6 monoclonal antibody coated on membrane, and gold conjugate for detection.

FIG. 20E shows the results of a one-step lateral flow through assay for detection of HPV E6 recombinant protein using another mouse anti-HPV E6 monoclonal antibody coated on membrane and gold conjugate for detection. The Test Control (TC) is shown on the top line. The second line from the top (arrowed) indicates positive detection of the assay on the left, while on the right it showed no visible band indicating that the negative control of the assay. The concentration of the E6 recombinant protein from left to right is 875, 438, 0 µg/ml. These data demonstrate this one-step HPV lateral flow through assay can detect HPV E6 recombinant protein at concentration of 435 µg/ml or lower.

Figure 20F:
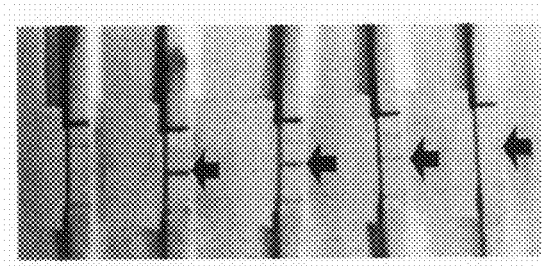
FIG. 20F shows the results of a one-step lateral flow through detecting HPV E7 recombinant protein (from left to right: 0, 660, 66, 6.6, 0.66, ug/ml) using a mouse anti-HPV E7 monoclonal antibody coated on membrane, and gold conjugate for detection.

To demonstrate detection of HPV E7 protein using lateral flow through assay, FIG. 20F shows the results of a one-step lateral flow through assay for detection of HPV E7 recombinant protein using a mouse anti-HPV E7 monoclonal antibody coated on membrane, and gold conjugated for detection. The Test Control (TC) is shown on the top line. The second line from the top (arrowed) indicates positive detection of the assay on the right, while on the left it showed no visible band indicating that the negative control of the assay. The concentration of the E7 recombinant protein from left to right is 0, 660, 66, 6.6, 0.66, µg/ml. These data demonstrate this one-step HPV lateral flow through assay can detect HPV E7 recombinant protein at a concentration of 660 ng/ml or lower.

Figure 20G:
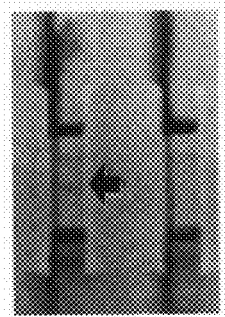
FIG. 20G shows the results of a one-step lateral flow through detecting HPV E7 protein from a known HPV positive human serum sample (left) compared to a known HPV negative serum (right) using the same strips shown in FIG. 20F.

To further demonstrate the lateral flow through device can be used for detecting HPV E7 protein in clinical sample, FIG. 20G show the results of a one-step lateral flow through assay for detection of HPV E7 protein in serum sample using the mouse anti-HPV E7 monoclonal antibody coated on membrane shown in FIG. 20F. The Test Control (TC) is shown the top line. The second line from the top (arrow) indicates positive detection of E7 protein from serum samples of a known HPV positive by PCR (on the left). Serum from a known HPV negative by PCR with no visible band is used as the negative control of the assay (on the right). These data demonstrate the one-step HPV lateral flow through assay can detect HPV E7 protein from a known HPV positive serum sample compared to a HPV negative serum.

5. Expression, Purification, and Preparation of HPV Recombinant Protein Used as Immunogens for Generating Antiserum, and Screening for Monoclonal Antibody from Hybridoma Cell Lines The method described in this Example can be applied to HPV recombinant proteins from any kinds of HPV proteins, HPV proteins of early genes or late genes, including, but not limited to, E2, E6, E7, L1, L2 and can be from various HPV types. One aspect of the invention provides recombinant proteins, such as recombinant hybrid proteins containing a partial sequence or a full length sequence of HPV oncogenic proteins. Examples include full-length E6, E7, and L1 polypeptide sequences, which have been found very difficult to obtain and purify due to undesirable aggregation during protein purification, protein instability, low levels of expression, and low immunogenic responses of purified proteins. For example, many early E6 oncoproteins contain many cysteine amino acids and thus the correct topography of the E6 oncoproteins requires formation of many disulfide bonds properly. In addition, it was known that certain immunological assays using small peptides of early E6 and E7 proteins results in extremely low assay specificity and sensitivity and thus are unsuitable as tools for clinical in vitro diagnostics.

1). Cloning and production of various recombinant proteins encoded by HPV16 E6 and HPV18 E6 gene. Cloning of an exemplary oncogenic E6 early gene from an exemplary HPV type, HPV-16 described herein a 474 base pair (b.p.) DNA fragment containing the 157 amino acid coding region of the HPV-16 E6 gene was obtained by polymerase chain reaction (PCR) amplification. The DNA sequence of the isolated DNA fragment was confirmed by comparing with the sequence from Gene Bank database. All cloning procedures were carried out according to the protocols described in "Molecular Cloning", A Laboratory Manual, eds. Sambrook, Fritsch and Maniatis, Cold Spring Harbor Laboratory Press, 1989. In addition, HPV18E6, fragments were also cloned and sequence confirmed.

2). Cloning and production of various recombinant proteins encoded by HPV16 E7 and HPV18 E7 gene. Cloning of an exemplary oncogenic E7 early gene from an exemplary HPV type, HPV-16, is described herein. A 294 base pair (b.p.) DNA fragment containing the 99 amino acid coding region of the HPV-16 E7 gene was obtained by polymerase chain reaction (PCR) amplification. The DNA sequence of the isolated DNA fragment was confirmed by comparing with the sequence from Gene Bank database. In addition, E7 DNA fragments from different strains of HPV-16 were also cloned from different clinical samples or sources.

The one or more recombinant proteins as described herein were expressed in various suitable systems, such as bacterial expression systems, viral expression systems, yeast expression systems, mammalian expression systems, e.g., in *E coli*, yeast, baculovirus, and/or mammalian cell cultures, generally known in the field. Although the polypeptides have been obtained by other means, embodiments of the instant invention provide one or more recombinant proteins mostly in (or close to) their native forms with a desirable conformation for binding with antibodies from tissues of human subjects with HPV infection in an immunological assay.

For example, GST, MBP, or His tagged-HPV16-E6, HPV18 E6, HPV16 E7, HPV18 E7, HPV16 L1, and HPV18 L1 recombinant proteins were expressed in *E. coli* BL21 (DE3) using IPTG driven induction. After induction of protein expression, tagged-HPV recombinant proteins were obtained from soluble fraction after lysis of the cultured cells and purified to a final concentration of about 0.1 to 1 mg/ml or higher. The purity of the recombinant HPV proteins was estimated to be >90% based on PAGE analysis. Recombinant HPV proteins were used to detect the presence of HPV antibody on clinical samples and were also used as immunogens for production of polyclonal antiserum and monoclonal antibodies.

The cell culture containing various recombinant papillomavirus proteins in various expression vectors as described herein were then scaled up to 1 liter or 10 liter, or 100 liters or higher to obtain high quantity of soluable recombinant protein for purification. The soluble fraction was passed through various chromatography columns with appropriate system to bind to the tag expressed along with the HPV recombinant proteins. The tag-HPV recombinant proteins were then eluted from the column and concentrated down to 100 ml or 10 ml to 1 ml. The purified soluble recombinant HPV proteins were further concentrated and dialyzed with buffers at neutral pH or PBS buffers to be used as immunogen to generate antiserum against the HPV proteins. The soluble recombinant HPV proteins were thus purified from soluble fractions and folded close to their native folding states as in vivo natural conditions.

Obtaining high quality purified recombinant HPV proteins is critical in generating various types of monoclonal antibodies that recognizing common epitopes or specific epitopes for detecting HPV infection. The purified recombinant HPV proteins were tested to confirm its binding to the HPV antibody from the HPV infected clinical samples. Thus, such purified recombinant HPV proteins are suitable for use as immunogen to raise antiserum producing antibody recognizing the natural HPV proteins in vivo.

6. HPV Monoclonal Antibody Development:

Recombinant HPV E6, E7 or L1 proteins expressed in *E coli* was purified, concentrated, and dialyzed with PBS to be used as immunogen. Immunization of mice was performed by following the standard procedure. Titer of serum was tested by ELISA followed by periodical boosting and bleeding. When the titer reaches optimal, fusion was done using standard procedure.

1). Hybridoma screening: To obtain hybridoma cell line producing HPV monoclonal antibody with specificity described in this invention, fusion clones were screened against not only the immunogen but also related or unrelated proteins as well. Two or more purified HPV recombinant proteins were used to screen against each hybridoma clones to obtain the specificity of each monoclonal antibody described herein.

As an example of hybridoma screening, a monoclonal antibody was obtained by screening antibody-producing hybridoma cells with two or more purified recombinant human papillomavirus proteins such that the monoclonal antibody is capable of reacting with the two or more purified recombinant human papillomavirus proteins. The two or more purified recombinant human papillomavirus proteins described herein consists of HPV 16 E6 protein, HPV 16 E7 protein, HPV 16 L1 protein, HPV 18 E6 protein, HPV18 E7 protein, HPV 18 L1 protein, and combinations thereof.

The two or more purified recombinant human papillomavirus viral proteins are HPV early proteins such that the monoclonal antibody is capable of reacting with the two or more human papillomavirus early proteins. For example, the selected hybridoma cell line produced a monoclonal antibody recognizing a common epitope on both HPV16 E6 and HPV16 E7 proteins. As another example, the selected hybridoma cell line produced a monoclonal antibody recognizing a common epitope on both HPV1 8 E6 and HPV18 E7 proteins.

As another example, the two or more purified recombinant human papillomavirus proteins comprise a purified recombinant human papillomavirus early protein and a purified recombinant human papillomavirus late protein such that the monoclonal antibody is capable of reacting with a common epitope on the purified recombinant human papillomavirus early protein and the purified recombinant human papillomavirus late protein. The purified recombinant human papillomavirus early protein consists of HPV 16 E6 protein, HPV 16 E7 protein, HPV 18 E6 protein, HPV18 E7 protein, and combinations thereof, and the purified recombinant human papillomavirus late protein consists of HPV 16 L1 protein, HPV 18 L1 protein, and combinations thereof.

For example, the selected hybridoma cell lines produced a monoclonal antibody recognizing a common epitope on HPV16 E6, HPV16 E7, and HPV16 L1 proteins or a common epitope on HPV16 E6 and HPV18 E6 proteins or a common epitope on HPV16 E7 and HPV18 E7 proteins or a common epitope on HPV16 E6, HPV16 E7, HPV16 L1, HPV18 E6, and HPV18 E7 proteins as described in the drawings of this invention.

As another example of hybridoma screening described in this invention, a monoclonal antibody was obtained by screening antibody-producing hybridoma cells with a first purified recombinant human papillomavirus protein from a first HPV type and a second purified recombinant human papillomavirus protein from a second HPV type such that the monoclonal antibody is capable of reacting with a common epitope on human papillomavirus proteins from two or more different HPV types. The first and the second HPV types are selected from the group consisting of HPV 16, and HPV 18. The two or more different HPV types can also be selected from the group consisting of high risk HPV types, low risk HPV types, HPV-16, HPV-18, HPV-31, HPV-33, HPV-35, HPV-39, HPV-45, HPV-51, HPV-52, HPV-56, HPV-58, HPV-59, and HPV-68, HPV-6, HPV-11, HPV-42, HPV-43, HPV-44, HPV-53, HPV-54, HPV-55, and HPV-56, and combinations thereof. As an example, the first and the second purified recombinant human papillomavirus proteins consists of HPV 16 E6 protein, HPV 16 E7 protein, HPV 16 L1 protein, HPV 18 E6 protein, HPV18 E7 protein, HPV 18 L1 protein, and combinations thereof.

As another example of hybridoma screening described in this invention, a monoclonal antibody was obtained by screening antibody-producing hybridoma cells with a first purified recombinant human papillomavirus protein from a first HPV type and a second purified recombinant human papillomavirus protein from a second HPV type such that the monoclonal antibody is capable of reacting with a specific epitope on only one of the first and the second purified recombinant human papillomavirus proteins and not the other purified recombinant human papillomavirus protein. The first and the second purified recombinant human papillomavirus proteins consists of HPV 16 E6 protein, HPV 16 E7 protein, HPV 16 L1 protein, HPV 18 E6 protein, HPV18 E7 protein, HPV 18 L1 protein, and combinations thereof.

2). Hybridoma cell line stocks: positive clones with desired reactivity on ELISA were selected and cloned down to single cell. Each single clone was then grown up by tissue culture. When the cell numbers reach millions of cell per ml, the cells were frozen down and kept at −80 C or in liquid nitrogen as stock for each cell line.

3). Ascites production: each cell line was grown in tissue culture and injected to mice for ascites production. Ascites were collected and processed for Ig purification by protein G column. Purified Ig from each cell line was isotyped and used for HPV immunoassays.

7. The Specificity of Anti-HPV Antibodies.

One or more immunological assays can be used to test the specificity of the monoclonal antibodies generated by screening the hybridoma cell lines with two or more HPV recombinant proteins. EIA (Enzyme Immuno Assay) and/or Western blots were used as the assay format to test the specificity of the HPV antibodies described herein. Various purified recombinant HPV proteins, including the original screening proteins used for obtaining the anti-HPV antibodies and other proteins not used for screening, were used to coat on the microtiter plate to test the specificity of the obtained anti-HPV antibodies on EIA. Proteins in cell lysate from cervical cancer cell lines (with or without HPV infection) were also used to test the specificity of the anti-HPV antibodies by western blot. To confirm the binding and reactivity of the HPV antibodies with proteins from HPV infected cell lines, western blot is very useful to demonstrate specific protein bands corresponding to the proteins present in the HPV-infected cell lines. The protein bands from Western blots were compared to recombinant HPV proteins at their expected molecular weight positions on SDS-PAGE gels. Cell lysate from cervical cancer cell lines, including Hela cell line (HPV18 positive), SiHa cell line (HPV16 positive) and C33A cell line (non-HPV infected) were used to demonstrate detection of HPV E6, E7, or L1 by the HPV monoclonal antibody on western blot.

Figure 21A:
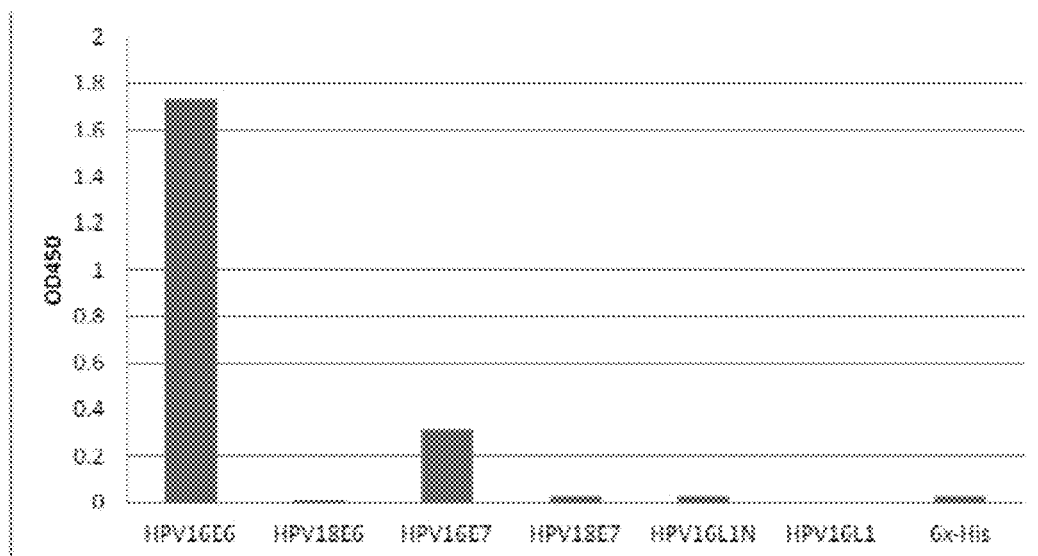
FIG. 21A shows the specificity of a monoclonal antibody capable of reacting with both HPV16 E6 and HPV16 E7 recombinant proteins (different HPV proteins from the same HPV type) and recognizing a common epitope on the different HPV16 E6 and HPV16 E7 proteins from the same HPV 16 type as assayed on EIA (enzyme immuno assays) according to one embodiment of the invention.
Figure 21B:
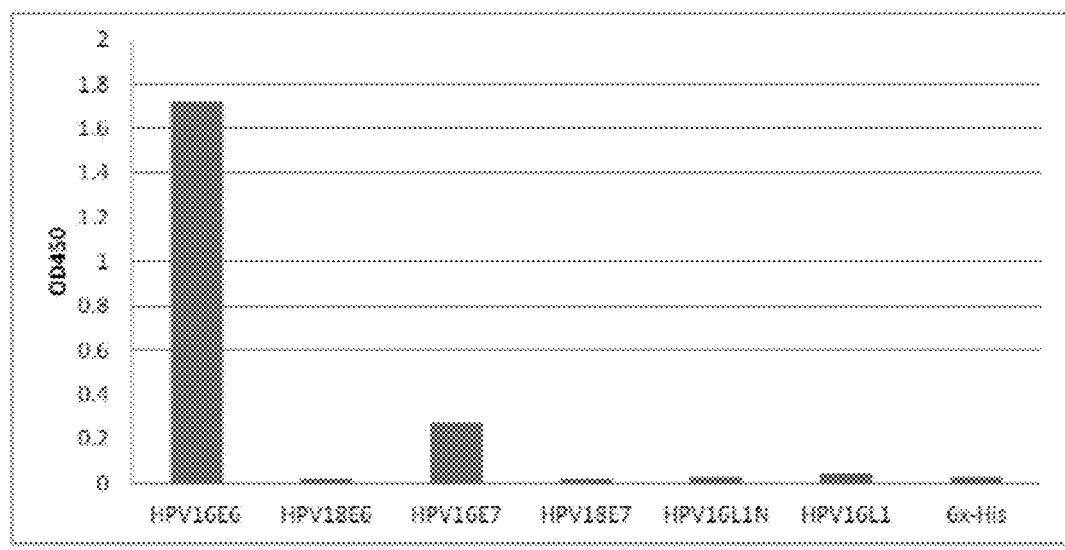
FIG. 21B shows the specificity of another monoclonal antibody capable of reacting with both HPV16 E6 and HPV16 E7 recombinant proteins and recognizing a common epitope on the HPV 16 E6 and HPV16 E7 proteins as assayed on EIA according to one embodiment of the invention.

To demonstrate a monoclonal antibody capable of binding to two or more HPV viral proteins from the same HPV type as described in this invention, FIG. 21A and FIG. 21B show the specificity of a monoclonal antibody, capable of reacting with both recombinant HPV16 E6 and HPV16 E7 proteins on EIA.

These data demonstrate the monoclonal antibody described herein reacts specifically to HPV16 E6 and HPV16 E7, but not reactive to HPV16L1, HPV18 E6 or HPV18E7. FIG. 21A and FIG. 21B represent two different clones of hybridoma cells, with each clone being capable of producing a monoclonal antibody recognizing a common epitope on both HPV16 E6 and HPV16 E7 proteins.

Figure 22A:
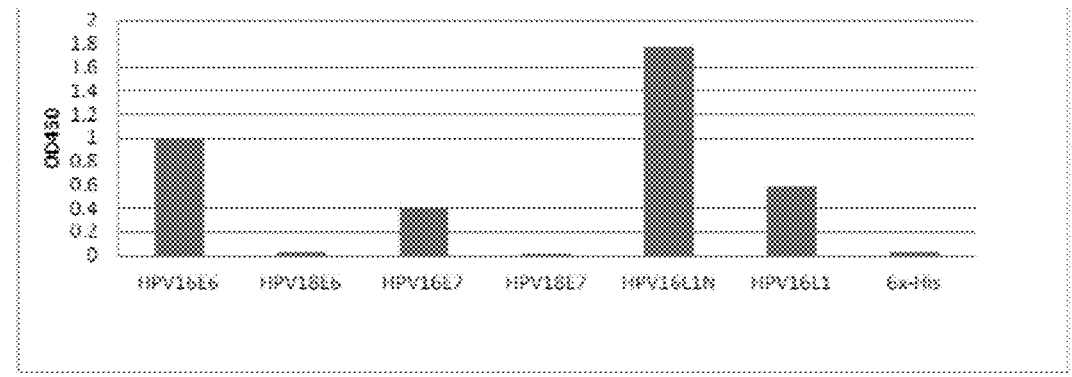
FIG. 22A shows the specificity of a monoclonal antibody capable of reacting with HPV16 E6, E7, L1 & L1 N-terminal recombinant proteins (different HPV proteins from the same HPV type) and recognizing a common epitope on the different E6, E7, L1, and L1 N-terminal proteins from the same HPV 16 type as assayed on EIA according to another embodiment of the invention.

To demonstrate a monoclonal antibody capable of binding to an early HPV viral protein and a late HPV viral proteins from the same HPV type as described in this invention, FIG. 22A shows the specificity of a monoclonal antibody capable of reacting with recombinant HPV E6, HPV E7 and HPV L1 proteins on EIA. The recombinant protein coated on microtiter plate to be detected by the antibody described herein is in native form. These data demonstrate the monoclonal antibody described herein reacts strongly to the native forms of recombinant HPV16 E6 and L1 proteins and weakly to the native form of recombinant HPV16 E7 protein, but is non-reactive to native form of recombinant HPV18 E6 or HPV18 E7. These data indicate that this antibody recognizes an HPV 16 common epitope on the native form of HPV16E6, HPV16E7 and HPV16L1 protein.

Figure 22B:
FIG. 22B shows a western blot of the monoclonal antibody as shown in FIG. 22A, confirming its binding to all of the HPV16 E6, E7 and L1 recombinant proteins.

FIG. 22B shows the results of a Western blot analysis of a monoclonal antibody capable of reacting with recombinant HPV E6, HPV E7 and HPV L1 proteins. The recombinant protein detected by Western blot using the antibody described herein demonstrates the detection of HPV E6 (about 18-20 kDa) and HPV L1 (about 55 kDa) proteins. The bands from each recombinant protein shown with expected molecular weight indicate the monoclonal antibody described herein reacts strongly to denatured HPV16 E6 and HPV18E6 and weakly to denatured HPV L1 proteins on Western blot, and there is no detectable reactivity to HPV16 E7 nor HPV18 E7. Comparing the results as shown in FIG. 22A and FIG. 22B, these data indicate that this anti-HPV monoclonal antibody recognizes an HPV common epitope on the native forms of HPV16 E6, HPV16 E7 and HPV16 L1 protein as well as denatured forms of HPV18 E6 recombinant protein.

Figure 22C:
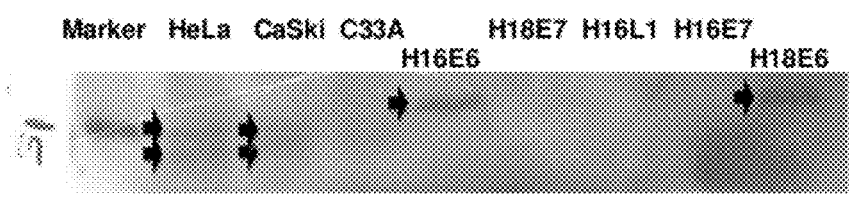
FIG. 22C shows the results of a western blot of cell lysate from cervical cancer cell lines using the monoclonal antibody as shown in FIG. 22A, confirming its binding to all of the HPV16 E6, E7 and L1 viral proteins present in these cervical cancer cell lines.

FIG. 22C shows the results of a Western blot using cell lysate from various cervical cancer cell lines to react with the same monoclonal antibody tested in FIG. 22B binding with recombinant HPV E6, HPV E7 and HPV L1 proteins. Both the cell lysate and recombinant proteins in their denatured forms are tested and shown here (the same monoclonal antibodies as shown in FIG. 22B). The double bands as detected by the monoclonal antibody around the standard molecular weight marker of 17 kDa demonstrate the detection of HPV E6 protein (about 18 kDa) and HPV E7 (about 15 kDa) protein from cervical cancer cell line in HeLa (HPV18) and SiHa (HPV16) cell lines, but not C33A (non-HPV infection) cell line. The bands on the recombinant protein lanes shown with expected molecular weight indicate that the monoclonal antibody reacts strongly to denatured HPV16 E6 and HPV18E6 recombinant proteins, but weakly to denatured HPV L1 recombinant proteins on western blot, and there is no detectable binding to HPV16E7 nor HPV18E7 recombinant proteins.

Figure 23A:
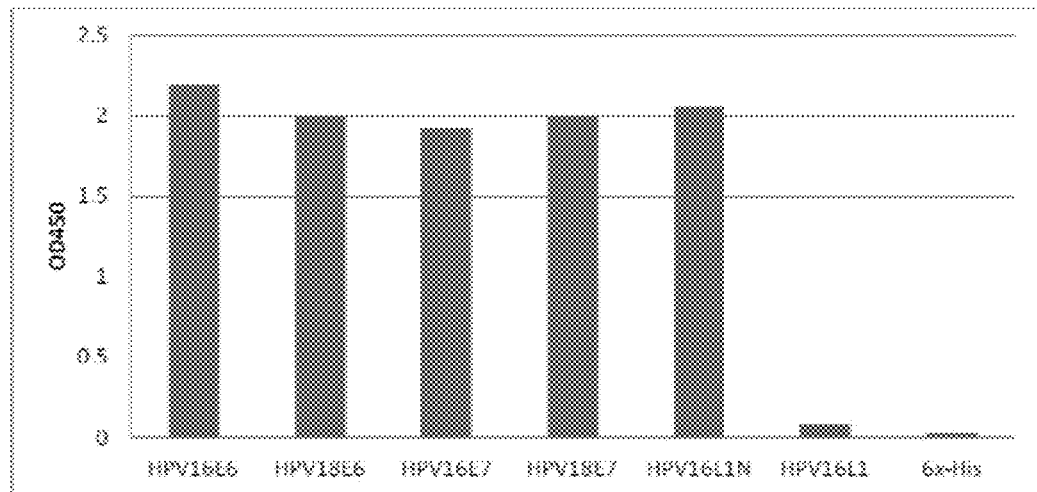
FIG. 23A shows the specificity of a monoclonal antibody capable of binding to all of the recombinant HPV16 E6, E7, and L1 N-terminal proteins as well as HPV18 E6 and E7 proteins (HPV proteins from different HPV types) and recognizing a common epitope on the E6, E7, L1 N-terminal proteins from HPV16 and HPV18 as assayed on EIA according to another embodiment of the invention.

To demonstrate a monoclonal antibody capable of binding to an early HPV viral protein and a late HPV viral protein from different HPV types as described in this invention, FIG. 23A shows the specificity of a monoclonal antibody capable of reacting with recombinant E6, E7 and L1 proteins from both HPV16 and HPV 18 on EIA. These data demonstrate this monoclonal antibody reacts specifically to all of the recombinant E6, E7 and L1 proteins of HPV16, and the recombinant E6 and E7 proteins of HPV18, but not to its common his-tag peptide. These data indicate that this antibody recognizes a common epitope shared by HPV16 and HPV18, as evidenced by its ability to bind to all of the recombinant HPV16 E6, HPV16 E7, HPV16 L1, HPV18 E6, and HPV18 E7 proteins.

Figure 23B:
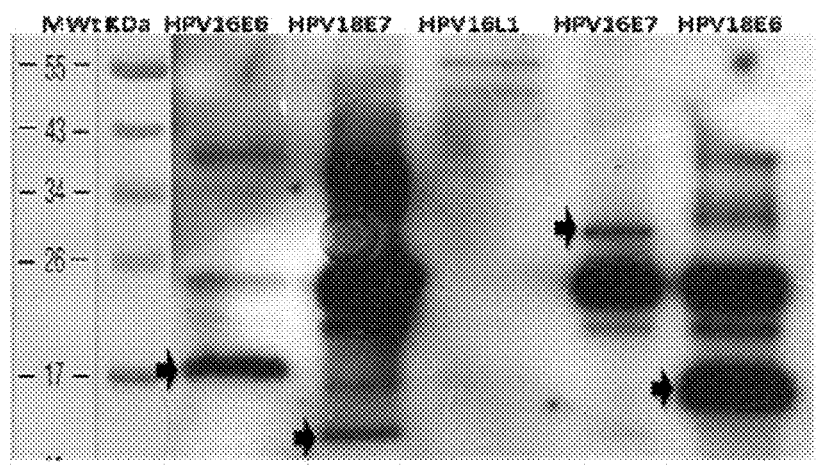
FIG. 23B shows the results of a western blot using the monoclonal antibody as shown in FIG. 3A, confirming its binding to the different recombinant proteins and recognizing a common epitope on the different E6, E7 and L1 proteins from the two different HPV types HPV16 and HPV18.

FIG. 23B shows the results of a Western blot using a monoclonal antibody that recognized a common epitope and is capable of binding to the recombinant E6, E7 and L1 proteins of HPV16 and HPV18. The reactivity of this monoclonal antibody to these recombinant proteins demonstrate that the monoclonal antibody is capable of recognizing E6 (about 18 kDa), E7 (About 15 kDa) and L1 (about 55 kDa) proteins. The resulting bands from each recombinant protein lane of the Western blot analysis showed up at the expected molecular weight position and indicated that this monoclonal antibody reacts strongly to denatured E6 and E7 proteins from both HPV 16 and HPV18, and weakly to denatured L1 proteins on Western blot. The results of FIG. 23A and FIG. 23B indicate that this monoclonal antibody recognizes an HPV common epitope and is capable of binding to the native and denatured form of HPV16 E6, HPV16 E7, HPV16 L1, HPV18 E7 and HPV18 E6 proteins.

Figure 23C:
FIG. 23C shows a western blot cell lysate from cervical cancer cell lines using the monoclonal antibody as shown in FIG. 3A, confirming its binding to the HPV16 E6, E7 and L1 proteins as well as HPV18 E6, E7 and L1 viral proteins present in these cervical cancer cell lines.

FIG. 23C shows the results of a Western blot using cell lysate from various cervical cancer cell lines to react with the same monoclonal antibody tested in FIG. 23B binding with recombinant HPV E6, HPV E7 and HPV L1 proteins. Both the cell lyate and the recombinant proteins in their denatured forms were tested and shown here (the same monoclonal antibodies as shown in FIG. 23B). The double bands as detected by the monoclonal antibody around the standard molecular weight marker of 17 kDa demonstrate the detection of HPV E6 protein (about 18 kDa) and HPV E7 (about 15 kDa) protein from cervical cancer cell line in HeLa (HPV18) and SiHa (HPV16) cell lines, but not C33A (non-HPV infection) cell line. The bands on the recombinant protein lanes shown with expected molecular weight indicate that the monoclonal antibody reacts strongly to denatured HPV16 E6, HPV18 E6, HPV18 E7 recombinant proteins but weakly to denatured HPV L1 recombinant proteins, and there is no detectable binding to HPV16E7 recombinant proteins on the Western blot.

Figure 24A:
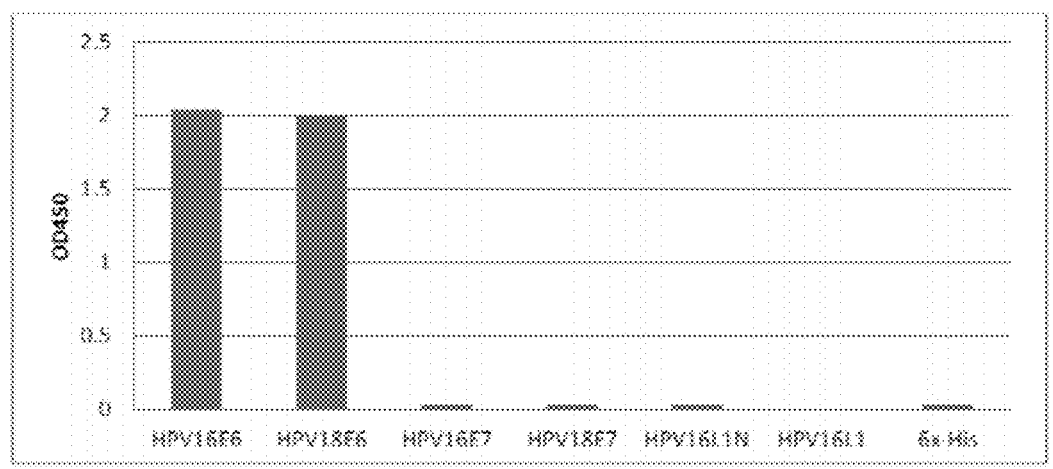
FIG. 24A shows the specificity of a monoclonal antibody capable of binding to two E6 recombinant proteins (HPV16 E6 and HPV18 E6, E6 proteins from different HPV types) and recognizing a common epitope on the two E6 proteins from different HPV types as assayed on EIA according to another embodiment of the invention.

To demonstrate a monoclonal antibody capable of binding to two or more HPV viral proteins from different HPV types as described in this invention, a monoclonal antibody capable of reacting with recombinant E6 proteins of HPV 16 and HPV18 was also the obtained. FIG. 24A shows the specificity of a monoclonal antibody that recognizes the common epitope and is capable of binding to recombinant HPV16 E6 and HPV18E6 proteins on EIA. The recombinant protein coated on microtiter plate to be detected by the antibody described herein is in its native form. These data demonstrate that the monoclonal antibody reacts strongly to the native form of recombinant HPV16 E6 and HPV18E6 proteins, but does not react with the native form of either recombinant HPV E7 or recombinant HPV L1 proteins. These data indicate that this antibody recognizes an HPV E6 common epitope and is capable of binding to the native form of recombinant HPV16 E6, and HPV18 E6 proteins.

Figure 24B:
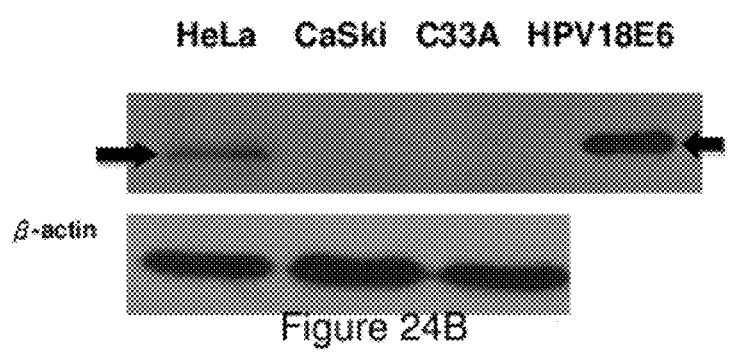
FIG. 24B shows the results of a western blot analyzing the cell lysate from cervical cancer cell lines using the monoclonal antibody as shown in FIG. 24A, confirming its binding to HPV16 E6 as well as HPV18 E6 viral proteins present in these cervical cancer cell lines.

FIG. 24B shows the results of a Western blot using cell lysate from various cervical cancer cell lines to react with the same monoclonal antibody tested in FIG. 24A binding with recombinant E6 proteins of HPV 16 and HPV18. Both the cell lyate and the recombinant proteins in their denatured forms were tested and shown here (the same monoclonal antibodies as shown in FIG. 24A). The single band as detected by the monoclonal antibody around the standard molecular weight marker of 17 kDa demonstrate the detection of HPV E6 protein (about 18 kDa) from cervical cancer cell line in HeLa (HPV18), but not C33A (non-HPV infection) cell line. The bands on the recombinant protein lanes shown with expected molecular weight indicate that the monoclonal antibody reacts strongly to denatured HPV18E6 recombinant proteins.

Figure 25:
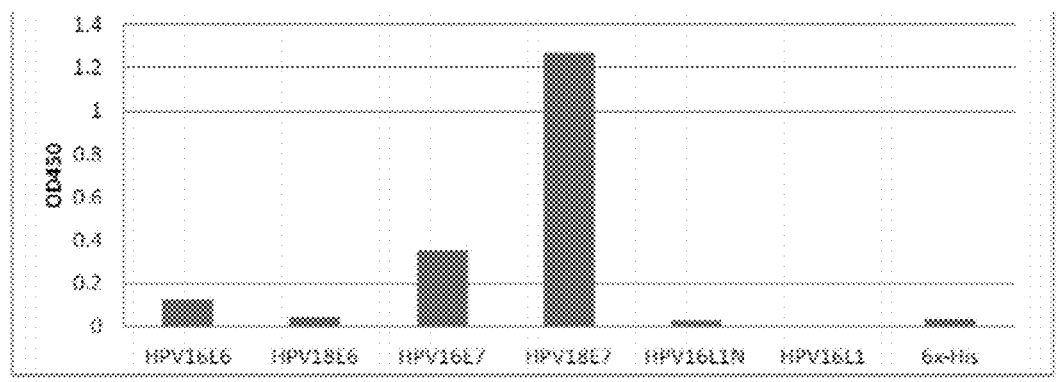
FIG. 25 shows the specificity of a monoclonal antibody capable of reacting with two recombinant HPV16 E7 and HPV18 E7 proteins (E7 proteins from different HPV types) and recognizing a common epitope on the two E7 proteins from different HPV types as assayed on EIA.

As another example to demonstrate a monoclonal antibody capable of binding to two or more HPV viral proteins from different HPV types as described in this invention, FIG. 25 shows the specificity of a monoclonal antibody capable of reacting with both recombinant HPV16 E7 and HPV18 E7 protein on EIA. The recombinant protein coated on microtiter plate detected by the antibody described herein is in its native form. These data demonstrate the monoclonal antibody described herein reacts strongly to native form of recombinant HPV16 E7 and HPV18 E7 proteins, but non-reactive to native form of recombinant HPV E6 nor HPV L1 proteins. These data indicate that this antibody recognizes an HPV E7 common epitope and is capable of binding to the native form of HPV16 E7 and HPV18 E7 proteins.

Figure 26:
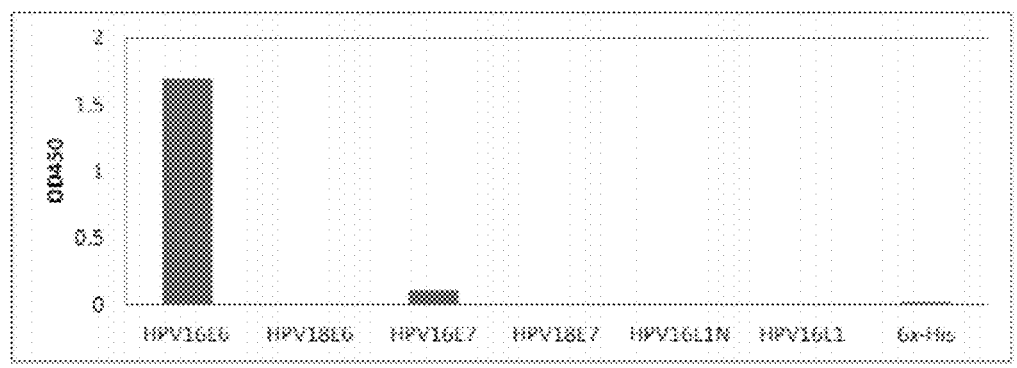
FIG. 26 shows the specificity of a monoclonal antibody capable of reacting with only HPV16 E6 recombinant protein but not with any other HPV recombinant proteins on EIA according to one embodiment of the invention.

To demonstrate a monoclonal antibody capable of binding to only a first HPV viral protein, but not a second HPV viral protein different from the first HPV viral protein, FIG. 26 shows the specificity of a monoclonal antibody capable of reacting with recombinant HPV16 E6 but not with other recombinant HPV proteins on EIA. Data indicate the specificity of this monoclonal antibody that recognizes a specific epitope and is capable of binding to HPV16 E6 only, and not to HPV18 E6 or other recombinant HPV proteins on EIA. The recombinant protein coated on microtiter plate detected by the antibody described herein is in native form. These data demonstrate the monoclonal antibody described herein reacts strongly to the native form of recombinant HPV16 E6 proteins but is non-reactive to the native form of recombinant HPV E7 or L1 proteins. These data also indicate that this antibody recognizes an HPV16 E6-specific epitope and is capable of binding to HPV16 E6 protein only.

As an another example, FIG. 27 shows the specificity of a monoclonal antibody capable of reacting with recombinant HPV18 E6 protein but not with other recombinant HPV proteins on EIA. Data indicate the specificity of this monoclonal antibody that recognizes a specific epitope and is capable of binding to HPV18 E6 only, but not to HPV16 E6 or other recombinant HPV proteins. The recombinant protein coated on microtiter plate detected by the antibody described herein is in native form. These data demonstrate the monoclonal antibody described herein reacts strongly to the native form of recombinant HPV18 E6 proteins but is non-reactive to the native form of recombinant HPV E7 or HPV L1 proteins. These data indicate that this antibody recognizes an HPV18 E6-specific epitope and is capable of binding to HPV18 E6 protein only.

Figure 27A:
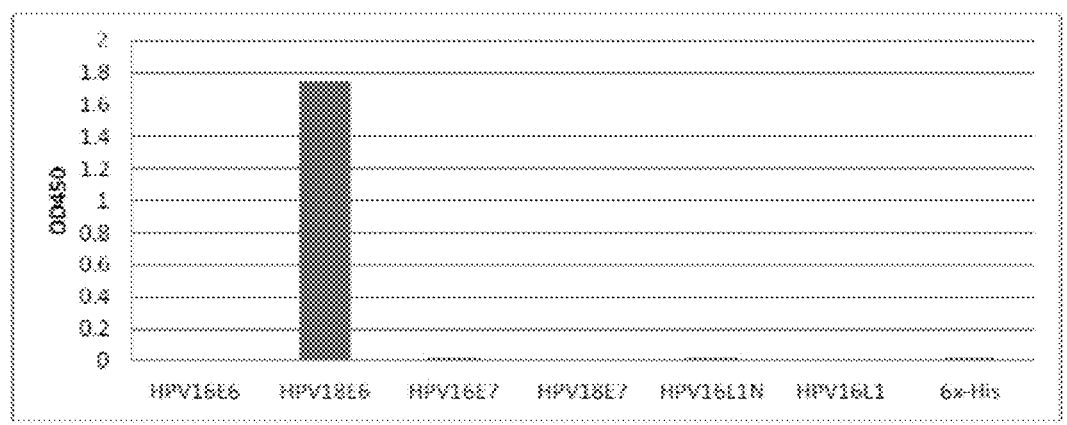
FIG. 27A shows the specificity of a monoclonal antibody capable of reacting specifically with only HPV18 E6 recombinant protein, but not with any other HPV16 or HPV18 recombinant proteins as assayed on EIA according to another embodiment of the invention.
Figure 27B:
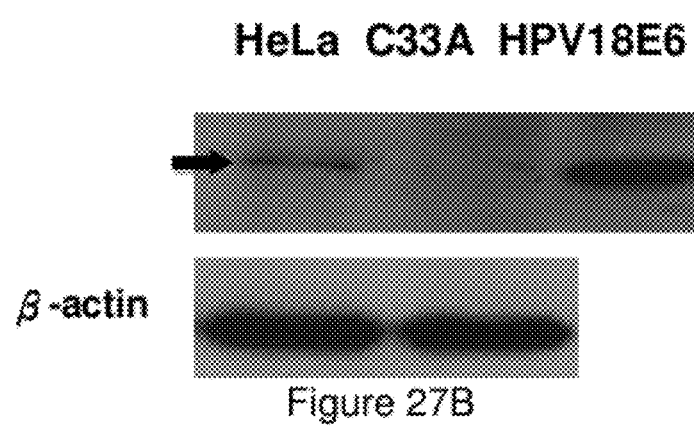
FIG. 27B shows the results of a western blot analyzing the cell lysate from different cervical cancer cell lines using the monoclonal antibody as shown in FIG. 27A, confirming its binding to the HPV18 E6 viral protein but not HPV E7 viral protein that are present in Hela cell line.

FIG. 27B shows the results of a Western blot using cell lysate from various cervical cancer cell lines to react with the same monoclonal antibody tested in FIG. 27A binding with recombinant HPV 18 E6 proteins. Both the cell lyate and the recombinant proteins in their denatured forms were tested and shown here (the same monoclonal antibodies as shown in FIG. 27A). The single band as detected by the monoclonal antibody around the standard molecular weight marker of 17 kDa demonstrate the detection of HPV E6 protein (about 18 kDa) from cervical cancer cell line in HeLa (HPV18), but not C33A (non-HPV infection) cell line. The bands on the recombinant protein lanes shown with expected molecular weight indicate that this monoclonal antibody reacts strongly to denatured HPV18E6 recombinant proteins only.

Figure 28:
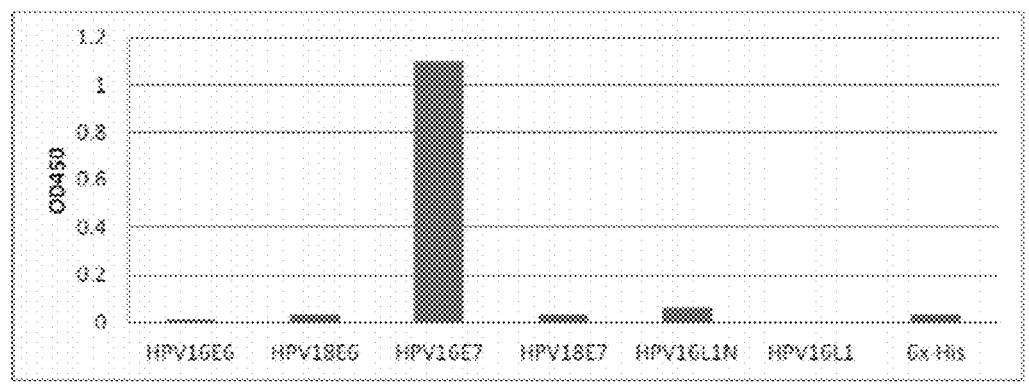
FIG. 28 shows the specificity of a monoclonal antibody capable of reacting specifically with an HPV16 E7 recombinant protein, but not with any other HPV recombinant proteins as assayed on EIA according to another embodiment of the invention.

As another example, FIG. 28 shows the specificity of a monoclonal antibody capable of reacting with recombinant HPV16 E7 but not with other recombinant HPV proteins on EIA. Data indicate the specificity of the monoclonal antibody that recognizes specific epitope and is capable of binding to HPV16 E7 only, but not to HPV18 E7 or other recombinant HPV proteins on EIA. The recombinant protein coated on microtiter plate detected by the antibody described herein is in its native form. These data demonstrate the monoclonal antibody described herein reacts strongly to the native form of recombinant HPV16 E7 proteins, but no detectable binding to the native form of recombinant HPV E6 or L1 proteins. These data indicate that this antibody recognizes an HPV16 E7-specific epitope and is capable of binding to HPV16 E7 protein only.

Figure 29:
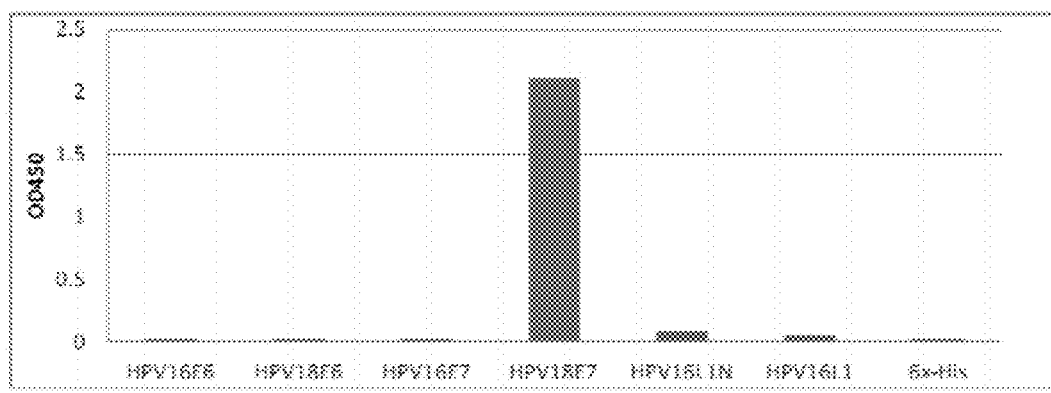
FIG. 29 shows the specificity of a monoclonal antibody capable of reacting specifically with a recombinant HPV18 E7 recombinant protein, but not with any other HPV recombinant proteins as assayed on EIA according to another embodiment of the invention.

As an another example to demonstrate a monoclonal antibody capable of binding to only a first HPV viral protein, but not a second HPV viral protein different from the first HPV viral protein, FIG. 29 shows the specificity of a monoclonal antibody capable of reacting with recombinant HPV18 E7 but not with other recombinant HPV proteins on EIA. Data indicate the specificity of the monoclonal antibody that recognizes a specific epitope and is capable of binding to HPV18 E7 only, and not to HPV16 E7 or other recombinant HPV proteins. The recombinant protein coated on microtiter plate detected by the antibody described herein is in native form. These data demonstrate the monoclonal antibody described herein reacts strongly to the native form of recombinant HPV18 E7 proteins but is non-reactive to native form of recombinant HPV E6 or HPV L1 proteins. These data indicate that this antibody recognizes an HPV18 E7-specific epitope and is capable of binding to HPV18 E7 protein only.

Figure 30A:
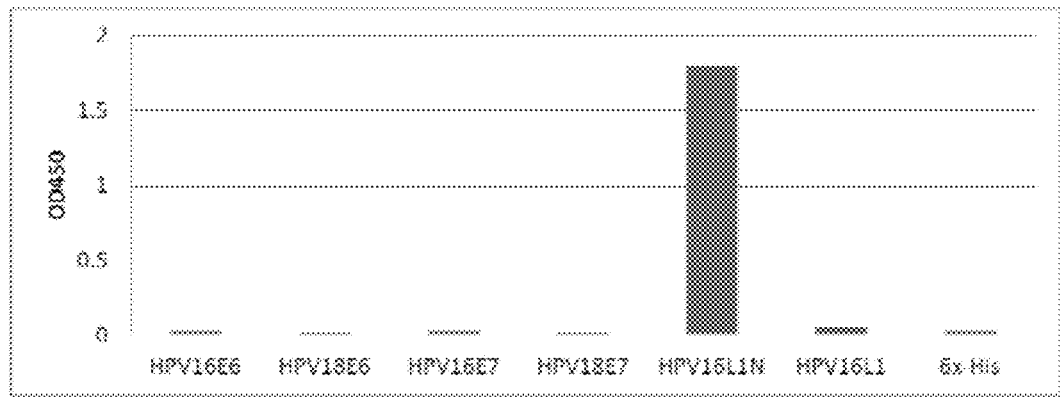
FIG. 30A shows the specificity of a monoclonal antibody capable of reacting specifically with an HPV16 L1 N-terminal recombinant protein, but not with any other HPV recombinant proteins as assayed on EIA according to another embodiment of the invention.
Figure 30B:
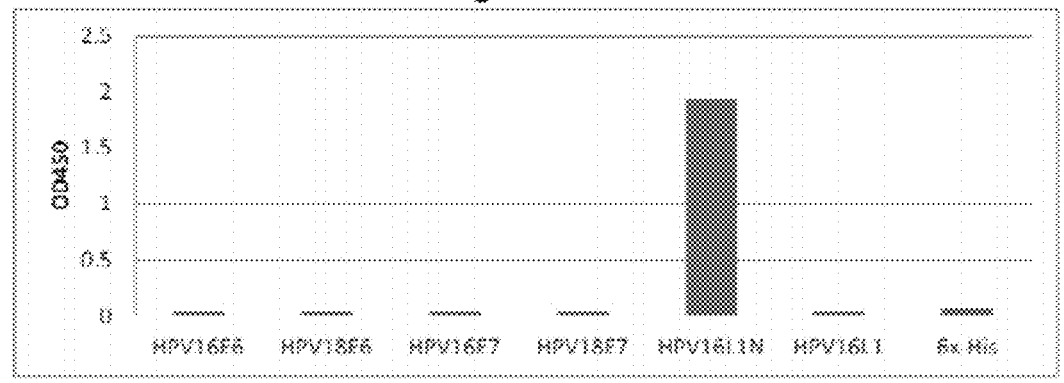
FIG. 30B shows the specificity of another monoclonal antibody capable of reacting specifically with an HPV16 L1 N-terminal recombinant protein, but not with any other HPV recombinant proteins as assayed on EIA.

As an another example to demonstrate a monoclonal antibody capable of binding to only a first HPV viral protein, but not a second HPV viral protein different from the first HPV viral protein, FIG. 30 shows the specificity of a monoclonal antibody capable of reacting with recombinant HPV16 L1-N terminal but not with other recombinant HPV proteins on EIA. Data indicate the specificity of the monoclonal antibody that recognizes a specific epitope and is capable of binding to HPV16 L1 N-terminal only, but does not crossed react with HPV16 L1 or other recombinant HPV proteins on EIA. The recombinant protein coated on microtiter plate detected by the antibody described herein is in its native form. These data demonstrate the monoclonal antibody described herein reacts strongly to the native form of recombinant HPV16 L1-N terminal proteins but is non-reactive to the native form of recombinant HPV E6 or HPV E7 proteins. These data indicate that this antibody recognizes an HPV16 L1 N-terminal specific epitope and is capable of binding to HPV16 L1 N-terminal protein only. FIG. 30A and FIG. 30B represent two different hybridoma clones of cell line producing antibody specific to HPV L1 proteins.

Figure 31:
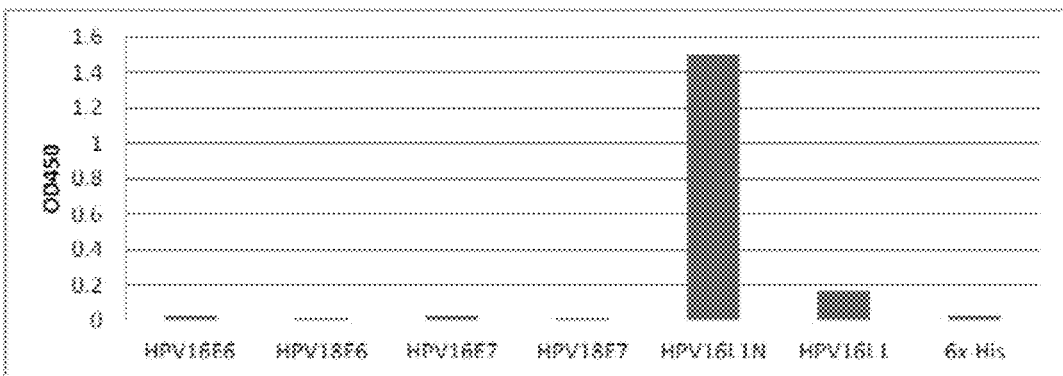
FIG. 31 shows the specificity of a monoclonal antibody capable of reacting specifically with only the HPV16 L1 & L1 N-terminal recombinant proteins, but not with any other HPV recombinant proteins as assayed on EIA according to another embodiment of the invention.

As an another example, FIG. 31 shows the specificity of a monoclonal antibody capable of reacting with recombinant HPV16L1 and HPV16 L1-N terminal but not with other recombinant HPV proteins on EIA. Data indicate the specificity of the monoclonal antibody that recognizes a specific epitope and is capable of binding to HPV16 L1 and HPV16 L1 N-terminal only, and not to other recombinant HPV proteins on EIA. The recombinant protein coated on microtiter plate detected by the antibody described herein is in native form. These data demonstrate the monoclonal antibody described herein reacts strongly to the native form of recombinant HPV 16 L1 and HPV16 L1-N terminal proteins, but is non-reactive to the native form of recombinant HPV E6 or HPV E7 proteins. These data indicate that this antibody recognizes an HPV16 L1 N-terminal-specific epitope and is capable of binding to HPV16 L1 and HPV16 L1 N-terminal protein.

To demonstrate the antibodies described in this invention can be used in various immunoassay, a sandwich ELISA was performed. The assay includes 1). Coating first anti-HPV antibody on the microtiter plate, 2). Adding HPV protein to react with the first antibody, thus to be captured on the surface of microtiter plate, 3). Adding a second anti-HPV antibody which is conjugated with HRP, followed by TMB substrate to report the binding activity by ELISA reader. The sandwich assay provides specific binding of the protein with the first and the second antibody and thus differentiates the antibody specificity for the proteins on the surface to be detected by the ELISA reader. Various antibodies described in this invention were applied in the coating and detection to demonstrate the antibody specificity. As an example, Table 3 shows the experiment design and result of an ELISA (Enzyme linked Immuno Sandwich Assay) to detect the presence of HPV18 E6 recombinant protein. The results show HPV18E6 recombinant protein can be detected in the assay when the coating and detecting antibody are capable of reacting with HPV18E6, while HPV16E6 recombinant protein can't be detected if the coating antibody is capable of binding to HPV16E6 but the detecting antibody reacts with HPV18E6 only. Similar results were obtained when using an HPV18 E6-specific antibody as a coating followed by a detecting antibody capable of binding to both HPV16E6 and HPV18E6. Data demonstrate the specificity of the antibody recognizes HPV18 E6 when HPV18 E6 recombinant protein is used as the testing protein in the sandwich assay but is non-reactive to recombinant HPV16 E6 protein as the antigen of the sandwich assay. The assay format described herein can be used to detect HPV18 E6 proteins present in biological samples, including but not limited to cell lysate from cervical cancer cell lines, cervical scrape samples, tissue, body fluid, serum, etc. This specific sandwich assay provides type specific assay for HPV 18, and thus excludes the binding of HPV16 E6.

TABLE 3

Sandwich ELISA for detecting of HPV E6 protein

| coating antibody | anti-HPV16& 18E6 | anti-HPV16& 18E6 | anti-HPV18E6 | anti-HPV18E6 |
|---|---|---|---|---|
| testing protein | recombinant HPV18E6 | recombinant HPV16E6 | recombinant HPV18E6 | recombinant HPV16E6 |
| detecting antibody | anti-HPV18E6 | anti-HPV18E6 | anti-HPV16& 18E6 | anti-HPV16& 18E6 |
| ELISA results (OD450) | 1.5 | 0.05 | 1.45 | 0.05 |

As an another example to demonstrate the antibodies described in this invention can be used to detect HPV E7 protein, Table 4 shows the result of ELISA to detect the presence of HPV18 E7 recombinant protein using a monoclonal antibody against HPV 18 E7 (recognizing HPV 18 E7) for both the coating and the detecting antibody. Data demonstrate that the specificity of the antibody recognizes HPV18E7 using HPV18E7 recombinant protein as the antigen of the sandwich assay but is non-reactive using HPV16E7 as the antigen of the sandwich assay. The assay format described herein can be used to detect HPV E7 proteins present in biological samples, including but not limited to cell lysate from cervical cancer cell lines, cervical scrape samples, tissue, body fluid, serum, etc. This sandwich assay provides an E7-specific assay for HPV 18, and thus is useful for the screening of HPV infection and the detecting of HPV E7 oncogenic proteins.

TABLE 4

Sandwich ELISA for detecting of HPV E7 protein

| coating antibody | anti-HPV18E7 | anti-HPV18E7 |
|---|---|---|
| testing protein | recombinant HPV18E7 | recombinant HPV16E7 |
| detecting antibody | anti-HPV18E7 | anti-HPV18E6 |
| ELISA results (OD450) | 1.25 | 0.04 |

8. Application of the Anti-HPV Antibodies.

The HPV antibodies described in this invention can be used in various immunoassays for detecting general HPV infection as well as infection by various specific HPV genotypes, high risk HPVs and low risk HPVs. The samples to be used in detecting the presence of HPV proteins can be obtained from, but are not limited to, cervical tissues, cervical cells, cervical scrapes, serum, and body fluids. The immunoassays useful for screening or diagnosing cervical cancer or HPV infection include IHC assays, ICC assays, flow cytometry assays, assays using antibodies coupled to beads, rapid tests, protein chip assays, immunoassays with dot blots, immunoassays with slots, as well a conventional ELISA assay. As a screening test, the HPV antibodies can be used to detect HPV proteins in situ present in epithelium cells of cervical scrape from general population in cervical cancer screening as evidenced by ICC staining scored by certified cytologists. As a confirming test, the HPV antibodies can also be used to detect HPV proteins in situ present in epithelium tissue as evidenced by IHC staining scored by certified pathologists.

1). The reactivity of the purified anti-HPV Antibodies with HPV Proteins found in Biological Samples. To confirm the binding activity of the HPV antibodies with HPV proteins, purified HPV recombinant proteins and/or HPV containing cell lysate from biological samples can be tested on ELISA or direct EIA. Biological samples include, but are not limited to, cells from cultured cell lines or from clinical samples. As an example, as data shown on Table 5, monoclonal antibodies specific to HPV E6, HPV E7 or HPV L1 proteins were able to react specifically with cell lysate from various cervical cancer cell lines in a direct EIA format while using HEC-1A as negative control. Cell lysate from cervical cancer cell lines, including Caski, Siha, Cxca, Hela, and endometrial cancer cell line like HEC-1A (non-HPV infected) were used to demonstrate detection of HPV E6, E7, or L1 by the HPV monoclonal antibody specific to HPV E6, HPV E7, and HPV L1 respectively as shown in Table 5.

TABLE 5

EIA detection of E6, E7, and L1 proteins in cervical cancer cell lines.

| OD | Anti-HPV16 E6, HPV18 E6 antibody | Anti-HPV18 E6 antibody | Anti-HPV18 E7 antibody | Anti-HPV16 E7 antibody | Anti-HPV16 L1 antibody |
|---|---|---|---|---|---|
| Caski (HPV16+) | 0.392 | 0.48 | 0.442 | 0.464 | 0.355 |
| SiHa (HPV16+) | 1.165 | 1.314 | 1.162 | 1.202 | 1.115 |
| CxCa (HPV16+) | 1.126 | 1.047 | 0.802 | 0.825 | 0.724 |
| Hela (HPV18+) | 0.779 | 0.762 | 0.734 | 0.654 | 0.652 |
| HEC-1A (no HPV) | 0.173 | 0.206 | 0.219 | 0.186 | 0.173 |

Cultured cell lines tested and described herein, include, but not limited to, cervical cancer cells such as Caski (HPV16 positive), Siha (HPV16 positive), Cxca, Hela (HPV18 positive), and endometrial cancer cell line like HEC-1A (no HPV infection). For direct EIA, cells were collected, centrifuged, washed, and lysed to generate cell lysate as analyte. The protein in the cell lysate was quantitated and coated to microtiter plate using the same amount of protein for coating of each sample in each well. The plate was blocked, and detected by each of the HPV monoclonal antibody as indicated followed by HRP conjugated anti-mouse IgG. TMB substrate was added followed by a standard reaction stopping solution. $OD_{450}$ was taken by an ELISA plate reader.

2). The reactivity of the purified anti-HPV Antibodies with HPV Proteins found in clinical samples. Clinical samples to be tested and described herein include, but not limited to, cells from cervical scrapes, body fluid, or serum samples Clinical specimens from cervical scrapes were also obtained for detection of HPV E6, E7 or L1 proteins on EIA.

Cell lysate from various sample source including cervical scrape cells in liquid based solution, culture medium (used for HPV DNA test sample), or pap smear sample demonstrate detection of HPV E6, E7, or L1 from clinical samples on EIA format using various HPV monoclonal antibody described in this invention. To perform the direct EIA described herein, specimens were processed, centrifuged, washed, and lysed to generate cell late as analyte. The proteins in the cell lysate was quantitated and coated to microtiterplate with the same amount of proteins for coating in each well. The plate was blocked, and detected by each HPV monoclonal antibody followed by HRP conjugated anti-mouse IgG. TMB substrate was added followed by a stopping solution. $OD_{450}$ was taken by an ELISA plate reader.

Results shown in Table 6 indicate that each monoclonal antibody detects HPV E6, E7, or L1 protein respectively from SCC samples using pap smear normal (HPV neg) as neg control of the assay. For samples from high-grade HPV DNA pos, one out of three is positive on the E6, E7, and L1 by EIA. These data indicate that E6, E7, or L1 proteins from SCC lysate can be detected by EIA using the monoclonal antibodies described herein, while high-grade HPV DNA positive samples (CIN1/2) may or may not contain detectable HPV E6, E7, or L1 proteins. The high-grade HPV DNA test used in this study was hc2, the only FDA approved HPV DNA test. For those HPV DNA positive but HPV EIA negative samples, it is possible false positive of the HPV DNA assay, or positive HPV DNA detection with no expression of HPV oncogenic proteins. These data indicate that HPV EIA assay described herein provides additional clinical relevance for screening of cervical cancer.

TABLE 6

EIA detection of E6, E7, and L1 proteins in cervical scrapes samples.

| Samples Dx | Anti-HPV18 E6 antibody | Anti-HPV16 E7 antibody | Anti HPV L1 antibody |
|---|---|---|---|
| Squamous cell carcinoma (SCC) | +++ | +++ | +++ |
| Squamous cell carcinoma (SCC) | +++ | +++ | +++ |
| high grade HPV DNA test positive | − | − | − |
| high grade HPV DNA test positive | + | + | + |
| high grade HPV DNA test positive | − | − | − |
| pap smear normal, PCR negative | − | − | − |
| pap smear normal, PCR negative | − | − | − |
| pap smear normal, PCR negative | − | − | − |

3). The reactivity of the purified anti-HPV Antibodies with HPV Proteins in situ by Immunohistochemisty (IHC): Paraffin tissue blocks sectioned into 4 microns were placed on slide and baked at 60° C. for overnight. Deparaffin/hydrate sections were unmasked followed by standard IHC staining procedures. Purified monoclonal antibodies against HPV proteins as described in this invention were diluted to use as the primary antibody. Staining procedure was followed by secondary antibody solution and washing, then followed by appropriate substrate reagent to each section. As soon as the sections developed, slides were immersed in distilled water, sections were counterstained with hematoxylin and dehydrated, and the coverslips were mounted.

As an example, various cervical tissues from various stages of CIN were prepared to perform IHC assay using rabbit polyclonal anti-HPV E7 antibodies described herein. As another examples, a number of cervical biopsy samples were tested in an immunohistochemistry (IHC) assay concurrently as a tissue microarray format using a monoclonal antibody to detect HPV proteins from a variety of HPV types (as confirmed by HPV DNA genotyping). Using a monoclonal antibody against HPV viral proteins and/or oncoproteins, this invention provides antibodies to detect the presence of HPV L1 viral proteins and E6, E7 oncoproteins in clinical samples having either single HPV infection or multiple HPV infections. A single anti-HPV monoclonal antibody as described herein can detect single HPV infection by at least HPV-6, HPV-16, HPV-18, HPV-31, HPV-33, HPV-52, etc, which are cancer-related HPV types (either high risk HPV types or low risk HPV types). A single anti-HPV monoclonal antibody can detect HPV infection by two or more HPV types, such as the combination of HPV-16, HPV-18, HPV-52, HPV-58, HPV-44, HPV-51, HPV-39, HPV-59, etc., which include high risk, low risk, and non-oncogenic α-papillomaviruses.

As an example, the HPV antibodies described in this invention can be applied in clinical utility. The results of the IHC assay demonstrate detection of the HPV E7 protein present in situ from various stages of cervical tissues using a mouse monoclonal anti-HPV E7 antibody. As another example, the antibodies described herein were also used in ICC assay using various cervical tissues from various stages of CIN. As another examples, results of IHC staining using a mouse monoclonal anti-HPV E6 antibody demonstrate detecting the HPV E6 protein present in situ from various stages of CIN tissues. These results indicate that HPV E6 and HPV E7 oncoproteins over-expressed in the dysplasia cells can be specificly detected by the IHC staining using the specific HPV antibodies.

As an example, FIGS. 12A-12D show IHC staining of CIN tissue demonstrated by a mouse monoclonal anti-HPV E6 antibody. Results indicate expression of E6 oncoprotein can be detected early in the precancerous stage of CIN2. Solid Black arrows indicate the specific staining of E6 protein in dysplasia cells, while empty clear arrows indicate the normal cells with no stain. Highly magnified images indicate localization of the E6 proteins expressed early in the nuclear of dysplasia cells.

Figure 32A:
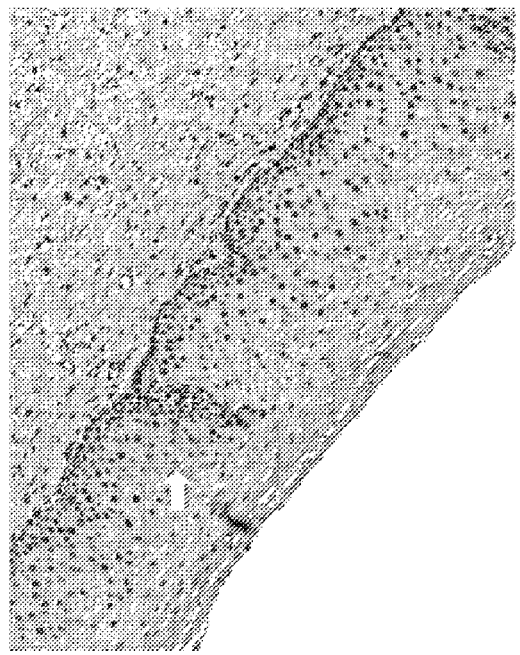
FIG. 32A shows the representative staining image of the dysplasia cells of CIN2 tissues using an anti-E6 monoclonal antibody in an immunohistocytostaining (IHC) assay.
Figure 32B:
FIG. 32B shows the representative staining image of the normal epithelium adjacent to the dysplasia tissue of the CIN2 sample in FIG. 32A.
Figure 32D:
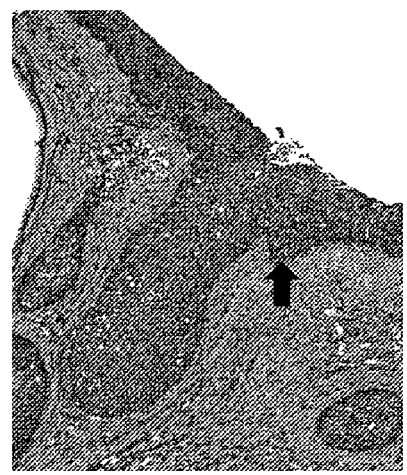
FIG. 32D shows the representative staining image of the dysplasia epithelium of another CIN3 sample stained by the same anti-E6 monoclonal antibody as used in FIG. 32A in an IHC assay.
Figure 32C:
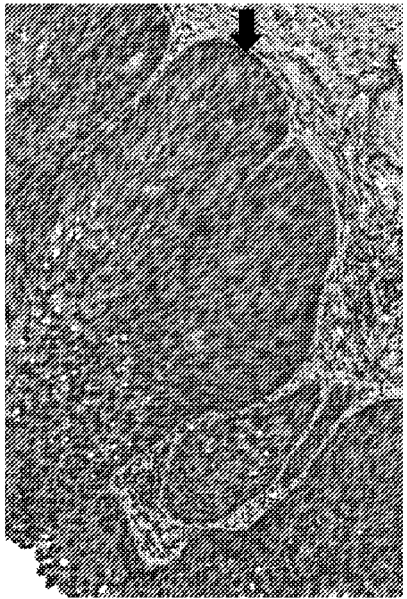
FIG. 32C shows the representative staining image of the dysplasia epithelium of a CIN3 sample stained by the same anti-E6 monoclonal antibody as used in FIG. 32A in an IHC assay, demonstrating specific IHC staining in the nuclear and cytoplasm of dysplasia cells by the anti-E6 monoclonal antibody.

FIG. 32A shows the representative image of the dysplasia cells of CIN2 tissues stained by immunohistocytostaining (IHC) using an anti-E6 monoclonal antibody. FIG. 32B shows the representative image of the adjacent normal epithelium from the dysplasia tissue of the CIN2 sample of FIG. 32A. FIGS. 32C-32D shows the representative image of the dysplasia epithelium of two CIN3 samples stained by IHC using the same anti-E6 monoclonal antibody. These data suggest the IHC staining by E6 monoclonal antibody is specific in the nuclear and cytoplasm of dysplasia cells.

Figure 33B:
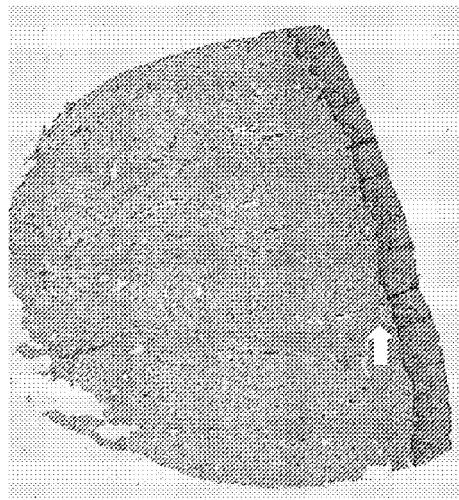
FIG. 33B shows the representative staining image of the normal epithelium (about 15 mm away from the tumor tissue) adjacent the SCC tissue of FIG. 33A.
Figure 33D:
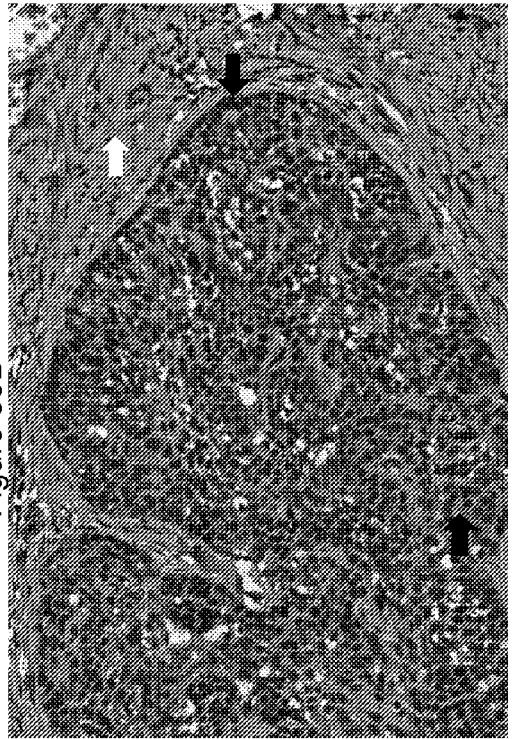
FIG. 33D shows the magnified representative image of the tumor cells from FIG. 33C to view the staining of the cytoplasm of the tumor cells.
Figure 33A:
FIG. 33A shows the representative staining image of the squamocarcinoma (SCC) tissue from tissue microarray using an anti-E7 monoclonal antibody in an immunohistocytostaining (IHC) assay.
Figure 33C:
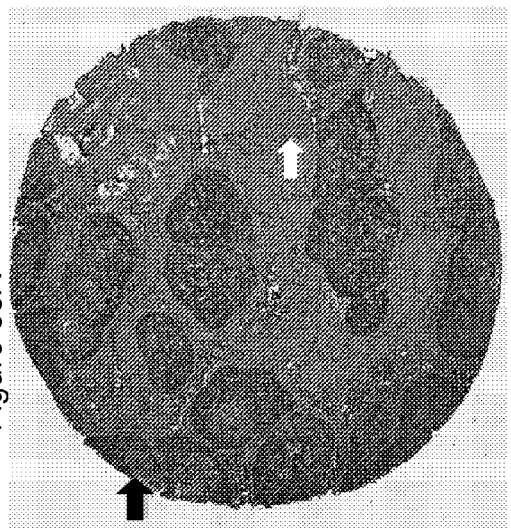
FIG. 33C shows the representative staining image of another SCC sample stained by the same anti-E7 monoclonal antibody as used in FIG. 33A in an IHC assay, demonstrating specific IHC staining in the tumor cells by the anti-E7 monoclonal antibody.

As an another example, FIGS. 13A-13D show IHC staining of squamous cell carcinoma demonstrated by mouse monoclonal HPV E7 antibody. Results indicate expression of E7 oncoprotein can be detected in the tumor cells of SCC tissue. Solid Black arrows indicate the specific staining of E7 protein in dysplasia cells, while empty clear arrows indicate the normal cells with no stain. Highly magnified images indicate localization of the E7 proteins expressed in the cytoplasm of tumor cells, but not in the normal epithelium, or stroma cells. These data suggest the IHC staining by E7 monoclonal antibody is specific in the cytoplasm of tumor cells. FIG. 33A shows the representative image of the squamocarcinoma (SCC) tissue from tissue microarray stained by IHC using an anti-E7 monoclonal antibody. FIG. 33B shows the representative image of the normal epithelium (15 mm away from the tumor tissue) of the SCC subject from FIG. 33A. FIG. 33C shows the representative image of another SCC sample from tissue microarray stained by IHC using the same anti-E7 monoclonal antibody. FIG. 33D shows the magnified representative image of the tumor cells stained in cytoplasm from FIG. 33C.

9. The Reactivity of the Purified Anti-HPV Antibodies with HPV Proteins in Situ by Immunocytochemistry (ICC):

Cervical scrapes collected by Liquid based solution were processed according to the manufacture instruction. The cell preparation was divided into two parts, one for conventional papsmear, the other one for immunostaining. Monolayer of cervical cells on slide was processed by cytospin or thin prep techniques. The cells were then fixed and stained followed by immunostaining protocol. Stained cells are visualized under microscope.

Figure 34C:
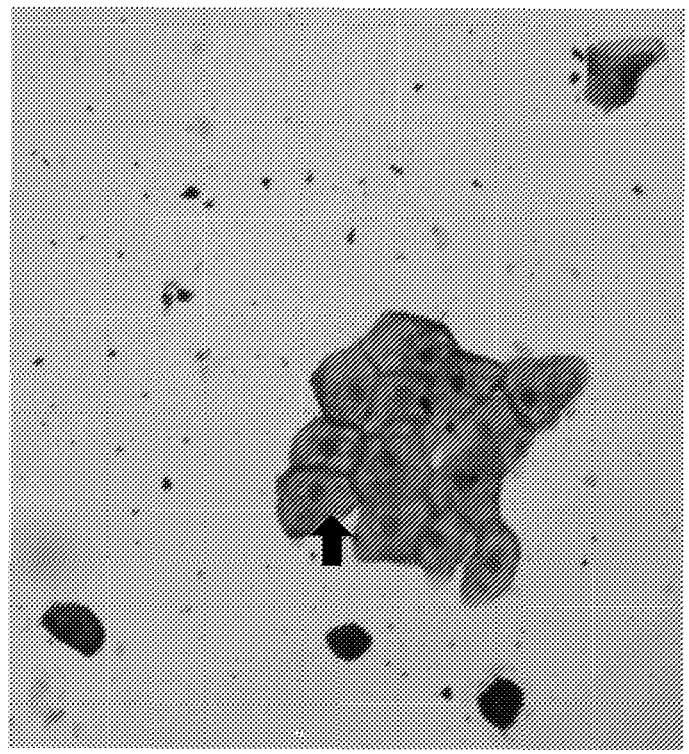
FIG. 34C shows the representative image of cervical cells from an adenocarcinoma (ADC) cervical scrape sample prepared by thin prep and stained by the same anti-E6 antibody shown in FIG. 34B in an ICC assay.
Figure 34B:
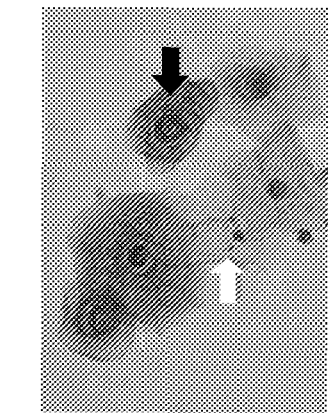
FIG. 34B shows the representative staining image of cervical cells from a CIN3 cervical scrape sample prepared by thin prep and stained by a mouse monoclonal anti-E6 antibody in an ICC assay.
Figure 34A:
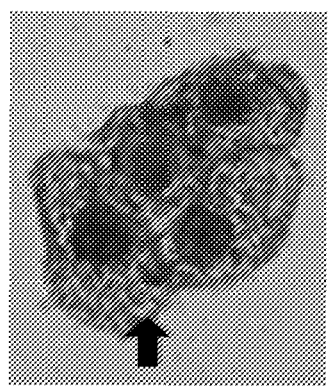
FIG. 34A shows the representative staining image of cervical cells from a CIN2 cervical scrape sample prepared by thin prep and stained by a mouse monoclonal anti-HPV E7 antibody in an immunocytochemistry (ICC) assay.

As an example, FIGS. 34A-34C demonstrate immunocytochemistry assay using anti-HPV antibody. FIG. 34A shows the representative image of cervical cells from a CIN2 cervical scrape sample prepared by thin prep and stained by ICC using a mouse monoclonal anti-HPV E7 antibody. FIG. 34B shows the representative image of cervical cells from a CIN3 cervical scrape sample prepared by thin prep and stained by ICC using a mouse monoclonal anti-E 6 antibody. FIG. 34C shows the representative image of cervical cells from an adenocarcinoma (ADC) cervical scrape sample prepared by thin prep and stained by ICC using the same anti-E6 antibody shown in FIG. 34B.

The one or more immunological assays using antibodies and purified recombinants proteins derived from HPV early and/or late genes as obtained herein serve as reliable indicators whether HPV infection has occurred. In addition, HPV associated malignancy or pre-malignant cell transformation can be assayed. One of the most useful aspects of the invention is in diagnosing cervical carcinoma, both squamous cell carcinoma and adenocarcinoma as well as any epithelial cell abnormality associated with oncogenic HPV infection including koilocytosis; hyperkerotosis; precancerous conditions encompassing intraepithelial neoplasias or intraepithelial lesion; high-grade dysplasias; and invasive or malignant cancers.

In high grade CIN lesions, E6 and E7 are strongly expressed in host basal epithelial cells and interfere substantially with cell cycle control of these replication competent host cells. Expression of HPV oncoproteins interferes with G1-S-Phase regulation in host cells. The HPV E6 and E7 proteins target a plethora of cellular interactions, such as the inactivation of pRB by E7 and the degradation of p53 by E6. High level of HPV E7 proteins inactivates pRB and leads to disruption of E2F-Rb binding. Usually, binding of pRB to E2F blocks E2F driven cell cycle activation. In replicating cells, E2F is regulated by phosphorylation of RB. Rb phosphorylation is normally mediated by cyclin dependent kinases (CDK4, CDK6) that are controlled by several kinase inhibitors (INKs).

What is claimed is:

1. A method of detecting a papillomavirus protein in a human subject, comprising:
    preparing a cell lysate solution using a sample of cells from the human subject, wherein the sample of cells comprises epithelial cells;
    coating a portion of a solid surface with a first coat of the cell lysate solution;
    reacting the cell lysate solution with an anti-HPV monoclonal antibody, wherein the monoclonal antibody specifically binds to a native HPV E7 protein or a native HPV E6 protein from more than one papillomavirus type, and is capable of binding in situ to the protein in a clinical sample;
    forming a complex of the papillomavirus proteins HPV E6 or E7 with the antibody on the portion of the solid surface;
    detecting the complex on the portion of the solid surface, wherein presence of the complex indicates presence of the papillomavirus protein present in the human subject; and
    determining disease stage associated with papillomavirus infection in the human subject based at least in part on the presence of the complex, wherein the presence of the complex indicates the disease stage as a late dysplasia stage.

2. The method of claim 1, wherein the solid surface is selected from a group that comprises a surface of a bead, a surface of a strip, a surface of a rapid test strip, a surface of a membrane, a membrane surface of a vertical flow through device, a surface of a microfluidic device, a surface of a blot membrane, a surface of a protein chip, a glass surface, and a bottom surface of a microtiter plate.

3. The method of claim 1, wherein
    the solid surface comprises a surface of a bead;
    the complex is on the portion of the surface of the bead; and
    the presence of the complex is detected by using FACS (Fluorescence-activated cell sorting).

4. The method of claims 1, wherein
    the solid surface comprises a surface of a rapid test strip, wherein
        the antibody is immobilized on a first end of the rapid test strip;
    a second antibody and the cell lysate solution are added onto a second end of the rapid test strip before flowing laterally on the surface of the rapid test strip; and
    the complex of the papillomavirus with the antibody is formed.

5. The method of claim 1, wherein
the solid surface comprises a membrane surface of a vertical flow-through device, wherein
the antibody is immobilized on the solid surface;
the cell lysate solution and a second antibody are added sequentially onto the solid surface; and
the complex of the papillomavirus with the antibody is formed.

6. The method of claim 1, wherein the solid surface comprises a surface of a microfluidic device.

7. The method of claim 1, wherein the papillomavirus protein in the cell lysate solution is coated on the portion of the solid surface before reacting with the antibody.

8. The method of claim 7, wherein the papillomavirus protein is coated on a surface of a blot membrane.

9. The method of claim 7, wherein the papillomavirus protein is coated on a bottom surface of a microtiter plate.

10. The method of claim 1, wherein the antibody is coated on the solid surface before coating the portion of the solid surface with the first coat of the cell lysate solution.

11. The method of claim 10, wherein the antibody is coated on a surface of a protein chip before reacting with the papillomavirus protein in the cell lysate solution.

12. The method of claim 10, wherein the antibody is coated on a surface of a microfluidic device before reacting with the papillomavirus protein in the cell lysate solution.

13. The method of claim 1, wherein detecting the complex on the portion of the solid surface further comprises
detecting presence of a detection agent pre-labeled on a molecule that is selected from a group comprising the antibody, the papillomavirus protein in the cell lysate solution, a secondary antibody that binds to the antibody, and a second antibody different from the antibody, wherein
the second antibody specifically binds to the papillomavirus protein from one or more papillomavirus types in the sample of cells from the human subject.

14. The method of claim 13, wherein the presence of the detection agent is detected by an assay, wherein
the assay is selected from a group that comprises a direct qualitative visualization of the color change of the agent, a readout by an ELISA reader, a readout by a microarray scanner, a readout by a fluorescent reader, and a readout by a FACS (Fluorescence-activated cell sorting) instrument.

15. The method of claim 1, further comprising
coating the portion of the solid surface with an antibody for a cellular protein and
comparing presence of the cellular protein with the presence of the papillomavirus proteins in the sample of cells from the human subject, wherein the cellular protein is selected from a group that comprises p16INK4a, E2F, Ki-67 (MIB-1), MYC protein, CDK4, cyclin-A, cyclin-B, cyclin-E, telomerase-TERC, MCM2 protein, TOP2A protein, heat shock protein 40 ($HSP_{40}$), heat shock protein 60 ($HSP_{60}$), heat shock protein 70 ($HSP_{70}$), CA9/MN protein, laminin 5, laminin proteins, brn-3a, CDK N2 protein, topoisomerase 2A, microsome maintenance proteins-2, micro some maintenance proteins-4, micro some maintenance proteins-5, survivin protein, VEGF protein, p53, RB, p27(kip1), and p21 (waf).

16. The method of claim 1, wherein the more than one papillomavirus type are selected from a group that comprises high risk HPV types, low risk HPV types, HPV-16, HPV-18, HPV-31, HPV-33, HPV-35, HPV-39, HPV-45, HPV-51, HPV-52, HPV-56, HPV-58, HPV-59, and HPV-68, HPV-6, HPV-11, HPV-42, HPV-43, HPV-44, HPV-53, HPV-54, HPV-55, and HPV-56.

17. The method of claim 1, wherein
the late dysplasia stage is selected from a group that comprises late stage HPV infection, late stage cervical cell lesion, low grade of squamous intraepithelial lesion (LSIL), high grade of squamous intraepithelial lesion (HSIL), atypical squamous cells of undetermined significance (ASCUS), cervical intraepithelial neoplasm stage 1, 2, 3 (CIN1, CIN2, CIN3), developed cervical cancer, adenocarcinoma, and squamous cell carcinoma (SCC).

18. The method of claim 1, wherein the sample of cells is obtained from a cervical swab or a cervical scrape.

19. The method of claim 1, wherein prior to the action of coating with the first coat, coat the portion of the solid surface with a capturing antibody, wherein
the capturing antibody captures the papillomavirus protein in the cell lysate solution.

* * * * *